(12) United States Patent
Van Berkel

(10) Patent No.: US 11,384,098 B2
(45) Date of Patent: Jul. 12, 2022

(54) PYRROLOBENZODIAZEPINE-ANTIBODY CONJUGATES

(71) Applicants: ADC THERAPEUTICS SA, Epalinges (CH); MEDIMMUNE LIMITED, Cambridge (GB)

(72) Inventor: Patricius Hendrikus Cornelis Van Berkel, Epalinges (CH)

(73) Assignees: ADC THERAPEUTICS SA, Epalinges (CH); MEDIMMUNE LIMITED, Cambridge (GB)

( * ) Notice: Subject to any disclaimer, the term of this patent is extended or adjusted under 35 U.S.C. 154(b) by 383 days.

(21) Appl. No.: 16/484,313

(22) PCT Filed: Feb. 8, 2018

(86) PCT No.: PCT/EP2018/053188
§ 371 (c)(1),
(2) Date: Aug. 7, 2019

(87) PCT Pub. No.: WO2018/146199
PCT Pub. Date: Aug. 16, 2018

(65) Prior Publication Data
US 2021/0079020 A1 Mar. 18, 2021

(30) Foreign Application Priority Data

Feb. 8, 2017 (GB) .................................... 1702031
Nov. 22, 2017 (GB) .................................... 1719391
Nov. 22, 2017 (GB) .................................... 1719393
Nov. 22, 2017 (GB) .................................... 1719398

(51) Int. Cl.
*C07D 519/00* (2006.01)
*A61K 47/68* (2017.01)
*A61K 45/06* (2006.01)

(52) U.S. Cl.
CPC ........ *C07D 519/00* (2013.01); *A61K 47/6803* (2017.08); *A61K 47/6849* (2017.08); *A61K 47/6861* (2017.08); *A61K 45/06* (2013.01); *C07K 2317/565* (2013.01)

(58) Field of Classification Search
CPC .. C07D 243/00; C07D 487/02; C07D 519/00; A61K 31/55; A61K 47/6803; A61K 47/6849
See application file for complete search history.

(56) References Cited

U.S. PATENT DOCUMENTS

| 4,816,567 A | 3/1989 | Cabilly et al. |
| 5,583,024 A | 12/1996 | McElroy et al. |
| 5,674,713 A | 10/1997 | McElroy et al. |
| 5,700,670 A | 12/1997 | Yamagishi et al. |
| 7,521,541 B2 | 4/2009 | Eigenbrot et al. |
| 7,723,485 B2 | 5/2010 | Junutula et al. |
| 2008/0206239 A1 | 8/2008 | Jones et al. |

FOREIGN PATENT DOCUMENTS

| JP | 58180487 | | 10/1983 |
| JP | 2013523395 A | | 6/2013 |
| WO | WO 2005079479 | | 9/2005 |
| WO | 2007044515 A1 | | 4/2007 |
| WO | WO 2007085930 | | 8/2007 |
| WO | 2009045957 A1 | | 4/2009 |
| WO | WO 2009052249 | | 4/2009 |
| WO | 2011130183 A2 | | 10/2011 |
| WO | 2011130616 A1 | | 10/2011 |
| WO | WO 2011130598 | | 10/2011 |
| WO | WO-2011130598 A1 | * | 10/2011 ........... C07D 519/00 |
| WO | WO 2011130613 | | 10/2011 |
| WO | WO 2011130616 | | 10/2011 |
| WO | 2012129668 A1 | | 10/2012 |
| WO | 2013055987 A1 | | 4/2013 |
| WO | 2013104050 A2 | | 7/2013 |
| WO | 2014054820 A1 | | 4/2014 |
| WO | WO 2014057074 | | 4/2014 |
| WO | WO 2014057113 | | 4/2014 |
| WO | WO 2014057114 | | 4/2014 |
| WO | WO 2014057115 | | 4/2014 |
| WO | WO 2014057117 | | 4/2014 |
| WO | WO 2014057118 | | 4/2014 |
| WO | WO 2014057119 | | 4/2014 |
| WO | WO 2014057120 | | 4/2014 |
| WO | WO 2014057122 | | 4/2014 |
| WO | WO-2014174111 A1 | * | 10/2014 ......... A61K 47/6803 |
| WO | WO 2015052532 | | 4/2015 |
| WO | WO 2015052533 | | 4/2015 |
| WO | WO 2015052534 | | 4/2015 |
| WO | WO 2015052535 | | 4/2015 |
| WO | WO 2015159076 | | 10/2015 |

(Continued)

OTHER PUBLICATIONS

Altuvia et al., "Ranking potential binding peptides to MHC molecules by a computational threading approach." J. Mol. Biol., 249, 244-250 (1995).

Antonow, D. et al., ""Synthesis of DNA-Interactive Pyrrolo [2,1-c][1,4] benzodiazepines (PBDs)"" Chemical Reviews, 2011, 111(4):2815-2864.

Arima et al., "Studies on Tomaymycin, a New Antibiotic. I. Isolation and Properties of Tomaymycin," J. Antibiotics (1972) 25:437-444.

(Continued)

*Primary Examiner* — Theodore R. Howell
*Assistant Examiner* — George W Kosturko
(74) *Attorney, Agent, or Firm* — Medler, Ferro, Woodhouse & Mills PLLC

(57) ABSTRACT

The present invention relates to pyrrolobenzodiazepines (PBDs) having a labile protecting group in the form of a linker to an antibody.

25 Claims, 6 Drawing Sheets
Specification includes a Sequence Listing.

(56) References Cited

FOREIGN PATENT DOCUMENTS

| WO | 2016054315 A1 | 4/2016 | | |
|---|---|---|---|---|
| WO | WO 2016053107 | 4/2016 | | |
| WO | WO-2016053107 A1 | * 4/2016 | ......... | A61K 47/6803 |
| WO | WO 2016083468 | 6/2016 | | |
| WO | WO 2016166297 | 10/2016 | | |
| WO | WO 2016166298 | 10/2016 | | |
| WO | WO 2016166299 | 10/2016 | | |
| WO | WO 2016166300 | 10/2016 | | |
| WO | WO 2016166302 | 10/2016 | | |
| WO | WO 2016166304 | 10/2016 | | |
| WO | WO 2016166305 | 10/2016 | | |
| WO | WO 2016166307 | 10/2016 | | |
| WO | WO 2016166341 | 10/2016 | | |
| WO | WO 2016177438 | 11/2016 | | |
| WO | 2017137456 A1 | 8/2017 | | |
| WO | 2017137457 A1 | 8/2017 | | |
| WO | 2017137458 A1 | 8/2017 | | |

OTHER PUBLICATIONS

Berge et al., "Pharmaceutical Salts," J. Pharm. Sci. (1977) 66:1-19.
Bose et al., "New Approaches to Pyrrolo[2,1-c][1,4]benzodiazepines: Synthesis, DNA-binding and cytotoxicity of DC-81," Tetrahedron, 48, 751-758 (1992).
Carter, P., "Potent antibody therapeutics by design," (2006) Nature Reviews Immunology 6:343-357.
Clackson et al., "Making antibody fragments using phage display libraries," (1991) Nature, 352:624-628.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use• of ATP bioluminescence as a measure of cell proliferation and cytotoxicity," (1993) J. Immunol. Meth. 160:81-88.
Dall'Acqua, W. F. et al., "Antibody humanization by framework shuffling" Methods, 36, 43-60 (2005).
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Genbank accession No. CAA76847.1 (2001).
Genbank accession No. CAA78163 (2005).
Genbank accession No. AAF23613 (2000).
Genbank accession No. AAC50348 (1996).
Genbank accession No. U40434 (1996).
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Synthesis of the first example of a C2—C3/C2'—C3'-endo unsaturated pyrrolo[2,1-c][1,4]benzodiazepine dimer," Biorg. Med. Chem. Lett. (2001) 11:2859-2862.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Hara et al., "DC 102, a new glycosidic pyrrolo(1,4)benzodiazepine antibiotic produced by Streptomyces sp.", J. Antibiotics, 41, 702-704 (1988).
Hochlowski, J. et al., "Abbeymycin, a new anthramycin-type antibiotic produced by a streptomycete," J. Antibiotics, 40, 145-148 (1987).

Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Itoh et al., "Sibanomicin, a new pyrrolo(1,4)benzodiazepine antitumor antibiotic produced by a *micromonospora* sp." J. Antibiotics, 41, 1281-1284 (1988).
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Junutula, et al., "Site-specific conjugation of a cytotoxic drug to an antibody improves the therapeutic index," 2008b Nature Biotech., 26(8):925-932.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kunimoto et al., "Mazethramycin, a new member of anthramycin group antibiotics," J. Antibiotics, 33, 665-667 (1980).
Lambert J., "Drug-conjugated monoclonal antibodies for the treatment of cancer," (2005) Current Opin. In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Leber, J.D. et al., "A revised structure forsibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Lonberg, "Fully Human antibodies from transgenic mouse and phage display platforms" Curr. Opinion, 20(4), 450-459 (2008).
Marks et al., "By-passing Immunization, Human Antibodies from V-gene Libraries Displayed on Phage," (1991) J. Mol. Biol., 222:581-597.
McDonagh, "Engineered antibody-drug conjugates with defined sites and stoichiometries of drug attachment," (2006) Protein Eng. Design & Sel. 19(7): 299-307.
Morrison et al., "Chimeric human antibody molecules: Mouse antigen-binding domains with human constant region domains," (1984) Proc. Natl. Acad. Sci. USA, 81:6851-6855.
Payne, G. "Progress in immunoconjugate cancer therapeutics," (2003) Cancer Cell 3:207-212.
Sanderson et al., "In vivo Drug-Linker Stability of an Anti-CD30 Dipeptide-Linked Auristatin Immunoconjugate," (2005) Clin. Cancer Res. 11:843-852.
Shimizu, K. et al., "Prothracarcin, a Novel Antitumor Antibiotic," J. Antibiotics, 35, 972-978 (1982).
Syrigos and Epenetos, "Antibody Directed Enzyme Prodrug Therapy (ADEPT): A Review of the Experimental and Clinical Considerations," (1999) Anticancer Research 19:605-614.
Thurston, D.E. and Bose, D.S., "Synthesis of DNA-Interactive Pyrrolo[2,1-c][1,4]benzodiazepines," Chem. Rev., 94:433-465 (1994).

(56) References Cited

OTHER PUBLICATIONS

Thurston, D.E. and Thompson, A.S., "The molecular recognition of DNA," Chem. Brit., 26, 767-772 (1990).

Trail et al., "Monoclonal antibody drug immunoconjugates for targeted treatment of cancer," (2003) Cancer Immunol. Immunother. 52:328-337.

Tsunakawa, M. et al., "Porothramycin, a new antibiotic of the anthramycin group: Production, isolation, structure and biological activity," J. Antibiotics, 41:1366-1373 (1988).

van Geel et al., "Chemoenzymatic Conjugation of Toxic Payloads to the Globally Conserved N-Glycan of Native mAbs Provides Homogeneous and Highly Efficacious Antibody-Drug Conjugates." Bioconjug Chem. Nov. 18, 2015;26(11):2233-42.

Wu et al., "Arming antibodies: prospects and challenges for immunoconjugates," (2005) Nature Biotech. 23(9):1137-1145.

Xie et al., "In vivo behaviour of antibody-drug conjugates for the targeted treatment of cancer," (2006) Expert. Opin Biol. Ther. 6(3):281-291.

Zhao et al., "Novel Antibody Therapeutics Targeting Mesothelin in Solid Tumors," (2016) Clinical Cancer Drugs 3(2):76-86.

Alberts et al., "Molecular Biology of the Cell," $3^{rd}$ Edition:186-189 (1994).

Brock et al., "Biology of Microoganisms," $8^{th}$ Edition:848-849 (1997).

Harlow et al., "Antibodies A Laboratory Manual," Contents, pages i-ix (1988).

Hartley J., "The development of pyrrolobenzodiazepines as antitumour agents," Expert Opinion on Investigational Drugs 20(6):733-744 (2011).

Hartley et al., "Pre-clinical pharmacology and mechanism of action of SG3199, the pyrrolobenzodiazepine (PBD) dimer warhead component of antibody-drug conjugate (ADC) payload tesirine," Scientific Reports 8(1):10479 (2018).

Nicolaou et al., "Calicheamicin θ 1I: A Rationally Designed Molecule with Extremely Potent and Selective DNA Cleaving Properties and Apoptosis Inducing Activity," Angewandte Chemie International Edition, 33(2):183-186 (1994).

Stryer L., "Biochemistry," $4^{th}$ Edition: 365-367 (1995).

Takeuchi et al., "Neothramycins A and B, new antitumor antibiotics," Journal of Antibiotics 29(1):93-96 (1976).

\* cited by examiner

A

B

SEQUENCE LISTING

<160> NUMBER OF SEQ ID NOS: 246

<210> SEQ ID NO 1
<211> LENGTH: 121
<212> TYPE: PRT
<213> ORGANISM: Artificial Sequence
<220> FEATURE:
<223> OTHER INFORMATION: HuBa-1-3d VH

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Lys Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Gly Gly Leu Arg Glu Tyr Tyr Ala Met Asp Tyr Trp Gly
            100                 105                 110

Gln Gly Thr Met Val Thr Val Ser Ser
        115                 120

<210> SEQ ID NO 2
<211> LENGTH: 113
<212> TYPE: PRT
<213> ORGANISM: Artificial Sequence
<220> FEATURE:
<223> OTHER INFORMATION: HuBa-1-3d VL

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Pro Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Pro Thr Phe Gly Gln Gly Thr Lys Leu Glu Ile

```
                  100                 105                 110
Lys

<210> SEQ ID NO 3
<211> LENGTH: 450
<212> TYPE: PRT
<213> ORGANISM: Artificial Sequence
<220> FEATURE:
<223> OTHER INFORMATION: HuBa-1-3d Heavy Chain
<220> FEATURE:
<221> NAME/KEY: MOD_RES
<222> LOCATION: (301)..(301)
<223> OTHER INFORMATION: Xaa is Asn297

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met His Trp Val Arg Gln Ala Pro Gly Gln Gly Leu Glu Trp Ile
            35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Xaa Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                    325                 330                 335
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 4
<211> LENGTH: 220
<212> TYPE: PRT
<213> ORGANISM: Artificial Sequence
<220> FEATURE:
<223> OTHER INFORMATION: HuBa-1-3d Light Chain

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
            35                  40                  45

Pro Pro Lys Leu Leu Val Tyr Phe Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Pro Thr Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220
```

```
<210> SEQ ID NO 5
<211> LENGTH: 5
<212> TYPE: PRT
<213> ORGANISM: Artificial Sequence
<220> FEATURE:
<223> OTHER INFORMATION: HuBa-1-3d VH CDR1

<400> SEQUENCE: 5

Asp Tyr Ala Met His
1               5

<210> SEQ ID NO 6
<211> LENGTH: 17
<212> TYPE: PRT
<213> ORGANISM: Artificial Sequence
<220> FEATURE:
<223> OTHER INFORMATION: HuBa-1-3d VH CDR2

<400> SEQUENCE: 6

Val Ile Ser Thr Tyr Tyr Gly Asn Thr Asn Tyr Asn Gln Lys Phe Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: HuBa-1-3d VH CDR3

<400> SEQUENCE: 7

Gly Gly Leu Arg Glu Tyr Tyr Tyr Ala Met Asp Tyr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: HuBa-1-3d VL CDR1

<400> SEQUENCE: 8

Lys Ser Ser Gln Ser Leu Leu Asn Ser Ser Asn Gln Lys Asn Tyr Leu
1               5                   10                  15

Ala

<210> SEQ ID NO 9
<211> LENGTH: 7
<212> TYPE: PRT
<213> ORGANISM: Artificial Sequence
<220> FEATURE:
<223> OTHER INFORMATION: HuBa-1-3d VL CDR2

<400> SEQUENCE: 9

Phe Ala Ser Thr Arg Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: HuBa-1-3d VL CDR3

<400> SEQUENCE: 10

Gln Gln His Tyr Ser Thr Pro Pro Thr
```

```
<210> SEQ ID NO 11
<211> LENGTH: 451
<212> TYPE: PRT
<213> ORGANISM: Artificial Sequence
<220> FEATURE:
<223> OTHER INFORMATION: HuBa-1-3d Heavy Chain, terminal K
<220> FEATURE:
<221> NAME/KEY: MOD_RES
<222> LOCATION: (301)..(301)
<223> OTHER INFORMATION: Xaa is Asn297

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Leu Arg Glu Tyr Tyr Tyr Ala Met Asp Tyr Trp Gly
            100                 105                 110

Gln Gly Thr Met Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Xaa Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 12
<211> LENGTH: 383
<212> TYPE: PRT
<213> ORGANISM: Homo sapiens

<400> SEQUENCE: 12

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
            20                  25                  30

Gln Asn Gly Phe Cys Glu Asp Asp Asn Val Cys Arg Cys His Val Gly
        35                  40                  45

Trp Gln Gly Pro Leu Cys Asp Gln Cys Val Thr Ser Pro Gly Cys Leu
    50                  55                  60

His Gly Leu Cys Gly Glu Pro Gly Gln Cys Ile Cys Thr Asp Gly Trp
65                  70                  75                  80

Asp Gly Glu Leu Cys Asp Arg Asp Val Arg Ala Cys Ser Ser Ala Pro
                85                  90                  95

Cys Ala Asn Asn Gly Thr Cys Val Ser Leu Asp Gly Leu Tyr Glu
            100                 105                 110

Cys Ser Cys Ala Pro Gly Tyr Ser Gly Lys Asp Cys Gln Lys Lys Asp
        115                 120                 125

Gly Pro Cys Val Ile Asn Gly Ser Pro Cys Gln His Gly Gly Thr Cys
    130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255
```

```
Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
        275                 280                 285

Met Lys Glu Leu Asn Lys Lys Thr Pro Leu Leu Thr Glu Gly Gln Ala
    290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Asn Leu Leu Leu Gln
            340                 345                 350

Tyr Asn Ser Gly Glu Asp Leu Ala Val Asn Ile Ile Phe Pro Glu Lys
        355                 360                 365

Ile Asp Met Thr Thr Phe Ser Lys Glu Ala Gly Asp Glu Ile
    370                 375                 380

<210> SEQ ID NO 13
<211> LENGTH: 383
<212> TYPE: PRT
<213> ORGANISM: Homo sapiens

<400> SEQUENCE: 13

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
            20                  25                  30

Gln Asn Gly Phe Cys Glu Asp Asp Asn Val Cys Arg Cys Gln Pro Gly
        35                  40                  45

Trp Gln Gly Pro Leu Cys Asp Gln Cys Val Thr Ser Pro Gly Cys Leu
    50                  55                  60

His Gly Leu Cys Gly Glu Pro Gly Gln Cys Ile Cys Thr Asp Gly Trp
65                  70                  75                  80

Asp Gly Glu Leu Cys Asp Arg Asp Val Arg Ala Cys Ser Ser Ala Pro
                85                  90                  95

Cys Ala Asn Asn Arg Thr Cys Val Ser Leu Asp Asp Gly Leu Tyr Glu
            100                 105                 110

Cys Ser Cys Ala Pro Gly Tyr Ser Gly Lys Asp Cys Gln Lys Lys Asp
        115                 120                 125

Gly Pro Cys Val Ile Asn Gly Ser Pro Cys Gln His Gly Gly Thr Cys
    130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
```

```
                    245                 250                 255
Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
        275                 280                 285

Met Lys Glu Leu Asn Lys Lys Thr Pro Leu Leu Thr Glu Gly Gln Ala
    290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Asn Leu Leu Leu Gln
            340                 345                 350

Tyr Asn Ser Gly Glu Asp Leu Ala Val Asn Ile Ile Phe Pro Glu Lys
        355                 360                 365

Ile Asp Met Thr Thr Phe Ser Lys Glu Ala Gly Asp Glu Glu Ile
    370                 375                 380
```

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
<400> SEQUENCE: 61
000

<210> SEQ ID NO 62
<400> SEQUENCE: 62
000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 116
<212> TYPE: PRT
<213> ORGANISM: Artificial Sequence
<220> FEATURE:
<223> OTHER INFORMATION: 3A4 VH

<400> SEQUENCE: 101

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Lys Gln Ala Pro Gly Gln Gly Leu Glu Trp Ile
            35                  40                  45

Gly Asp Ile Asn Pro Tyr Asn Gly Asp Thr Asn Tyr Asn Gln Lys Phe
 50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser
        115

<210> SEQ ID NO 102
<211> LENGTH: 112
<212> TYPE: PRT
<213> ORGANISM: Artificial Sequence
<220> FEATURE:
<223> OTHER INFORMATION: 3A4 VL

<400> SEQUENCE: 102

Asp Ile Val Met Thr Gln Thr Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 103
<211> LENGTH: 445
<212> TYPE: PRT
<213> ORGANISM: Artificial Sequence
<220> FEATURE:
<223> OTHER INFORMATION: 3A4 Heavy Chain
<220> FEATURE:
<221> NAME/KEY: MOD_RES
<222> LOCATION: (296)..(296)
<223> OTHER INFORMATION: Xaa is Asn297

<400> SEQUENCE: 103

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Lys Gln Ala Pro Gly Gln Gly Leu Glu Trp Ile
            35                  40                  45

Gly Asp Ile Asn Pro Tyr Asn Gly Asp Thr Asn Tyr Asn Gln Lys Phe
 50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95
Ala Arg Asp Pro Gly Ala Met Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Xaa Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 104
<211> LENGTH: 219
<212> TYPE: PRT
<213> ORGANISM: Artificial Sequence
<220> FEATURE:
<223> OTHER INFORMATION: 3A4 Light Chain

<400> SEQUENCE: 104

Asp Ile Val Met Thr Gln Thr Pro Leu Ser Leu Pro Val Thr Pro Gly
```

```
              1               5                  10                 15
Glu Pro Ala Ser Ile Ser Cys Arg Ser Ser Gln Ser Leu Leu His Ser
            20                  25                 30

Asn Gly Asn Thr Tyr Leu Glu Trp Tyr Leu Gln Lys Pro Gly Gln Ser
        35                  40                 45

Pro Gln Leu Leu Ile Tyr Thr Val Ser Asn Arg Phe Ser Gly Val Pro
    50                  55                 60

Asp Arg Phe Ser Gly Ser Gly Ser Gly Thr Asp Phe Thr Leu Lys Ile
65                  70                 75                      80

Ser Arg Val Glu Ala Glu Asp Val Gly Val Tyr Tyr Cys Phe Gln Gly
                85                  90                 95

Ser His Val Pro Leu Thr Phe Gly Gln Gly Thr Lys Leu Glu Ile Lys
                100                 105                110

Arg Thr Val Ala Ala Pro Ser Val Phe Ile Phe Pro Pro Ser Asp Glu
            115                 120                125

Gln Leu Lys Ser Gly Thr Ala Ser Val Val Cys Leu Leu Asn Asn Phe
        130                 135                140

Tyr Pro Arg Glu Ala Lys Val Gln Trp Lys Val Asp Asn Ala Leu Gln
145                 150                 155                     160

Ser Gly Asn Ser Gln Glu Ser Val Thr Glu Gln Asp Ser Lys Asp Ser
                165                 170                175

Thr Tyr Ser Leu Ser Ser Thr Leu Thr Leu Ser Lys Ala Asp Tyr Glu
                180                 185                190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215
```

<210> SEQ ID NO 105
<211> LENGTH: 10
<212> TYPE: PRT
<213> ORGANISM: Artificial Sequence
<220> FEATURE:
<223> OTHER INFORMATION: 3A4 VH CDR1

<400> SEQUENCE: 105

```
Gly Tyr Thr Phe Thr Asp Asp Tyr Met Ser
1               5                   10
```

<210> SEQ ID NO 106
<211> LENGTH: 10
<212> TYPE: PRT
<213> ORGANISM: Artificial Sequence
<220> FEATURE:
<223> OTHER INFORMATION: 3A4 VH CDR2

<400> SEQUENCE: 106

```
Asp Ile Asn Pro Tyr Asn Gly Asp Thr Asn
1               5                   10
```

<210> SEQ ID NO 107
<211> LENGTH: 7
<212> TYPE: PRT
<213> ORGANISM: Artificial Sequence
<220> FEATURE:
<223> OTHER INFORMATION: 3A4 VH CDR3

<400> SEQUENCE: 107

```
Asp Pro Gly Ala Met Asp Tyr
1               5
```

<210> SEQ ID NO 108
<211> LENGTH: 16
<212> TYPE: PRT
<213> ORGANISM: Artificial Sequence
<220> FEATURE:
<223> OTHER INFORMATION: 3A4 VL CDR1

<400> SEQUENCE: 108

Arg Ser Ser Gln Ser Leu Leu His Ser Asn Gly Asn Thr Tyr Leu Glu
1               5                   10                  15

<210> SEQ ID NO 109
<211> LENGTH: 7
<212> TYPE: PRT
<213> ORGANISM: Artificial Sequence
<220> FEATURE:
<223> OTHER INFORMATION: 3A4 VL CDR2

<400> SEQUENCE: 109

Thr Val Ser Asn Arg Phe Ser
1               5

<210> SEQ ID NO 110
<211> LENGTH: 9
<212> TYPE: PRT
<213> ORGANISM: Artificial Sequence
<220> FEATURE:
<223> OTHER INFORMATION: 3A4 VL CDR3

<400> SEQUENCE: 110

Phe Gln Gly Ser His Val Pro Leu Thr
1               5

<210> SEQ ID NO 111
<211> LENGTH: 446
<212> TYPE: PRT
<213> ORGANISM: Artificial Sequence
<220> FEATURE:
<223> OTHER INFORMATION: 3A4 Heavy Chain, terminal K
<220> FEATURE:
<221> NAME/KEY: MOD_RES
<222> LOCATION: (296)..(296)
<223> OTHER INFORMATION: Xaa is Asn297

<400> SEQUENCE: 111

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
                20                  25                  30

Tyr Met Ser Trp Val Lys Gln Ala Pro Gly Gln Gly Leu Glu Trp Ile
            35                  40                  45

Gly Asp Ile Asn Pro Tyr Asn Gly Asp Thr Asn Tyr Asn Gln Lys Phe
        50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu

```
               130                 135                 140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Xaa Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 112
<211> LENGTH: 84
<212> TYPE: PRT
<213> ORGANISM: Homo sapiens

<400> SEQUENCE: 112

Met Asp Asp Ala Ala Pro Arg Val Glu Gly Val Pro Val Ala Val
1               5                   10                  15

His Lys His Ala Leu His Asp Gly Leu Arg Gln Val Ala Gly Pro Gly
                20                  25                  30

Ala Ala Ala Ala His Leu Pro Arg Trp Pro Pro Gln Leu Ala Ala
            35                  40                  45

Ser Arg Arg Glu Ala Pro Pro Leu Ser Gln Arg Pro His Arg Thr Gln
50                  55                  60
```

Gly Ala Gly Ser Pro Pro Glu Thr Asn Glu Lys Leu Thr Asn Pro Gln
65                  70                  75                  80

Val Lys Glu Lys

<210> SEQ ID NO 113
<211> LENGTH: 112
<212> TYPE: PRT
<213> ORGANISM: Artificial Sequence
<220> FEATURE:
<223> OTHER INFORMATION: 3A4-L2 VL

<400> SEQUENCE: 113

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 114
<211> LENGTH: 219
<212> TYPE: PRT
<213> ORGANISM: Artificial Sequence
<220> FEATURE:
<223> OTHER INFORMATION: 3A4-L2 Light Chain

<400> SEQUENCE: 114

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 115
<211> LENGTH: 112
<212> TYPE: PRT
<213> ORGANISM: Artificial Sequence
<220> FEATURE:
<223> OTHER INFORMATION: 3A4-K4 VL

<400> SEQUENCE: 115
```

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu His Ser
            20                  25                  30

Asn Gly Asn Thr Tyr Leu Glu Trp Tyr Gln Gln Lys Pro Gly Gln Pro
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
                85                  90                  95

Ser His Val Pro Leu Thr Phe Gly Gln Gly Thr Lys Val Glu Ile Lys
            100                 105                 110
```

```
<210> SEQ ID NO 116
<211> LENGTH: 219
<212> TYPE: PRT
<213> ORGANISM: Artificial Sequence
<220> FEATURE:
<223> OTHER INFORMATION: 3A4-K4 Light Chain

<400> SEQUENCE: 116
```

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu His Ser
            20                  25                  30

Asn Gly Asn Thr Tyr Leu Glu Trp Tyr Gln Gln Lys Pro Gly Gln Pro
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
                85                  90                  95

Ser His Val Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148
<400> SEQUENCE: 148
000

<210> SEQ ID NO 149
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160

```
<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171
```

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 122
<212> TYPE: PRT
<213> ORGANISM: Artificial Sequence
<220> FEATURE:
<223> OTHER INFORMATION: XA4 VH

<400> SEQUENCE: 201

```
Gln Val His Leu Val Glu Ser Gly Gly Val Val Gln Pro Gly Arg
  1               5                  10                  15

Ser Leu Arg Leu Ser Cys Val Ala Ser Gly Ile Thr Phe Arg Ile Tyr
                 20                  25                  30

Gly Met His Trp Val Arg Gln Ala Pro Gly Lys Gly Leu Glu Trp Val
             35                  40                  45

Ala Val Leu Trp Tyr Asp Gly Ser His Glu Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Asp Gly Asp Tyr Tyr Ser Gly Ser Pro Leu Asp Tyr Trp
            100                 105                 110
```

```
Gly Gln Gly Thr Leu Val Thr Val Ser Ser
        115                 120

<210> SEQ ID NO 202
<211> LENGTH: 107
<212> TYPE: PRT
<213> ORGANISM: Artificial Sequence
<220> FEATURE:
<223> OTHER INFORMATION: XA4 VL

<400> SEQUENCE: 202

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 203
<211> LENGTH: 451
<212> TYPE: PRT
<213> ORGANISM: Artificial Sequence
<220> FEATURE:
<223> OTHER INFORMATION: XA4 Heavy Chain
<220> FEATURE:
<221> NAME/KEY: MOD_RES
<222> LOCATION: (302)..(302)
<223> OTHER INFORMATION: Xaa is Asn297

<400> SEQUENCE: 203

Gln Val His Leu Val Glu Ser Gly Gly Val Val Gln Pro Gly Arg
1               5                   10                  15

Ser Leu Arg Leu Ser Cys Val Ala Ser Gly Ile Thr Phe Arg Ile Tyr
            20                  25                  30

Gly Met His Trp Val Arg Gln Ala Pro Gly Lys Gly Leu Glu Trp Val
        35                  40                  45

Ala Val Leu Trp Tyr Asp Gly Ser His Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Asp Gly Asp Tyr Tyr Ser Gly Ser Pro Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

```
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
        260                 265                 270
His Glu Asp Pro Glu Val Lys Phe Asn Trp Tyr Val Asp Gly Val Glu
    275                 280                 285
Val His Asn Ala Lys Thr Lys Pro Arg Glu Glu Gln Tyr Xaa Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
            325                 330                 335
Ile Glu Lys Thr Ile Ser Lys Ala Lys Gly Gln Pro Arg Glu Pro Gln
        340                 345                 350
Val Tyr Thr Leu Pro Pro Ser Arg Glu Glu Met Thr Lys Asn Gln Val
    355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
        420                 425                 430
Met His Glu Ala Leu His Asn His Tyr Thr Gln Lys Ser Leu Ser Leu
    435                 440                 445
Ser Pro Gly
    450

<210> SEQ ID NO 204
<211> LENGTH: 214
<212> TYPE: PRT
<213> ORGANISM: Artificial Sequence
<220> FEATURE:
<223> OTHER INFORMATION: XA4 Light Chain

<400> SEQUENCE: 204

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro Leu
                    85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 205
<211> LENGTH: 5
<212> TYPE: PRT
<213> ORGANISM: Artificial Sequence
<220> FEATURE:
<223> OTHER INFORMATION: XA4 VH CDR1

<400> SEQUENCE: 205

```
Ile Tyr Gly Met His
1               5
```

<210> SEQ ID NO 206
<211> LENGTH: 17
<212> TYPE: PRT
<213> ORGANISM: Artificial Sequence
<220> FEATURE:
<223> OTHER INFORMATION: XA4 VH CDR2

<400> SEQUENCE: 206

```
Val Leu Trp Tyr Asp Gly Ser His Glu Tyr Tyr Ala Asp Ser Val Lys
1               5                   10                  15

Gly
```

<210> SEQ ID NO 207
<211> LENGTH: 13
<212> TYPE: PRT
<213> ORGANISM: Artificial Sequence
<220> FEATURE:
<223> OTHER INFORMATION: XA4 VH CDR3

<400> SEQUENCE: 207

```
Asp Gly Asp Tyr Tyr Asp Ser Gly Ser Pro Leu Asp Tyr
1               5                   10
```

<210> SEQ ID NO 208
<211> LENGTH: 11
<212> TYPE: PRT
<213> ORGANISM: Artificial Sequence
<220> FEATURE:
<223> OTHER INFORMATION: XA4 VL CDR1

<400> SEQUENCE: 208

Arg Ala Ser Gln Ser Val Ser Ser Tyr Leu Ala
1               5                   10

<210> SEQ ID NO 209
<211> LENGTH: 7
<212> TYPE: PRT
<213> ORGANISM: Artificial Sequence
<220> FEATURE:
<223> OTHER INFORMATION: XA4 VL CDR2

<400> SEQUENCE: 209

Asp Ala Ser Asn Arg Ala Thr
1               5

<210> SEQ ID NO 210
<211> LENGTH: 9
<212> TYPE: PRT
<213> ORGANISM: Artificial Sequence
<220> FEATURE:
<223> OTHER INFORMATION: XA4 VL CDR3

<400> SEQUENCE: 210

Gln Gln Arg Ser Asn Trp Pro Leu Thr
1               5

<210> SEQ ID NO 211
<211> LENGTH: 452
<212> TYPE: PRT
<213> ORGANISM: Artificial Sequence
<220> FEATURE:
<223> OTHER INFORMATION: XA4 Heavy Chain, terminal K
<220> FEATURE:
<221> NAME/KEY: MOD_RES
<222> LOCATION: (302)..(302)
<223> OTHER INFORMATION: Xaa is Asn297

<400> SEQUENCE: 211

Gln Val His Leu Val Glu Ser Gly Gly Val Val Gln Pro Gly Arg
1               5                   10                  15

Ser Leu Arg Leu Ser Cys Val Ala Ser Gly Ile Thr Phe Arg Ile Tyr
                20                  25                  30

Gly Met His Trp Val Arg Gln Ala Pro Gly Lys Gly Leu Glu Trp Val
            35                  40                  45

Ala Val Leu Trp Tyr Asp Gly Ser His Glu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Asp Gly Asp Tyr Tyr Ser Gly Ser Pro Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

-continued

```
Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Xaa Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 212
<211> LENGTH: 119
<212> TYPE: PRT
<213> ORGANISM: Artificial Sequence
<220> FEATURE:
<223> OTHER INFORMATION: XFT VH

<400> SEQUENCE: 212

Gln Val Glu Leu Val Gln Ser Gly Ala Val Lys Lys Pro Gly Glu Ser
1               5                   10                  15

Leu Lys Ile Ser Cys Lys Gly Ser Gly Tyr Ser Phe Thr Ser Tyr Trp
            20                  25                  30

Ile Gly Trp Val Arg Gln Ala Pro Gly Lys Gly Leu Glu Trp Met Gly
        35                  40                  45

Ile Ile Asp Pro Gly Asp Ser Arg Thr Arg Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95
```

```
Arg Gly Gln Leu Tyr Gly Gly Thr Tyr Met Asp Gly Trp Gly Gln Gly
            100                 105                 110

Thr Leu Val Thr Val Ser Ser
        115

<210> SEQ ID NO 213
<211> LENGTH: 111
<212> TYPE: PRT
<213> ORGANISM: Artificial Sequence
<220> FEATURE:
<223> OTHER INFORMATION: XFT VL

<400> SEQUENCE: 213

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Ser Val Ser Trp Tyr Gln Gln His Pro Gly Lys Ala Pro Lys Leu
        35                  40                  45

Met Ile Tyr Gly Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Ile Glu
                85                  90                  95

Ser Ala Thr Pro Val Phe Gly Gly Gly Thr Lys Leu Glu Ile Lys
            100                 105                 110

<210> SEQ ID NO 214
<211> LENGTH: 448
<212> TYPE: PRT
<213> ORGANISM: Artificial Sequence
<220> FEATURE:
<223> OTHER INFORMATION: XFT Heavy Chain
<220> FEATURE:
<221> NAME/KEY: MOD_RES
<222> LOCATION: (299)..(299)
<223> OTHER INFORMATION: Xaa is Asn297

<400> SEQUENCE: 214

Gln Val Glu Leu Val Gln Ser Gly Ala Val Lys Lys Pro Gly Glu Ser
1               5                   10                  15

Leu Lys Ile Ser Cys Lys Gly Ser Gly Tyr Ser Phe Thr Ser Tyr Trp
            20                  25                  30

Ile Gly Trp Val Arg Gln Ala Pro Gly Lys Gly Leu Glu Trp Met Gly
        35                  40                  45

Ile Ile Asp Pro Gly Asp Ser Arg Thr Arg Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Gly Gln Leu Tyr Gly Gly Thr Tyr Met Asp Gly Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Xaa Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 215
<211> LENGTH: 218
<212> TYPE: PRT
<213> ORGANISM: Artificial Sequence
<220> FEATURE:
<223> OTHER INFORMATION: XFT Light Chain

<400> SEQUENCE: 215

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Ser Val Ser Trp Tyr Gln Gln His Pro Gly Lys Ala Pro Lys Leu
        35                  40                  45

Met Ile Tyr Gly Val Asn Asn Arg Pro Ser Gly Val Ser Asn Arg Phe
    50                  55                  60
```

-continued

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Ile Glu
                 85                  90                  95

Ser Ala Thr Pro Val Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 216
<211> LENGTH: 10
<212> TYPE: PRT
<213> ORGANISM: Artificial Sequence
<220> FEATURE:
<223> OTHER INFORMATION: XFT VH CDR1

<400> SEQUENCE: 216

Gly Tyr Ser Phe Thr Ser Tyr Trp Ile Gly
1               5                   10

<210> SEQ ID NO 217
<211> LENGTH: 20
<212> TYPE: PRT
<213> ORGANISM: Artificial Sequence
<220> FEATURE:
<223> OTHER INFORMATION: XFT VH CDR2

<400> SEQUENCE: 217

Trp Met Gly Ile Ile Asp Pro Gly Asp Ser Arg Thr Arg Tyr Ser Pro
1               5                   10                  15

Ser Phe Gln Gly
            20

<210> SEQ ID NO 218
<211> LENGTH: 11
<212> TYPE: PRT
<213> ORGANISM: Artificial Sequence
<220> FEATURE:
<223> OTHER INFORMATION: XFT VH CDR3

<400> SEQUENCE: 218

Gly Gln Leu Tyr Gly Gly Thr Tyr Met Asp Gly
1               5                   10

<210> SEQ ID NO 219
<211> LENGTH: 14
<212> TYPE: PRT
<213> ORGANISM: Artificial Sequence
<220> FEATURE:
<223> OTHER INFORMATION: XFT VL CDR1
```

<400> SEQUENCE: 219

Thr Gly Thr Ser Ser Asp Ile Gly Gly Tyr Asn Ser Val Ser
1               5                   10

<210> SEQ ID NO 220
<211> LENGTH: 11
<212> TYPE: PRT
<213> ORGANISM: Artificial Sequence
<220> FEATURE:
<223> OTHER INFORMATION: XFT VL CDR2

<400> SEQUENCE: 220

Leu Met Ile Tyr Gly Val Asn Asn Arg Pro Ser
1               5                   10

<210> SEQ ID NO 221
<211> LENGTH: 10
<212> TYPE: PRT
<213> ORGANISM: Artificial Sequence
<220> FEATURE:
<223> OTHER INFORMATION: XFT VL CDR3

<400> SEQUENCE: 221

Ser Ser Tyr Asp Ile Glu Ser Ala Thr Pro
1               5                   10

<210> SEQ ID NO 222
<211> LENGTH: 449
<212> TYPE: PRT
<213> ORGANISM: Artificial Sequence
<220> FEATURE:
<223> OTHER INFORMATION: XFT Heavy Chain, terminal K
<220> FEATURE:
<221> NAME/KEY: MOD_RES
<222> LOCATION: (299)..(299)
<223> OTHER INFORMATION: Xaa is Asn297

<400> SEQUENCE: 222

Gln Val Glu Leu Val Gln Ser Gly Ala Val Lys Lys Pro Gly Glu Ser
1               5                   10                  15

Leu Lys Ile Ser Cys Lys Gly Ser Gly Tyr Ser Phe Thr Ser Tyr Trp
            20                  25                  30

Ile Gly Trp Val Arg Gln Ala Pro Gly Lys Gly Leu Glu Trp Met Gly
        35                  40                  45

Ile Ile Asp Pro Gly Asp Ser Arg Thr Arg Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Gly Gln Leu Tyr Gly Gly Thr Tyr Met Asp Gly Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Xaa Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 223
<211> LENGTH: 119
<212> TYPE: PRT
<213> ORGANISM: Artificial Sequence
<220> FEATURE:
<223> OTHER INFORMATION: X09 VH

<400> SEQUENCE: 223

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
            50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
```

-continued

```
                85                  90                  95

Ala Arg Gly Gly Tyr Asp Gly Arg Gly Phe Asp Tyr Trp Gly Ser Gly
            100                 105                 110

Thr Pro Val Thr Val Ser Ser
        115

<210> SEQ ID NO 224
<211> LENGTH: 106
<212> TYPE: PRT
<213> ORGANISM: Artificial Sequence
<220> FEATURE:
<223> OTHER INFORMATION: X09 VL

<400> SEQUENCE: 224

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
            100                 105

<210> SEQ ID NO 225
<211> LENGTH: 448
<212> TYPE: PRT
<213> ORGANISM: Artificial Sequence
<220> FEATURE:
<223> OTHER INFORMATION: X09 Heavy Chain
<220> FEATURE:
<221> NAME/KEY: MOD_RES
<222> LOCATION: (299)..(299)
<223> OTHER INFORMATION: Xaa is Asn297

<400> SEQUENCE: 225

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

-continued

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Xaa Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 226
<211> LENGTH: 213
<212> TYPE: PRT
<213> ORGANISM: Artificial Sequence
<220> FEATURE:
<223> OTHER INFORMATION: X09 Light Chain

<400> SEQUENCE: 226

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

-continued

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 227
<211> LENGTH: 5
<212> TYPE: PRT
<213> ORGANISM: Artificial Sequence
<220> FEATURE:
<223> OTHER INFORMATION: X09 VH CDR1

<400> SEQUENCE: 227

Gly Tyr Ser Phe Thr
1               5

<210> SEQ ID NO 228
<211> LENGTH: 17
<212> TYPE: PRT
<213> ORGANISM: Artificial Sequence
<220> FEATURE:
<223> OTHER INFORMATION: X09 VH CDR2

<400> SEQUENCE: 228

Leu Ile Thr Pro Tyr Asn Gly Ala Ser Ser Tyr Asn Gln Lys Phe Arg
1               5                   10                  15

Gly

<210> SEQ ID NO 229
<211> LENGTH: 10
<212> TYPE: PRT
<213> ORGANISM: Artificial Sequence
<220> FEATURE:
<223> OTHER INFORMATION: X09 VH CDR3

<400> SEQUENCE: 229

Gly Gly Tyr Asp Gly Arg Gly Phe Asp Tyr
1               5                   10

<210> SEQ ID NO 230
<211> LENGTH: 10
<212> TYPE: PRT
<213> ORGANISM: Artificial Sequence
<220> FEATURE:
<223> OTHER INFORMATION: X09 VL CDR1

<400> SEQUENCE: 230

Ser Ala Ser Ser Ser Val Ser Tyr Met His
1               5                   10

<210> SEQ ID NO 231
<211> LENGTH: 7
<212> TYPE: PRT
<213> ORGANISM: Artificial Sequence
<220> FEATURE:
<223> OTHER INFORMATION: X09 VL CDR2

<400> SEQUENCE: 231

Asp Thr Ser Lys Leu Ala Ser
1               5

<210> SEQ ID NO 232
<211> LENGTH: 9
<212> TYPE: PRT
<213> ORGANISM: Artificial Sequence
<220> FEATURE:
<223> OTHER INFORMATION: X09 VL CDR3

<400> SEQUENCE: 232

Gln Gln Trp Ser Lys His Pro Leu Thr
1               5

<210> SEQ ID NO 233
<211> LENGTH: 449
<212> TYPE: PRT
<213> ORGANISM: Artificial Sequence
<220> FEATURE:
<223> OTHER INFORMATION: X09 Heavy Chain, terminal K
<220> FEATURE:
<221> NAME/KEY: MOD_RES
<222> LOCATION: (299)..(299)
<223> OTHER INFORMATION: Xaa is Asn297

<400> SEQUENCE: 233

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
        50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Xaa Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 234
<211> LENGTH: 119
<212> TYPE: PRT
<213> ORGANISM: Artificial Sequence
<220> FEATURE:
<223> OTHER INFORMATION: X09.2 VH

<400> SEQUENCE: 234

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
```

```
                85                  90                  95
Ala Arg Gly Gly Tyr Asp Gly Arg Gly Phe Asp Tyr Trp Gly Gln Gly
                100                 105                 110

Thr Thr Val Thr Val Ser Ser
        115

<210> SEQ ID NO 235
<211> LENGTH: 106
<212> TYPE: PRT
<213> ORGANISM: Artificial Sequence
<220> FEATURE:
<223> OTHER INFORMATION: X09.2 VL

<400> SEQUENCE: 235

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Gly Tyr Pro Leu Thr
                85                  90                  95

Phe Gly Ala Gly Thr Lys Leu Glu Ile Lys
                100                 105

<210> SEQ ID NO 236
<211> LENGTH: 448
<212> TYPE: PRT
<213> ORGANISM: Artificial Sequence
<220> FEATURE:
<223> OTHER INFORMATION: X09.2 Heavy Chain
<220> FEATURE:
<221> NAME/KEY: MOD_RES
<222> LOCATION: (299)..(299)
<223> OTHER INFORMATION: Xaa is Asn297

<400> SEQUENCE: 236

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
        50                  55                  60

Arg Gly Lys Ala Thr Leu Thr Val Asp Lys Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
                100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Xaa Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 237
<211> LENGTH: 213
<212> TYPE: PRT
<213> ORGANISM: Artificial Sequence
<220> FEATURE:
<223> OTHER INFORMATION: X09.2 Light Chain

<400> SEQUENCE: 237

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60
```

```
Gly Ser Gly Asn Ser Tyr Ser Leu Thr Ile Ser Ser Val Glu Ala Glu
 65                  70                  75                  80

Asp Asp Ala Thr Tyr Tyr Cys Gln Gln Trp Ser Lys His Pro Leu Thr
                 85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 238
<211> LENGTH: 5
<212> TYPE: PRT
<213> ORGANISM: Artificial Sequence
<220> FEATURE:
<223> OTHER INFORMATION: X09.2 VH CDR1

<400> SEQUENCE: 238

Gly Tyr Thr Met Asn
1               5

<210> SEQ ID NO 239
<211> LENGTH: 17
<212> TYPE: PRT
<213> ORGANISM: Artificial Sequence
<220> FEATURE:
<223> OTHER INFORMATION: X09.2 VH CDR2

<400> SEQUENCE: 239

Leu Ile Thr Pro Tyr Asn Gly Ala Ser Ser Tyr Asn Gln Lys Phe Arg
1               5                   10                  15

Gly

<210> SEQ ID NO 240
<211> LENGTH: 10
<212> TYPE: PRT
<213> ORGANISM: Artificial Sequence
<220> FEATURE:
<223> OTHER INFORMATION: X09.2 VH CDR3

<400> SEQUENCE: 240

Gly Gly Tyr Asp Gly Arg Gly Phe Asp Tyr
1               5                   10

<210> SEQ ID NO 241
<211> LENGTH: 10
<212> TYPE: PRT
<213> ORGANISM: Artificial Sequence
<220> FEATURE:
<223> OTHER INFORMATION: X09.2 VL CDR1
```

```
<400> SEQUENCE: 241

Ser Ala Ser Ser Ser Val Ser Tyr Met His
1               5                   10

<210> SEQ ID NO 242
<211> LENGTH: 7
<212> TYPE: PRT
<213> ORGANISM: Artificial Sequence
<220> FEATURE:
<223> OTHER INFORMATION: X09.2 VL CDR2

<400> SEQUENCE: 242

Asp Thr Ser Lys Leu Ala Ser
1               5

<210> SEQ ID NO 243
<211> LENGTH: 9
<212> TYPE: PRT
<213> ORGANISM: Artificial Sequence
<220> FEATURE:
<223> OTHER INFORMATION: X09.2 VL CDR3

<400> SEQUENCE: 243

Gln Gln Trp Ser Gly Tyr Pro Leu Thr
1               5

<210> SEQ ID NO 244
<211> LENGTH: 449
<212> TYPE: PRT
<213> ORGANISM: Artificial Sequence
<220> FEATURE:
<223> OTHER INFORMATION: X09.2 Heavy Chain, terminal K
<220> FEATURE:
<221> NAME/KEY: MOD_RES
<222> LOCATION: (299)..(299)
<223> OTHER INFORMATION: Xaa is Asn297

<400> SEQUENCE: 244

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
        50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
                100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Xaa Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 245
<211> LENGTH: 630
<212> TYPE: PRT
<213> ORGANISM: Homo sapiens

<400> SEQUENCE: 245

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

-continued

```
Ser Thr Glu Gln Leu Arg Cys Leu Ala His Arg Leu Ser Glu Pro Pro
             100                 105                 110

Glu Asp Leu Asp Ala Leu Pro Leu Asp Leu Leu Phe Leu Asn Pro
         115                 120                 125

Asp Ala Phe Ser Gly Pro Gln Ala Cys Thr Arg Phe Phe Ser Arg Ile
     130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                 165                 170                 175

Leu Ser Glu Ala Asp Val Arg Ala Leu Gly Gly Leu Ala Cys Asp Leu
             180                 185                 190

Pro Gly Arg Phe Val Ala Glu Ser Ala Glu Val Leu Leu Pro Arg Leu
         195                 200                 205

Val Ser Cys Pro Gly Pro Leu Asp Gln Asp Gln Gln Glu Ala Ala Arg
     210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                 245                 250                 255

Gln Pro Ile Ile Arg Ser Ile Pro Gln Gly Ile Val Ala Ala Trp Arg
             260                 265                 270

Gln Arg Ser Ser Arg Asp Pro Ser Trp Arg Gln Pro Glu Arg Thr Ile
         275                 280                 285

Leu Arg Pro Arg Phe Arg Arg Glu Val Glu Lys Thr Ala Cys Pro Ser
     290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                 325                 330                 335

Asp Arg Val Asn Ala Ile Pro Phe Thr Tyr Glu Gln Leu Asp Val Leu
             340                 345                 350

Lys His Lys Leu Asp Glu Leu Tyr Pro Gln Gly Tyr Pro Glu Ser Val
         355                 360                 365

Ile Gln His Leu Gly Tyr Leu Phe Leu Lys Met Ser Pro Glu Asp Ile
     370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                 405                 410                 415

Pro Gln Val Ala Thr Leu Ile Asp Arg Phe Val Lys Gly Arg Gly Gln
             420                 425                 430

Leu Asp Lys Asp Thr Leu Asp Thr Leu Thr Ala Phe Tyr Pro Gly Tyr
         435                 440                 445

Leu Cys Ser Leu Ser Pro Glu Glu Leu Ser Ser Val Pro Pro Ser Ser
     450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                 485                 490                 495

Gly Ser Glu Tyr Phe Val Lys Ile Gln Ser Phe Leu Gly Gly Ala Pro
             500                 505                 510

Thr Glu Asp Leu Lys Ala Leu Ser Gln Gln Asn Val Ser Met Asp Leu
```

```
                515                 520                 525
Ala Thr Phe Met Lys Leu Arg Thr Asp Ala Val Leu Pro Leu Thr Val
    530                 535                 540
Ala Glu Val Gln Lys Leu Leu Gly Pro His Val Gly Leu Lys Ala
545                 550                 555                 560
Glu Glu Arg His Arg Pro Val Arg Asp Trp Ile Leu Arg Gln Arg Gln
                565                 570                 575
Asp Asp Leu Asp Thr Leu Gly Leu Gly Leu Gln Gly Gly Ile Pro Asn
                580                 585                 590
Gly Tyr Leu Val Leu Asp Leu Ser Met Gln Glu Ala Leu Ser Gly Thr
            595                 600                 605
Pro Cys Leu Leu Gly Pro Gly Pro Val Leu Thr Val Leu Ala Leu Leu
            610                 615                 620
Leu Ala Ser Thr Leu Ala
625                 630

<210> SEQ ID NO 246
<211> LENGTH: 622
<212> TYPE: PRT
<213> ORGANISM: Homo sapiens

<400> SEQUENCE: 246

Met Ala Leu Pro Thr Ala Arg Pro Leu Leu Gly Ser Cys Gly Thr Pro
1               5                   10                  15
Ala Leu Gly Ser Leu Leu Phe Leu Leu Phe Ser Leu Gly Trp Val Gln
                20                  25                  30
Pro Ser Arg Thr Leu Ala Gly Glu Thr Gly Gln Glu Ala Ala Pro Leu
            35                  40                  45
Asp Gly Val Leu Ala Asn Pro Pro Asn Ile Ser Ser Leu Ser Pro Arg
        50                  55                  60
Gln Leu Leu Gly Phe Pro Cys Ala Glu Val Ser Gly Leu Ser Thr Glu
65                  70                  75                  80
Arg Val Arg Glu Leu Ala Val Ala Leu Ala Gln Lys Asn Val Lys Leu
                85                  90                  95
Ser Thr Glu Gln Leu Arg Cys Leu Ala His Arg Leu Ser Glu Pro Pro
                100                 105                 110
Glu Asp Leu Asp Ala Leu Pro Leu Asp Leu Leu Leu Phe Leu Asn Pro
            115                 120                 125
Asp Ala Phe Ser Gly Pro Gln Ala Cys Thr Arg Phe Phe Ser Arg Ile
        130                 135                 140
Thr Lys Ala Asn Val Asp Leu Leu Pro Arg Gly Ala Pro Glu Arg Gln
145                 150                 155                 160
Arg Leu Leu Pro Ala Ala Leu Ala Cys Trp Gly Val Arg Gly Ser Leu
                165                 170                 175
Leu Ser Glu Ala Asp Val Arg Ala Leu Gly Gly Leu Ala Cys Asp Leu
                180                 185                 190
Pro Gly Arg Phe Val Ala Glu Ser Ala Glu Val Leu Leu Pro Arg Leu
            195                 200                 205
Val Ser Cys Pro Gly Pro Leu Asp Gln Asp Gln Gln Glu Ala Ala Arg
        210                 215                 220
Ala Ala Leu Gln Gly Gly Gly Pro Pro Tyr Gly Pro Pro Ser Thr Trp
225                 230                 235                 240
Ser Val Ser Thr Met Asp Ala Leu Arg Gly Leu Leu Pro Val Leu Gly
                245                 250                 255
```

-continued

```
Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
            275                 280                 285

Leu Arg Pro Arg Phe Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
    610                 615                 620
```

PYRROLOBENZODIAZEPINE-ANTIBODY CONJUGATES

CROSS-REFERENCE TO RELATED APPLICATIONS

This application is a national phase application under 35 U.S.C. § 371 of PCT International Application No. PCT/EP2018/053188, filed Feb. 8, 2018, which claims the benefit of Great Britain Application No. 1702031.4, filed 8 Feb. 8 2017, Great Britain Application No. 1719391.3, filed Nov. 22, 2017, Great Britain Application No. 1719398.8, filed Nov. 22, 2017, and Great Britain Application No. 1719393.9, filed Nov. 22, 2017, each of which is herein incorporated by reference.

FIELD OF THE INVENTION

The present invention relates to pyrrolobenzodiazepines (PBDs) having a labile protecting group in the form of a linker to an antibody.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiodcs*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

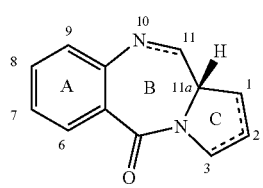

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Veriag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

One pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

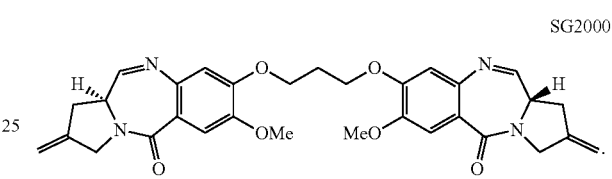

WO 2007/085930 describes the preparation of dimer PBD compounds having linker groups for connection to a cell binding agent, such as an antibody. The linker is present in the bridge linking the monomer PBD units of the dimer.

Dimer PBD compounds having linker groups for connection to a cell binding agent, such as an antibody, have been described in WO 2011/130613 and WO 2011/130616. The linker in these compounds is attached to the PBD core via the C2 position, and are generally cleaved by action of an enzyme on the linker group. In WO 2011/130598, the linker in these compounds is attached to one of the available N10 positions on the PBD core, and are generally cleaved by action of an enzyme on the linker group.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) *Expert. Opin. Biol. Ther.* 6(3):281-291; Kovtun et al (2006) *Cancer Res.* 66(6): 3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al (2003) *Cancer Immunol. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Doman et al (2009)

Blood 114(13):2721-2729; U.S. Pat. Nos. 7,521,541; 7,723, 485; WO2009/052249; McDonagh (2006) *Protein Eng. Design & Sel.* 19(7): 299-307; Doronina et al (2006) *Bioconj. Chem.* 17:114-124; Erickson et al (2006) *Cancer Res.* 66(8):1-8; Sanderson et al (2005) *Clin. Cancer Res.* 11:843-852; Jeffrey et al (2005) *J. Med. Chem.* 48:1344-1358; Hamblett et al (2004) *Clin. Cancer Res.* 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

The present inventors have developed particular PBD dimer antibody conjugates.

SUMMARY OF THE INVENTION

A first aspect of the present invention provides a conjugate of formula (I):

Ab-(DL)$_p$     (I)

wherein:
Ab is an antibody that binds to DLK1;
DL is (ib) $C_1$-5 saturated aliphatic alkyl;
(ic) $C_{3-6}$ saturated cycloalkyl;

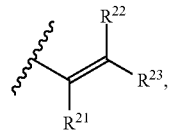
(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

[structure of DL]

wherein:
X is selected from the group comprising: a single bond, —CH$_2$— and —C$_2$H$_4$—;
n is from 1 to 8;
m is 0 or 1;
$R^7$ is either methyl or phenyl;
when there is a double bond between C2 and C3, $R^2$ is selected the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

wherein one of $R^{25a}$ and $R^{25b}$ is H and the other is selected from: phenyl, which phenyl is optionally substituted by a group selected from halo, methyl, methoxy; pyridyl; and thiophenyl; and

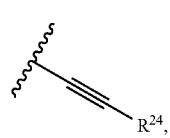
(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2 and C3, $R^2$ is

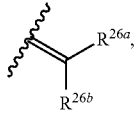

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester or, when one of $R^{26a}$ and $R^{26b}$ is H, the other is selected from nitrile and a $C_{1-4}$ alkyl ester;

when there is a double bond between C2' and C3', $R^{12}$ is selected the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

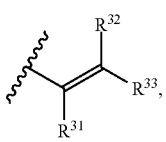

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

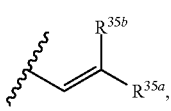

wherein one of $R^{35a}$ and $R^{35b}$ is H and the other is selected from: phenyl, which phenyl is optionally substituted by a group selected from halo, methyl, methoxy; pyridyl; and thiophenyl; and (if)

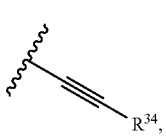

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2' and C3', $R^{12}$ is

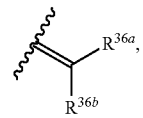

where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{36a}$ and $R^{36b}$ is H, the other is selected from nitrile and a $C_{1-4}$ alkyl ester;

and p is from 1 to 8.

A second aspect of the present invention provides a conjugate of formula (I):

Ab-(DL)p　　　　　(I)

wherein:

Ab is an antibody that binds to KAAG1; and

DL is as defined for the first aspect, above.

A third aspect of the present invention provides a conjugate of formula (I):

Ab-(DL)p　　　　　(I)

wherein:

Ab is an antibody that binds to Mesothelin; and

DL is as defined for the first aspect, above.

These conjugates have been found to exhibit good activity, and surprising tolerability compared to analogous conjugates not containing the sulfonamido moiety.

DETAILED DESCRIPTION OF THE INVENTION

Figure 1:
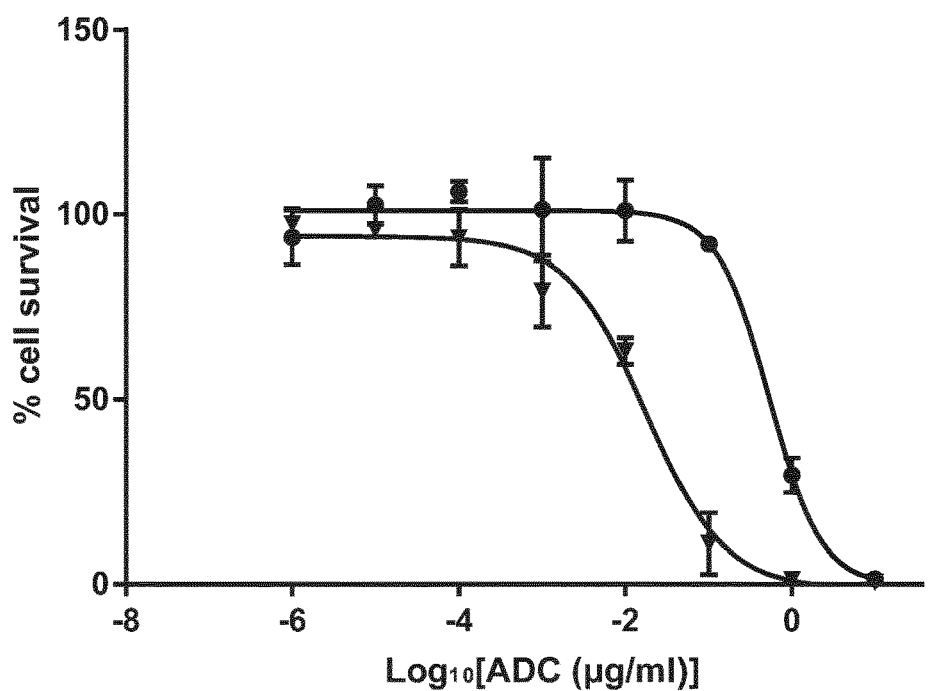
FIG. 1 shows the in vitro cytotoxicity of a conjugate according to the first aspect of the invention.
Figure 1:
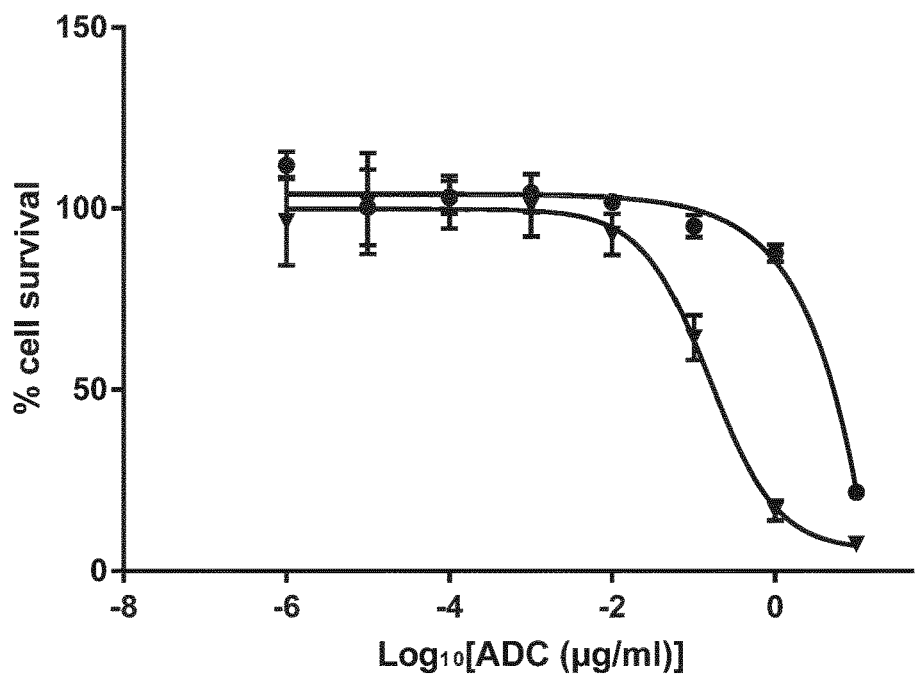

The present invention provides a PBD dimer with a linker connected through the N10 position on one of the PBD moieties conjugated to an antibody as defined below.

The present invention is suitable for use in providing a PBD compound to a preferred site in a subject. The conjugate allows the release of an active PBD compound that does not retain any part of the linker. There is no stub present that could affect the reactivity of the PBD compound. Thus the conjugate of formula (I) would release the compound RelA:

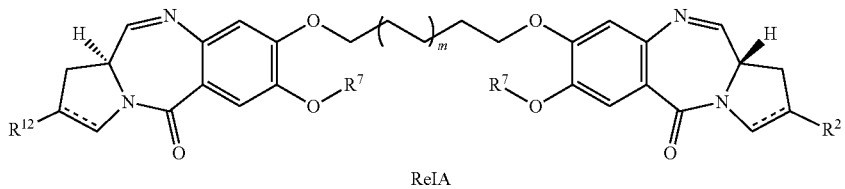

RelA

The specified link between the PBD dimer and the antibody in the present invention is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae RelA is achieved at the desired activation site of the conjugate of formula (I) by the action of an enzyme, such as cathepsin, on the linking group, and in particular on the valine-alanine dipeptide moiety.

Definition

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl (C5), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
saturated monocyclic hydrocarbon compounds:
cyclopropane $C_3$), cyclobutane $C_4$), cyclopentane (C5), cyclohexane (C6), cycloheptane ($C_7$), methylcyclopropene ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);
unsaturated monocyclic hydrocarbon compounds:
cyclopropene $C_3$), cyclobutene $C_4$), cyclopentene (C5), cyclohexene (C6), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and
saturated polycyclic hydrocarbon compounds:
norcarane $C_7$), norpinane $C_7$), norbornane $C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. C3-20, C3-7, 05-6, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane (C6);

$N_2$: imidazolidine ($C_5$), pyrazolidine (diazolidine) ($C_5$), imidazoline (C5), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_5$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_5$), pyrimidine (1,3-diazine) ($C_5$) (e.g., cytosine, thymine, uracil), pyrazine (1,4-diazine) ($C_6$);

$N_3$: triazole ($C_5$), triazine ($C_5$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

C11 (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu)

(n-butoxy), —O(sBu) (sec-butoxy), —O(iBu) (isobutoxy), and —O(tBu) (tert-butoxy).

Carboxy (carboxylic acid): —C(=O)OH.

Ester (carboxylate, carboxylic acid ester, oxycarbonyl): —C(=O)OR, wherein R is an ester substituent, for example, a C1-7 alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Nitro: —NO$_2$.

Azido: —N$_3$.

Cyano (nitrile, carbonitrile): —CN.

Antibody

Anti-DLK1

In one aspect the antibody is an antibody that binds to DLK1.

Delta-like 1 homolog protein (DLK-1) is an EGF-like membrane bound protein consisting of six tandem EGF-like repeats, a juxtamembrane region with a TACE (ADAM17)-mediated cleavage site, a transmembrane domain, and a short intracellular tail. DLK-1 is strongly expressed during fetal development, but its expression is turned down and highly restricted in adults. Conversely, DLK-1 gets re-expressed in several tumors, such as neuroblastoma, hepatocellular carcinoma (HCC), rhabdomyosarcoma, small cell lung cancer, myelodysplastic syndrome and acute myeloid leukemia. Interestingly, in HCC DLK-1 has been shown to be a marker of cancer stem cells, a subpopulation of cells responsible for tumor initiation, growth, metastasis, and recurrence.

Altogether, DLK-1 represents an attractive target for an antibody-drug conjugate (ADC) approach based on its selective expression in a wide range of malignancies and restricted expression in healthy organs, as well as its expression on HCC cancer stem cells.

HuBa-1-3d

In some embodiments the antibody comprises a VH domain having a VH CDR3 with the amino acid sequence of SEQ ID NO.7. In some embodiments the VH domain further comprises a VH CDR2 with the amino acid sequence of SEQ ID NO.6, and/or a VH CDR1 with the amino acid sequence of SEQ ID NO.5. In some embodiments the antibody comprises a VH domain having a VH CDR1 with the amino acid sequence of SEQ ID NO.5, a VH CDR2 with the amino acid sequence of SEQ ID NO.6, and a VH CDR3 with the amino acid sequence of SEQ ID NO.7. In preferred embodiments the antibody comprises a VH domain having the sequence according to SEQ ID NO. 1.

The antibody may further comprise a VL domain. In some embodiments the antibody comprises a VL domain having a VL CDR3 with the amino acid sequence of SEQ ID NO.10. In some embodiments the VL domain further comprises a VL CDR2 with the amino acid sequence of SEQ ID NO.9, and/or a VL CDR1 with the amino acid sequence of SEQ ID NO.8. In some embodiments the antibody comprises a VL domain having a VL CDR1 with the amino acid sequence of SEQ ID NO.8, a VL CDR2 with the amino acid sequence of SEQ ID NO.9, and a VL CDR3 with the amino acid sequence of SEQ ID NO.10. In preferred embodiments the antibody comprises a VL domain having the sequence according to SEQ ID NO. 2.

In preferred embodiments the antibody comprises a VH domain and a VL domain. Preferably the VH comprises the sequence of SEQ ID NO.1 and the VL domain comprises the sequence of SEQ ID NO.2.

The VH and VL domain(s) may pair so as to form an antibody antigen binding site that binds DLK1.

In some embodiments the antibody is an intact antibody comprising a VH domain paired with a VL domain, the VH and VL domains having sequences of SEQ ID NO.1 paired with SEQ ID NO.2.

In some embodiments the antibody comprises a heavy chain having the sequence of SEQ ID NO. 3 paired with a light chain having the sequence of SEQ ID NO.4. In some embodiments the antibody is an intact antibody comprising two heavy chains having the sequence of SEQ ID NO.3, each paired with a light chain having the sequence of SEQ ID NO.4.

In some embodiments the antibody comprises a heavy chain having the sequence of SEQ ID NO. 11 paired with a light chain having the sequence of SEQ ID NO.4. In some embodiments the antibody is an intact antibody comprising two heavy chains having the sequence of SEQ ID NO.11, each paired with a light chain having the sequence of SEQ ID NO.4.

In one aspect the antibody is an antibody as described herein which has been modified (or further modified) as described below. In some embodiments the antibody is a humanised, deimmunised or resurfaced version of an antibody disclosed herein.

Anti-KAAG1

In one aspect the antibody is an antibody that binds to KAAG1.

Antibody 3A4

In some embodiments the antibody comprises a VH domain having a VH CDR3 with the amino acid sequence of SEQ ID NO.107. In some embodiments the VH domain further comprises a VH CDR2 with the amino acid sequence of SEQ ID NO.106, and/or a VH CDR1 with the amino acid sequence of SEQ ID NO.105. In some embodiments the antibody comprises a VH domain having a VH CDR1 with the amino acid sequence of SEQ ID NO.105, a VH CDR2 with the amino acid sequence of SEQ ID NO.106, and a VH CDR3 with the amino acid sequence of SEQ ID NO.107. In preferred embodiments the antibody comprises a VH domain having the sequence according to SEQ ID NO. 101.

The antibody may further comprise a VL domain. In some embodiments the antibody comprises a VL domain having a VL CDR3 with the amino acid sequence of SEQ ID NO.110. In some embodiments the VL domain further comprises a VL CDR2 with the amino acid sequence of SEQ ID NO.109, and/or a VL CDR1 with the amino acid sequence of SEQ ID NO.108. In some embodiments the antibody comprises a VL domain having a VL CDR1 with the amino acid sequence of SEQ ID NO.108, a VL CDR2 with the amino acid sequence of SEQ ID NO.109, and a VL CDR3 with the amino acid sequence of SEQ ID NO.110. In preferred embodiments the antibody comprises a VL domain having the sequence according to SEQ ID NO. 102, SEQ ID NO.113, or SEQ ID NO.115.

In preferred embodiments the antibody comprises a VH domain and a VL domain. Preferably the VH comprises the sequence of SEQ ID NO.101 and the VL domain comprises the sequence of SEQ ID NO.102, SEQ ID NO.113, or SEQ ID NO.115.

The VH and VL domain(s) may pair so as to form an antibody antigen binding site that binds KAAG1.

In some embodiments the antibody is an intact antibody comprising a VH domain paired with a VL domain, the VH and VL domains having sequences of SEQ ID NO.101 paired with SEQ ID NO.102, SEQ ID NO.113, or SEQ ID NO.115.

In some embodiments the antibody comprises a heavy chain having the sequence of SEQ ID NO. 103 paired with a light chain having the sequence of SEQ ID NO.104, SEQ ID NO.114, or SEQ ID NO.116. In some embodiments the antibody is an intact antibody comprising two heavy chains having the sequence of SEQ ID NO.103, each paired with a light chain having the sequence of SEQ ID NO.104, SEQ ID NO.114, or SEQ ID NO.116.

In some embodiments the antibody comprises a heavy chain having the sequence of SEQ ID NO. 111 paired with a light chain having the sequence of SEQ ID NO.104, SEQ ID NO.114, or SEQ ID NO.116. In some embodiments the antibody is an intact antibody comprising two heavy chains having the sequence of SEQ ID NO.111, each paired with a light chain having the sequence of SEQ ID NO.104, SEQ ID NO.114, or SEQ ID NO.116.

In one aspect the antibody is an antibody as described herein which has been modified (or further modified) as described below. In some embodiments the antibody is a humanised, deimmunised or resurfaced version of an antibody disclosed herein.

Anti-Mesothelin

In one aspect the antibody is an antibody that binds to Mesothelin.

ADCT-XA4

In some embodiments the antibody comprises a VH domain having a VH CDR3 with the amino acid sequence of SEQ ID NO.207. In some embodiments the VH domain further comprises a VH CDR2 with the amino acid sequence of SEQ ID NO.206, and/or a VH CDR1 with the amino acid sequence of SEQ ID NO.205. In some embodiments the antibody comprises a VH domain having a VH CDR1 with the amino acid sequence of SEQ ID NO.205, a VH CDR2 with the amino acid sequence of SEQ ID NO.206, and a VH CDR3 with the amino acid sequence of SEQ ID NO.207. In preferred embodiments the antibody comprises a VH domain having the sequence according to SEQ ID NO. 201.

The antibody may further comprise a VL domain. In some embodiments the antibody comprises a VL domain having a VL CDR3 with the amino acid sequence of SEQ ID NO.210. In some embodiments the VL domain further comprises a VL CDR2 with the amino acid sequence of SEQ ID NO.209, and/or a VL CDR1 with the amino acid sequence of SEQ ID NO.208. In some embodiments the antibody comprises a VL domain having a VL CDR1 with the amino acid sequence of SEQ ID NO.208, a VL CDR2 with the amino acid sequence of SEQ ID NO.209, and a VL CDR3 with the amino acid sequence of SEQ ID NO.210. In preferred embodiments the antibody comprises a VL domain having the sequence according to SEQ ID NO. 202.

In preferred embodiments the antibody comprises a VH domain and a VL domain. Preferably the VH comprises the sequence of SEQ ID NO.201 and the VL domain comprises the sequence of SEQ ID NO.202.

The VH and VL domain(s) may pair so as to form an antibody antigen binding site that binds Mesothelin.

In some embodiments the antibody is an intact antibody comprising a VH domain paired with a VL domain, the VH and VL domains having sequences of SEQ ID NO.201 paired with SEQ ID NO.202.

In some embodiments the antibody comprises a heavy chain having the sequence of SEQ ID NO. 203 paired with a light chain having the sequence of SEQ ID NO.204. In some embodiments the antibody is an intact antibody comprising two heavy chains having the sequence of SEQ ID NO.203, each paired with a light chain having the sequence of SEQ ID NO.204.

In some embodiments the antibody comprises a heavy chain having the sequence of SEQ ID NO. 211 paired with a light chain having the sequence of SEQ ID NO.204. In some embodiments the antibody is an intact antibody comprising two heavy chains having the sequence of SEQ ID NO.211, each paired with a light chain having the sequence of SEQ ID NO.204.

ADCT-XFT

In some embodiments the antibody comprises a VH domain having a VH CDR3 with the amino acid sequence of SEQ ID NO.218. In some embodiments the VH domain further comprises a VH CDR2 with the amino acid sequence of SEQ ID NO.217, and/or a VH CDR1 with the amino acid sequence of SEQ ID NO.216. In some embodiments the antibody comprises a VH domain having a VH CDR1 with the amino acid sequence of SEQ ID NO.216, a VH CDR2 with the amino acid sequence of SEQ ID NO.217, and a VH CDR3 with the amino acid sequence of SEQ ID NO.218. In preferred embodiments the antibody comprises a VH domain having the sequence according to SEQ ID NO. 212.

The antibody may further comprise a VL domain. In some embodiments the antibody comprises a VL domain having a VL CDR3 with the amino acid sequence of SEQ ID NO.221. In some embodiments the VL domain further comprises a VL CDR2 with the amino acid sequence of SEQ ID NO.220, and/or a VL CDR1 with the amino acid sequence of SEQ ID NO.219. In some embodiments the antibody comprises a VL domain having a VL CDR1 with the amino acid sequence of SEQ ID NO.219, a VL CDR2 with the amino acid sequence of SEQ ID NO.220, and a VL CDR3 with the amino acid sequence of SEQ ID NO.221. In preferred embodiments the antibody comprises a VL domain having the sequence according to SEQ ID NO. 213.

In preferred embodiments the antibody comprises a VH domain and a VL domain. Preferably the VH comprises the sequence of SEQ ID NO.212 and the VL domain comprises the sequence of SEQ ID NO.213.

The VH and VL domain(s) may pair so as to form an antibody antigen binding site that binds Mesothelin.

In some embodiments the antibody is an intact antibody comprising a VH domain paired with a VL domain, the VH and VL domains having sequences of SEQ ID NO.212 paired with SEQ ID NO.213.

In some embodiments the antibody comprises a heavy chain having the sequence of SEQ ID NO. 214 paired with a light chain having the sequence of SEQ ID NO.215. In some embodiments the antibody is an intact antibody comprising two heavy chains having the sequence of SEQ ID NO.214, each paired with a light chain having the sequence of SEQ ID NO.215.

In some embodiments the antibody comprises a heavy chain having the sequence of SEQ ID NO. 222 paired with a light chain having the sequence of SEQ ID NO.215. In some embodiments the antibody is an intact antibody comprising two heavy chains having the sequence of SEQ ID NO.222, each paired with a light chain having the sequence of SEQ ID NO.215.

ADCT-X09

In some embodiments the antibody comprises a VH domain having a VH CDR3 with the amino acid sequence of SEQ ID NO.229. In some embodiments the VH domain further comprises a VH CDR2 with the amino acid sequence of SEQ ID NO.228, and/or a VH CDR1 with the amino acid sequence of SEQ ID NO.227. In some embodiments the antibody comprises a VH domain having a VH CDR1 with the amino acid sequence of SEQ ID NO.227, a VH CDR2 with the amino acid sequence of SEQ ID NO.228, and a VH CDR3 with the amino acid sequence of SEQ ID NO.229. In preferred embodiments the antibody comprises a VH domain having the sequence according to SEQ ID NO. 223.

The antibody may further comprise a VL domain. In some embodiments the antibody comprises a VL domain having a VL CDR3 with the amino acid sequence of SEQ ID NO.232. In some embodiments the VL domain further comprises a VL CDR2 with the amino acid sequence of SEQ ID NO.231, and/or a VL CDR1 with the amino acid sequence of SEQ ID NO.230. In some embodiments the antibody comprises a VL domain having a VL CDR1 with the amino acid sequence of SEQ ID NO.230, a VL CDR2 with the amino acid sequence of SEQ ID NO.231, and a VL CDR3 with the amino acid sequence of SEQ ID NO.232. In preferred embodiments the antibody comprises a VL domain having the sequence according to SEQ ID NO. 224.

In preferred embodiments the antibody comprises a VH domain and a VL domain. Preferably the VH comprises the sequence of SEQ ID NO.223 and the VL domain comprises the sequence of SEQ ID NO.224.

The VH and VL domain(s) may pair so as to form an antibody antigen binding site that binds Mesithelin.

In some embodiments the antibody is an intact antibody comprising a VH domain paired with a VL domain, the VH and VL domains having sequences of SEQ ID NO.223 paired with SEQ ID NO.224.

In some embodiments the antibody comprises a heavy chain having the sequence of SEQ ID NO. 225 paired with a light chain having the sequence of SEQ ID NO.226. In some embodiments the antibody is an intact antibody comprising two heavy chains having the sequence of SEQ ID NO.225, each paired with a light chain having the sequence of SEQ ID NO.226.

In some embodiments the antibody comprises a heavy chain having the sequence of SEQ ID NO. 233 paired with a light chain having the sequence of SEQ ID NO.226. In some embodiments the antibody is an intact antibody comprising two heavy chains having the sequence of SEQ ID NO.233, each paired with a light chain having the sequence of SEQ ID NO.226.

ADCT-X09.2

In some embodiments the antibody comprises a VH domain having a VH CDR3 with the amino acid sequence of SEQ ID NO.240. In some embodiments the VH domain further comprises a VH CDR2 with the amino acid sequence of SEQ ID NO.239, and/or a VH CDR1 with the amino acid sequence of SEQ ID NO.238. In some embodiments the antibody comprises a VH domain having a VH CDR1 with the amino acid sequence of SEQ ID NO.238, a VH CDR2 with the amino acid sequence of SEQ ID NO.239, and a VH CDR3 with the amino acid sequence of SEQ ID NO.240. In preferred embodiments the antibody comprises a VH domain having the sequence according to SEQ ID NO.234.

The antibody may further comprise a VL domain. In some embodiments the antibody comprises a VL domain having a VL CDR3 with the amino acid sequence of SEQ ID NO.243. In some embodiments the VL domain further comprises a VL CDR2 with the amino acid sequence of SEQ ID NO.242, and/or a VL CDR1 with the amino acid sequence of SEQ ID NO.241. In some embodiments the antibody comprises a VL domain having a VL CDR1 with the amino acid sequence of SEQ ID NO.241, a VL CDR2 with the amino acid sequence of SEQ ID NO.242, and a VL CDR3 with the amino acid sequence of SEQ ID NO.243. In preferred embodiments the antibody comprises a VL domain having the sequence according to SEQ ID NO. 235.

In preferred embodiments the antibody comprises a VH domain and a VL domain. Preferably the VH comprises the sequence of SEQ ID NO.234 and the VL domain comprises the sequence of SEQ ID NO.235.

The VH and VL domain(s) may pair so as to form an antibody antigen binding site that binds Mesothelin.

In some embodiments the antibody is an intact antibody comprising a VH domain paired with a VL domain, the VH and VL domains having sequences of SEQ ID NO.234 paired with SEQ ID NO.235.

In some embodiments the antibody comprises a heavy chain having the sequence of SEQ ID NO. 236 paired with a light chain having the sequence of SEQ ID NO.237. In some embodiments the antibody is an intact antibody comprising two heavy chains having the sequence of SEQ ID NO.236, each paired with a light chain having the sequence of SEQ ID NO.237.

In some embodiments the antibody comprises a heavy chain having the sequence of SEQ ID NO. 244 paired with a light chain having the sequence of SEQ ID NO.237. In some embodiments the antibody is an intact antibody comprising two heavy chains having the sequence of SEQ ID NO.244, each paired with a light chain having the sequence of SEQ ID NO.237.

Terminology

The term "antibody" herein is used in the broadest sense and specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind DLK1, KAAG1, or Mesothelin. Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2m1, A2m2, Km1, Km2 and Km3) of immunoglobulin molecule. The immunoglobulins can be derived from any species, including human, murine, or rabbit origin.

As used herein, "binds DLK1" is used to mean the antibody binds DLK1 with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds DLK1 with an association constant ($K_a$) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the invention can bind DLK1 with a high affinity. For example, in some embodiments the antibody can bind DLK1 with a $K_D$ equal to or less than about $10^{-6}$ M, such as $1\times10^{-6}$, $10^{-7}$, $10^{-8}$, $10^{-9}$, $10^{-10}$, $10^{-11}$, $10^{-12}$, $10^{-13}$ or $10^{-14}$.

DLK1 is member of the EGF-like family of homeotic proteins. In some embodiments, the DLK1 polypeptide corresponds to Genbank accession no. CAA78163, version no. CAA78163.1, record update date: Feb. 2, 2011 10:34 AM (SEQ ID NO.12). In one embodiment, the nucleic acid encoding DLK1 polypeptide corresponds to Genbank accession no. Z12172, version no Z12172.1, record update date: Feb. 2, 2011 10:34 AM. In some embodiments, the DLK1 polypeptide has the sequence of SEQ ID NO.13.

As used herein, "binds KAAG1" is used to mean the antibody binds KAAG1 with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds KAAG1 with an association constant ($K_a$) at least 2, 3, 4, 5, 10, 20, 50, 100, 200, 500, 1000, 2000, 5000, $10^4$, $10^5$ or $10^8$-fold higher than the antibody's association constant for BSA, when measured at physiological conditions. The antibodies of the invention can bind KAAG1 with a high affinity. For example, in some embodiments the antibody can bind KAAG1 with a $K_D$ equal to or less than about $10^{-6}$ M, such as $1\times10^{-6}$, $10^{-7}$, $10^{-8}$, $10^{-9}$, $10^{-10}$, $10^{-11}$, $10^{-12}$, $10^{-13}$ or $10^{-14}$.

KAAG1 (Kidney associated antigen 1) is expressed in testis and kidney, and, at lower levels, in urinary bladder and liver. It is expressed by a high proportion of tumors of various histologic origin, including melanomas, sarcomas and colorectal carcinomas. In some embodiments, the KAAG1 polypeptide corresponds to Genbank accession no. AAF23613, version no. AAF23613.1. In one embodiment, the nucleic acid encoding KAAG1 polypeptide corresponds to Genbank accession no. AF181722, version no AF181722.1. In some embodiments, the KAAG1 polypeptide has the sequence of SEQ ID NO.112.

As used herein, "binds Mesothelin" is used to mean the antibody binds Mesothelin with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds Mesothelin with an association constant ($K_a$) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the invention can bind Mesothelin with a high affinity. For example, in some embodiments the antibody can bind Mesothelin with a $K_D$ equal to or less than about $10^{-6}$ M, such as $1\times10^{-6}$, $10^{-7}$, $10^{-8}$, $10^{31\ 9}$, $10^{-10}$, $10^{-11}$, $10^{-12}$, $10^{31\ 13}$ or $10^{-14}$.

Mesothelin is a 40 kDa protein present on normal mesothelial cells. The mesothelin gene encodes a precursor protein that is processed to yield mesothelin, which is attached to the cell membrane by a glycophosphatidylinositol linkage, and a 31-kDa shed fragment named megakaryocyte-potentiating factor (MPF). It has been proposed that mesothelin may be involved in cell adhesion. In some embodiments, the Mesothelin polypeptide corresponds to Genbank accession no. AAC50348, version no. AAC50348.1, record update date: Jun. 23, 2010 09:12 AM. In one embodiment, the nucleic acid encoding Mesothelin polypeptide corresponds to Genbank accession no. U40434, version no U40434.1, record update date: Jun. 23, 2010 09:12 AM. In some embodiments, the Mesothelin polypeptide has the sequence of SEQ ID NO.245. In some embodiments, the Mesothelin polypeptide has the sequence of SEQ ID NO.246.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al. (1991) Nature, 352:624-628; Marks et al. (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Modification of Antibodies

The antibodies disclosed herein may be modified. For example, to make them less immunogenic to a human subject. This may be achieved using any of a number of techniques familiar to the person skilled in the art. Some of these techniques are described in more detail below.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as Veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted at www.wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;
(c) defining for the non-human antibody to be humanized, a set of heavy and light chain surface exposed amino acid residues using the set of framework positions generated in step (b);
(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;
(e) substituting, in the amino acid sequence of the non-human antibody to be humanized, the set of heavy and light chain surface exposed amino acid residues defined in step (c) with the set of heavy and light chain surface exposed amino acid residues identified in step (d);
(f) constructing a three-dimensional model of the variable region of the non-human antibody resulting from the substituting specified in step (e);
(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and
(h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in *Methods* 36, 43-60 (2005).

Modification of Antibody with Azide

The antibody may prepared for conjugation with the drug linker through a three step process:
(1) Expression of antibody (Ab) bearing the core N-glycan in a suitable expression system (e.g. a CHO cell line). The core N-glycan is typically conjugated to Asn-297 of the heavy chain according to the numbering system of Kabat;
(2) trimming of all glycan isoforms (complex, hybrid, high-mannose) with an endoglycosidase to leave the core GlcNAc; and
(3) enzymatic transfer to the core GlcNAc of a N-acetylgalactose residue harboring an azide group for conjugation to the drug linker.

An overview of the above process is set out in van Geel, R., et al., Bioconjugate Chemistry, 2015, 26, 2233-2242; DOI: 10.1021/acs.bioconjchem.5b00224. Alternatively, a one-pot process may be used—see the examples.

Embodiments

X

In some embodiments, X is a single bond.
In other embodiments, X is —CH$_2$—.
In further embodiments, X is —C$_2$H$_4$—.
In some embodiments, n is 1 to 4.
In some of these embodiments, n is 1.
In other of these embodiments, n is 2.
In further of these embodiments, n is 4.

R$^7$

In one embodiment, R$^7$ is methyl.
In another embodiment, R$^7$ is phenyl.

R$^2$

When there is a double bond present between C2 and C3, R$^2$ is selected from: (a) C$_{5-10}$ aryl group, optionally substituted by one or more substituents selected from the group comprising: halo, nitro, cyano, ether, C$_{1-7}$ alkyl, C$_{3-7}$ heterocyclyl and bis-oxy-C$_{1-3}$ alkylene;
(b) C$_{1-5}$ saturated aliphatic alkyl;
(c) C$_{3-6}$ saturated cycloalkyl;

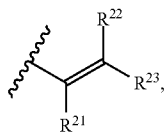
(d)

wherein each of R$^{21}$, R$^{22}$ and R$^{23}$ are independently selected from H, C$_{1-3}$ saturated alkyl, C$_{2-3}$ alkenyl, C$_{2-3}$ alkynyl and cyclopropyl, where the total number of carbon atoms in the R$^2$ group is no more than 5;

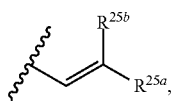
(e)

wherein one of R$^{25a}$ and R$^{25b}$ is H and the other is selected from: phenyl, which phenyl is optionally substituted by a group selected from halo methyl, methoxy; pyridyl; and thiophenyl; and

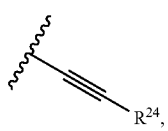
(f)

where R$^{24}$ is selected from: H; C$_{1-3}$ saturated alkyl; C$_{2-3}$ alkenyl; C$_{2-3}$ alkynyl; cyclopropyl; phenyl, which phenyl is optionally substituted by a group selected from halo methyl, methoxy; pyridyl; and thiophenyl.

When R$^2$ is a C$_{5-10}$ aryl group, it may be a C$_{5-7}$ aryl group. A C$_{5-7}$ aryl group may be a phenyl group or a C$_{5-7}$ heteroaryl group, for example furanyl, thiophenyl and pyridyl. In some embodiments, R$^2$ is preferably phenyl. In other embodiments, R$^{12}$ is preferably thiophenyl, for example, thiophen-2-yl and thiophen-3-yl.

When R$^2$ is a C$_{5-10}$ aryl group, it may be a C$_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When R$^2$ is a C$_{5-10}$ aryl group, it may bear any number of substituent groups. It preferably bears from 1 to 3 substituent groups, with 1 and 2 being more preferred, and singly substituted groups being most preferred. The substituents may be any position.

Where R$^2$ is C$_{5-7}$ aryl group, a single substituent is preferably on a ring atom that is not adjacent the bond to the remainder of the compound, i.e. it is preferably β or γ to the bond to the remainder of the compound. Therefore, where the C$_{5-7}$ aryl group is phenyl, the substituent is preferably in the meta- or para-positions, and more preferably is in the para-position.

Where R$^2$ is a C$_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

R$^2$ substituents, when R$^2$ is a C$_{5-10}$ aryl group

If a substituent on R$^2$ when R$^2$ is a C$_{5-10}$ aryl group is halo, it is preferably F or Cl, more preferably Cl.

If a substituent on R$^2$ when R$^2$ is a C$_{5-10}$ aryl group is ether, it may in some embodiments be an alkoxy group, for example, a C$_{1-7}$ alkoxy group (e.g. methoxy, ethoxy) or it may in some embodiments be a C$_{5-7}$ aryloxy group (e.g. phenoxy, pyridyloxy, furanyloxy). The alkoxy group may itself be further substituted, for example by an amino group (e.g. dimethylamino).

If a substituent on R$^2$ when R$^2$ is a C$_{5-10}$ aryl group is C$_{1-7}$ alkyl, it may preferably be a C$_{1-4}$ alkyl group (e.g. methyl, ethyl, propryl, butyl).

If a substituent on R$^2$ when R$^2$ is a C$_{5-10}$ aryl group is C$_{3-7}$ heterocyclyl, it may in some embodiments be C$_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by C$_{1-4}$ alkyl groups. If the C$_6$ nitrogen containing heterocyclyl group is piperazinyl, the said further substituent may be on the second nitrogen ring atom.

If a substituent on R$^2$ when R$^2$ is a C5-10 aryl group is bis-oxy-C$_{1-3}$ alkylene, this is preferably bis-oxy-methylene or bis-oxy-ethylene.

If a substituent on R$^2$ when R$^2$ is a C$_{5-10}$ aryl group is ester, this is preferably methyl ester or ethyl ester.

Particularly preferred substituents when R$^2$ is a C5-10 aryl group include methoxy, ethoxy, fluoro, chloro, cyano, bis-oxy-methylene, methyl-piperazinyl, morpholino and methyl-thiophenyl. Other particularly preferred substituent for R$^2$ are dimethylaminopropyloxy and carboxy.

Particularly preferred substituted $R^2$ groups when $R^2$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^2$ group is 4-nitrophenyl. $R^2$ groups of particular interest include 4-(4-methylpiperazin-1-yl)phenyl and 3,4-bisoxymethylene-phenyl.

When $R^2$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^2$ is $C_{3-6}$ saturated cycloalkyl, it may be cyclopropyl, cyclobutyl, cyclopentyl or cyclohexyl. In some embodiments, it may be cyclopropyl.

When $R^2$ is

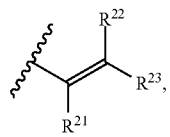

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5. In some embodiments, the total number of carbon atoms in the $R^2$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that are not H are methyl.

In some embodiments, $R^{21}$ is H.

In some embodiments, $R^{22}$ is H.

In some embodiments, $R^{23}$ is H.

In some embodiments, $R^{21}$ and $R^{22}$ are H.

In some embodiments, $R^{21}$ and $R^{23}$ are H.

In some embodiments, $R^{22}$ and $R^{23}$ are H.

A $R^2$ group of particular interest is:

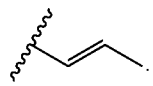

When $R^2$ is

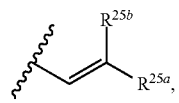

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^2$ is

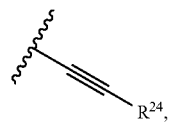

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

When there is a single bond present between C2 and C3, $R^2$ is

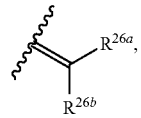

where $R^{26a}$ and $R^{26b}$ are independently selected from H, F, C1-4 saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a C1-4 alkyl ester.

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

R$^{12}$

The above preferences for R$^2$ apply equally to R$^{12}$.

In one embodiment of the invention, DL is or linker reagent relative to antibody, and (ii) limiting the conjugation reaction time or temperature.

Where more than one nucleophilic or electrophilic group of the antibody reacts with a drug-linker intermediate, or linker reagent followed by drug moiety reagent, then the

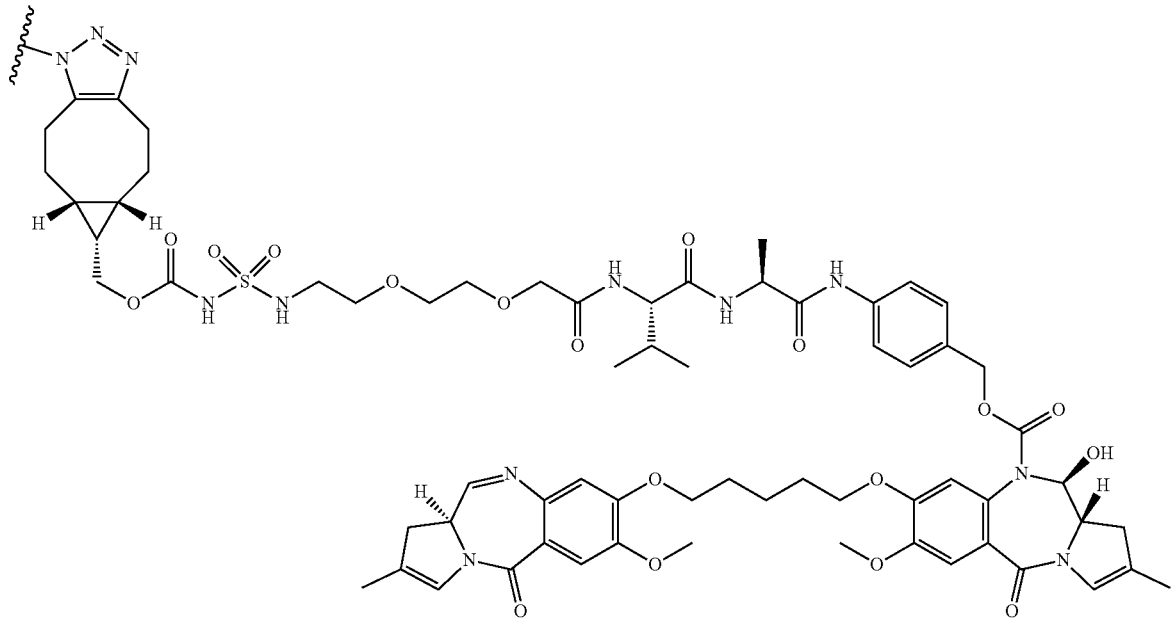 [SMILES: *n1nnc2c1CC[C@@H]1[C@H](CC2)[C@@H]1COC(=O)NS(=O)(=O)NCCOCCOCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4C=N5)c(OC)cc3C(=O)N3C=C(C)C[C@H]3[C@@H]2O)cc1)C(C)C]

Drug Loading

The drug loading is the average number of PBD drugs per antibody, e.g. antibody.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblen et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For the present antibody-drug conjugates, p is limited by the number of attachment sites on the antibody, i.e. the number of azide groups. For example, the antibody may have only one or two azide groups to which the drug linker may be attached.

Typically, fewer than the theoretical maximum of drug moieties are conjugated to an antibody during a conjugation reaction. The loading (drug/antibody ratio) of an ADC may be controlled in several different manners, including: (i) limiting the molar excess of drug-linker intermediate (D-L)

resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per antibody is in the range 1 to 8. In some embodiments the range is selected from 1 to 4, 1 to 4, 2 to 4, and 1 to 3.

In some embodiments, there are one or two dimer pyrrolobenzodiazepine groups per antibody.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—H$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{+3}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol ($R^AOH$, where $R^A$ is $C_{1-4}$ alkyl):

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized

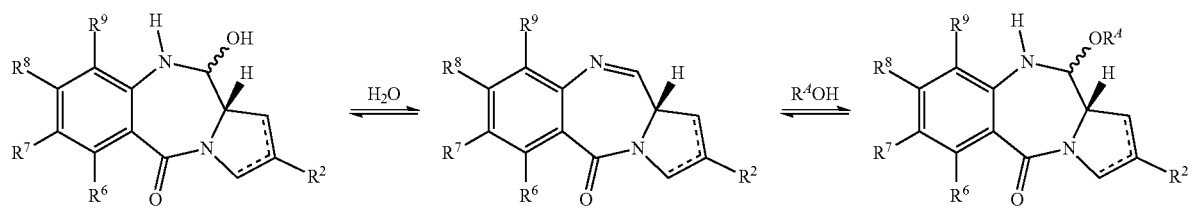

light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

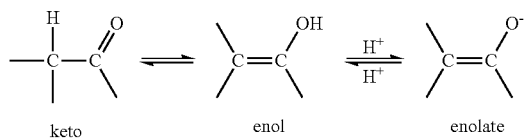

keto    enol    enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as $^3$H, $^{13}$C, and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity

In Vitro Cell Proliferation Assays

Generally, the cytotoxic or cytostatic activity of an antibody-drug conjugate (ADC) is measured by: exposing mammalian cells having receptor proteins to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay is conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 µl per well) into black 96 well plates. Plates of adherent cell lines are incubated overnight to allow adherence. Suspension cell cultures can be used on the day of seeding.

A stock solution (1 ml) of ADC (20 µg/ml) is made in the appropriate cell culture medium. Serial 10-fold dilutions of stock ADC are made in 15 ml centrifuge tubes by serially transferring 100 µl to 900 µl of cell culture medium.

Four replicate wells of each ADC dilution (100 µl) are dispensed in 96-well black plates, previously plated with cell suspension (100 µl), resulting in a final volume of 200 µl. Control wells receive cell culture medium (100 µl).

If the doubling time of the cell line is greater than 30 hours, ADC incubation is for 5 days, otherwise a four day incubation is done.

At the end of the incubation period, cell viability is assessed with the Alamar blue assay. AlamarBlue (Invitrogen) is dispensed over the whole plate (20 µl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

Use

The conjugates of the invention may be used to provide a PBD compound at a target location.

The target location is preferably a proliferative cell population. The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound RelA. Thus, the conjugate may be used to selectively provide a compound RelA to the target location.

The linker may be cleaved by an enzyme present at the target location.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Anti-DLK-1 Conjugates

Examples of proliferative conditions include, but are not limited to, benign, pre-malignant, and malignant cellular proliferation, including but not limited to, neoplasms and tumours (e.g.

histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to cancers, including metastatic cancers and metastatic cancer cells, such as circulating tumour cells, which may be found circulating in body fluids such as blood or lymph. Cancers of particular interest include: Hepatocellular carcinoma, hepatoblastoma, non small cell lung cancer, small cell lung cancer, colon cancer, breast cancer, gastric cancer, pancreatic cancer, neuroblastoma, adrenal gland cancer, pheochromocytoma, paraganglioma, thyroid medullary carcinoma, skeletal muscle cancer, liposarcoma, glioma, Wilms tumor, neuroendocrine tumors, Acute Myeloid Leukemia and Myelodysplastic syndrome.

Other disorders of interest include any condition in which DLK1 is overexpressed, or wherein DLK1 antagonism will provide a clinical benefit. These include immune disorders, cardiovascular disorders, thrombosis, diabetes, immune checkpoint disorders, fibrotic disorders (fibrosis), or proliferative diseases such as cancer, particularly metastatic cancer.

Anti-KAAG1 Conjugates

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to cancers, including metastatic cancers and metastatic cancer cells, such as circulating tumour cells, which may be found circulating in body fluids such as blood or lymph. Cancers of particular interest include ovarian, breast, prostate and renal cancer.

Other disorders of interest include any condition in which KAAG1 is overexpressed, or wherein KAAG1 antagonism will provide a clinical benefit. These include immune disorders, cardiovascular disorders, thrombosis, diabetes, immune checkpoint disorders, fibrotic disorders (fibrosis), or proliferative diseases such as cancer, particularly metastatic cancer.

Anti-Mesothelin Conjugates

Examples of proliferative conditions include, but are not limited to, benign, pre malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to cancers, including metastatic cancers and metastatic cancer cells, such as circulating tumour cells, which may be found circulating in body fluids such as blood or lymph. Cancers of particular interest include mesothelioma, lung cancer, ovarian cancer and pancreatic cancer.

Other disorders of interest include any condition in which Mesothelin is overexpressed, or wherein Mesothelin antagonism will provide a clinical benefit. These include immune disorders, cardiovascular disorders, thrombosis, diabetes, immune checkpoint disorders, fibrotic disorders (fibrosis), or proliferative diseases such as cancer, particularly metastatic cancer.

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine;

pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatrexate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, lmclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Drug Conjugates

The antibody drug conjugates of the present invention may be prepared by conjugating the following drug linker:

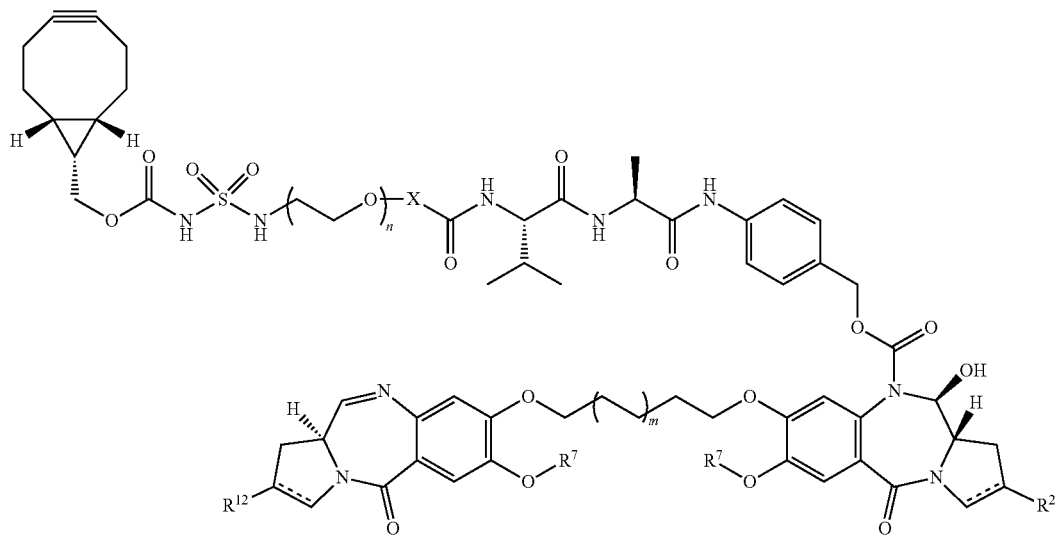

to the azide-containing antibody by the methods as described in for example, van Geel, R., et al., Bioconjugate Chemistry, 2015, 26, 2233-2242; DOI: 10.1021/acs.bioconjchem.5b00224. Suitable methods include, but are not limited to, copper-free conjugation, in for example, aqueous conditions with an optional cosolvent selected from DMF, DMSO and DMA.

The drug linker may be synthesised in accordance with the examples, with appropriate modifications, for example, referring to WO 2016/053107 for synthesis of the linker and the following documents for the PBD dimer, for example: WO 2011/130598, WO2013/055987, WO2014/057074.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

STATEMENTS OF INVENTION

The following numbered statements describe some specifically envisioned combinations of the present invention.

Anti-DLK1 Conjugates 1. A conjugate of formula (I):

Ab-(DL)$_p$ (I)

wherein:
Ab is an antibody that binds to DLK1;
DL is wherein:
X is selected from the group comprising: a single bond, —CH$_2$— and —C$_2$H$_4$—;
n is from 1 to 8;
m is 0 or 1;
R$^7$ is either methyl or phenyl;
when there is a double bond between C2 and C3, R$^2$ is selected the group consisting of:

(ia) C$_{5-10}$ aryl group, optionally substituted by one or more substituents selected from the group comprising: halo, nitro, cyano, ether, carboxy, ester, C$_{1-7}$ alkyl, C$_{3-7}$ heterocyclyl and bis-oxy-C$_{1-3}$ alkylene;
(ib) C$_{1-5}$ saturated aliphatic alkyl;
(ic) C$_{3-6}$ saturated cycloalkyl;

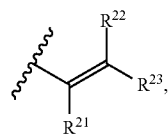

(id)

wherein each of R$^{21}$, R$^{22}$ and R$^{23}$ are independently selected from H, C$_{1-3}$ saturated alkyl, C$_{2-3}$ alkenyl, C$_{2-3}$ alkynyl and cyclopropyl, where the total number of carbon atoms in the R$^2$ group is no more than 5;

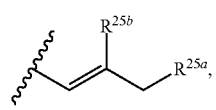

(ie)

wherein one of R$^{25a}$ and R$^{25b}$ is H and the other is selected from: phenyl, which phenyl is optionally substituted by a group selected from halo, methyl, methoxy; pyridyl; and thiophenyl; and

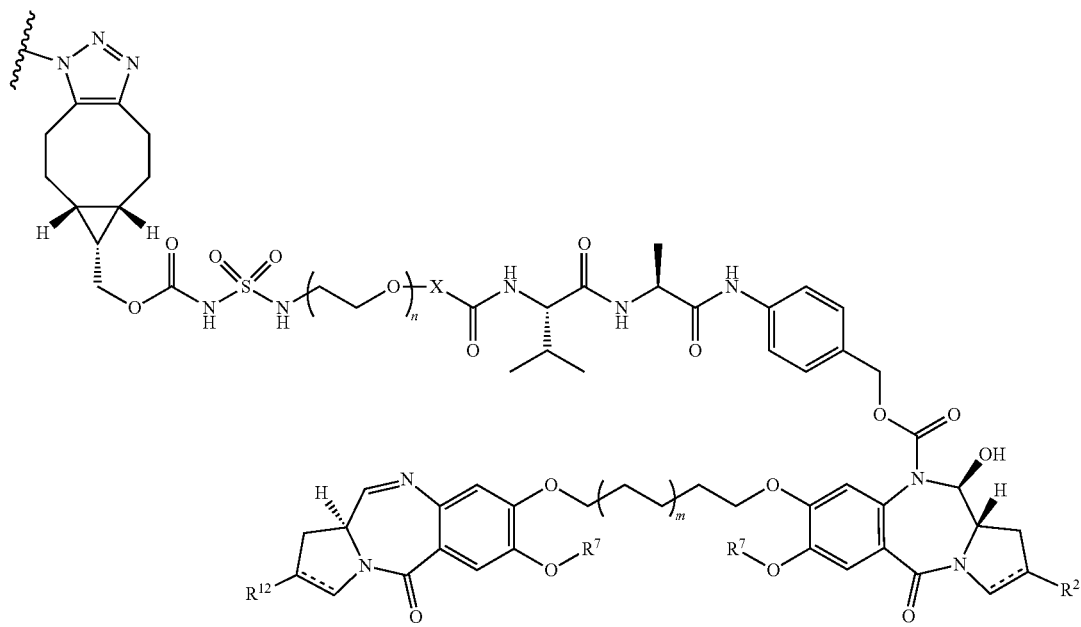

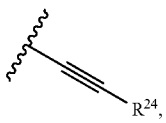
(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2 and C3, $R^2$ is

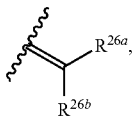

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

when there is a double bond between C2' and C3', $R^{12}$ is selected the group consisting of:

(iia) $C_{5-10}$ aryl group, optionally substituted by one or more substituents selected from the group comprising: halo, nitro, cyano, ether, carboxy, ester, $C_{1-7}$ alkyl, $C_3$-7 heterocyclyl and bis-oxy-$C_{1-3}$ alkylene;

(iib) $C_{1-5}$ saturated aliphatic alkyl;

(iic) $C_{3-6}$ saturated cycloalkyl;

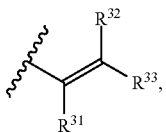
(iid)

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

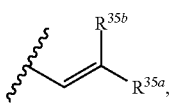
(iie)

wherein one of $R^{35a}$ and $R^{35b}$ is H and the other is selected from: phenyl, which phenyl is optionally substituted by a group selected from halo, methyl, methoxy; pyridyl; and thiophenyl; and

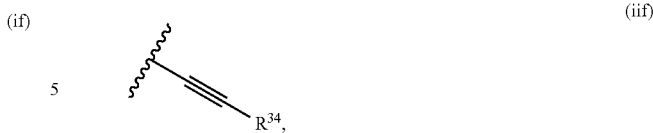
(iif)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2' and C3', $R^{12}$ is

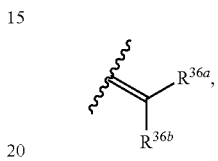

where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{36a}$ and $R^{36b}$ is H, the other is selected from nitrile and a $C_{1-4}$ alkyl ester; and p is from 1 to 8.

2. The conjugate according to statement 1, wherein X is a single bond.

3. The conjugate according to statement 1, wherein X is —CH$_2$—.

4. The conjugate according to statement 1, wherein X is —C$_2$H$_4$—.

5. The conjugate according to any one of statements 1 to 4, wherein n is 1 to 4.

6. The conjugate according to statement 5, wherein n is 1.

7. The conjugate according to statement 5, wherein n is 2.

8. The conjugate according to statement 5, wherein n is 4.

9. A compound according to any one of statements 1 to 8, wherein there is a double bond between C2 and C3, and $R^2$ is a C5-7 aryl group.

10. A compound according to statement 9, wherein $R^2$ is phenyl.

11. A compound according to any one of statements 1 to 8, wherein there is a double bond between C2 and C3, and $R^2$ is a $C_{8-10}$ aryl group.

12. A compound according to any one of statements 9 to 11, wherein $R^2$ bears one to three substituent groups.

13. A compound according to any one of statements 9 to 12, wherein the substituents are selected from methoxy, ethoxy, fluoro, chloro, cyano, bis-oxy-methylene, methyl-piperazinyl, morpholino and methyl-thiophenyl.

14. A compound according to any one of statements 1 to 8, wherein there is a double bond between C2 and C3, and $R^2$ is a $C_{1-5}$ saturated aliphatic alkyl group.

15. A compound according to statement 14, wherein $R^2$ is methyl, ethyl or propyl.

16. A compound according to any one of statements 1 to 8, wherein there is a double bond between C2 and C3, and $R^2$ is a $C_{3-6}$ saturated cycloalkyl group.

17. A compound according to statement 16, wherein $R^2$ is cyclopropyl.

18. A compound according to any one of statements 1 to 8, wherein there is a double bond between C2 and C3, and $R^2$ is a group of formula:

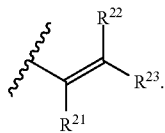

19. A compound according to statement 18, wherein the total number of carbon atoms in the $R^2$ group is no more than 4.

20. A compound according to statement 19, wherein the total number of carbon atoms in the $R^2$ group is no more than 3.

21. A compound according to any one of statements 18 to 20, wherein one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

22. A compound according to any one of statements 18 to 20, wherein two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

23. A compound according to any one of statements 1 to 8, wherein there is a double bond between $C_2$ and C3, and $R^2$ is a group of formula:

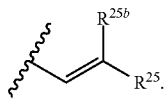

24. A compound according to statement 23, wherein $R^2$ is the group:

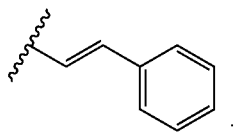 [SMILES: */C=C/c1ccccc1]

25. A compound according to any one of statements 1 to 8, wherein there is a double bond between C2 and C3, and $R^2$ is a group of formula:

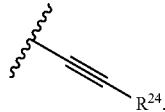

26. A compound according to statement 25, wherein $R^{24}$ is selected from H, methyl, ethyl, ethenyl and ethynyl.

27. A compound according to statement 26, wherein $R^{24}$ is selected from H and methyl.

28. A compound according to any one of statements 1 to 8, wherein there is a single bond between C2 and C3, $R^2$ is

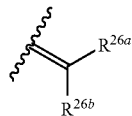

and $R^{26a}$ and $R^{26b}$ are both H.

29. A compound according to any one of statements 1 to 8, wherein there is a single bond between C2 and C3, $R^2$ is

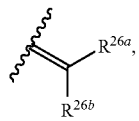

and $R^{26a}$ and $R^{26b}$ are both methyl.

30. A compound according to any one of statements 1 to 8, wherein there is a single bond between C2 and C3, $R^2$ is

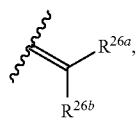

one of $R^{26a}$ and $R^{26b}$ is H, and the other is selected from $C_{1-4}$ saturated alkyl, $C_{2-3}$ alkenyl, which alkyl and alkenyl groups are optionally substituted.

31. A compound according to any one of statements 1 to 30, wherein there is a double bond between C2' and C3', and $R^{12}$ is a C5-7 aryl group.

32. A compound according to statement 31, wherein $R^{12}$ is phenyl.

33. A compound according to any one of statements 1 to 30, wherein there is a double bond between C2' and C3', and $R^{12}$ is a $C_{8-10}$ aryl group.

34. A compound according to any one of statements 31 to 33, wherein $R^{12}$ bears one to three substituent groups.

35. A compound according to any one of statements 31 to 34, wherein the substituents are selected from methoxy, ethoxy, fluoro, chloro, cyano, bis-oxy-methylene, methyl-piperazinyl, morpholino and methyl-thiophenyl.

36. A compound according to any one of statements 1 to 30, wherein there is a double bond between C2' and C3', and $R^{12}$ is a $C_{1-5}$ saturated aliphatic alkyl group.

37. A compound according to statement 36, wherein $R^{12}$ is methyl, ethyl or propyl.

38. A compound according to any one of statements 1 to 30, wherein there is a double bond between C2' and C3', and $R^{12}$ is a $C_{3-6}$ saturated cycloalkyl group.

39. A compound according to statement 38, wherein $R^{12}$ is cyclopropyl.

40. A compound according to any one of statements 1 to 30, wherein there is a double bond between C2' and C3', and $R^{12}$ is a group of formula:

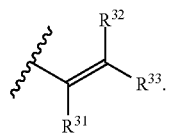

41. A compound according to statement 40, wherein the total number of carbon atoms in the $R^{12}$ group is no more than 4.

42. A compound according to statement 41, wherein the total number of carbon atoms in the $R^{12}$ group is no more than 3.

43. A compound according to any one of statements 40 to 42, wherein one of $R^{31}$, $R^{32}$ and $R^{33}$ is H, with the other two groups being selected from H, $C_{1-3}$ saturated alkyl, $C_{2-3}$ alkenyl, $C_{2-3}$ alkynyl and cyclopropyl.

44. A compound according to any one of statements 40 to 42, wherein two of $R^{31}$, $R^{32}$ and $R^{33}$ are H, with the other group being selected from H, $C_{1-3}$ saturated alkyl, $C_{2-3}$ alkenyl, $C_{2-3}$ alkynyl and cyclopropyl.

45. A compound according to any one of statements 1 to 30, wherein there is a double bond between C2' and C3', and $R^{12}$ is a group of formula:

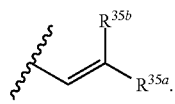

46. A compound according to statement 45, wherein $R^{12}$ is the group:

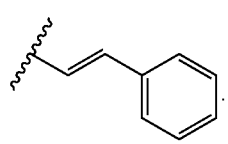 [SMILES: */C=C/c1ccccc1]

47. A compound according to any one of statements 1 to 30, wherein there is a double bond between C2' and C3', and $R^{12}$ is a group of formula:

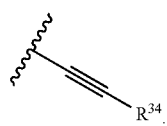

48. A compound according to statement 47, wherein $R^{34}$ is selected from H, methyl, ethyl, ethenyl and ethynyl.

49. A compound according to statement 48, wherein $R^{34}$ is selected from H and methyl.

50. A compound according to any one of statements 1 to 30, wherein there is a single bond between C2' and C3', $R^{12}$ is

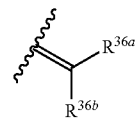

and $R^{36a}$ and $R^{36b}$ are both H.

51. A compound according to any one of statements 1 to 30, wherein there is a single bond between C2' and C3', $R^{12}$ is

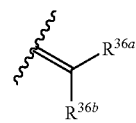

and $R^{36a}$ and $R^{36b}$ are both methyl.

52. A compound according to any one of statements 1 to 30, wherein there is a single bond between C2' and C3', $R^{12}$ is

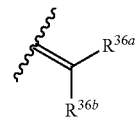

one of $R^{36a}$ and $R^{36b}$ is H, and the other is selected from $C_{1-4}$ saturated alkyl, $C_{2-3}$ alkenyl, which alkyl and alkenyl groups are optionally substituted.

53. A conjugate according to statement 1, wherein DL is:

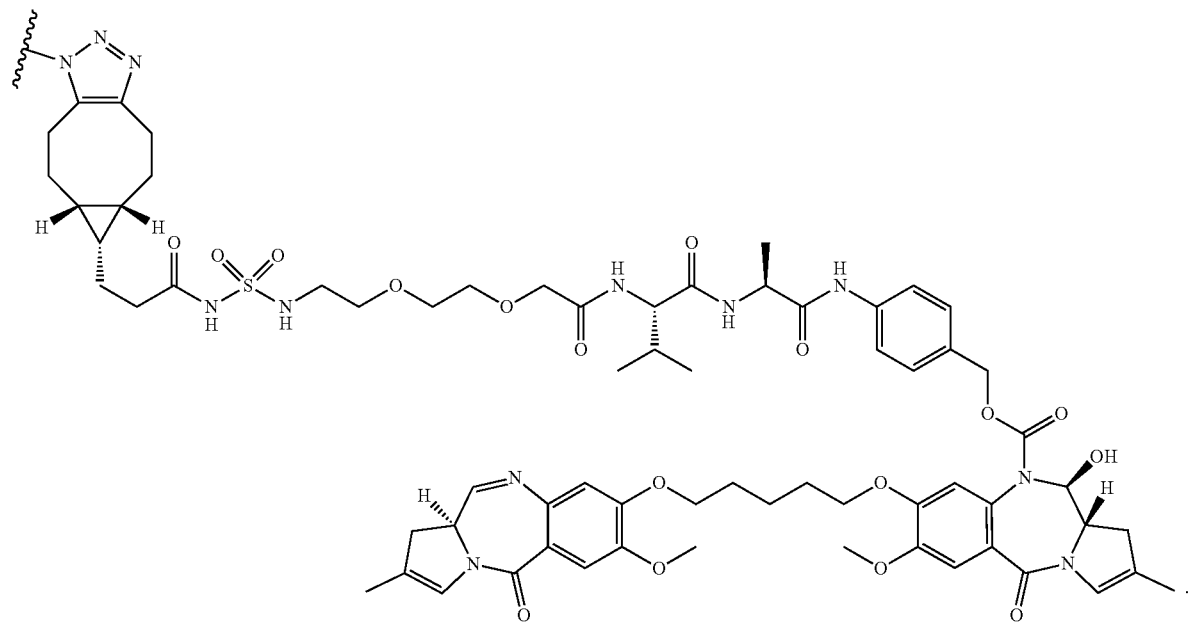

54. The conjugate according to any one of statements 1 to 53 wherein the antibody comprises a VH domain having a VH CDR3 with the amino acid sequence of SEQ ID NO.7.

55. The conjugate according to any one of statements 1 to 54 wherein the antibody comprises a VH domain comprising a VH CDR2 with the amino acid sequence of SEQ ID NO.6, and/or a VH CDR1 with the amino acid sequence of SEQ ID NO.5.

56. The conjugate according to any one of statements 1 to 55 wherein the antibody comprises a VH domain comprising a VH CDR3 with the amino acid sequence of SEQ ID NO.7., a VH CDR2 with the amino acid sequence of SEQ ID NO.6, and a VH CDR1 with the amino acid sequence of SEQ ID NO.5.

57. The conjugate according to any one of statements 1 to 56 wherein the antibody comprises a VH domain having the sequence of SEQ ID NO.1.

58. The conjugate according to any one of statements 1 to 57 wherein the antibody comprises a VL domain having a VL CDR3 with the amino acid sequence of SEQ ID NO.10.

59. The conjugate according to any one of statements 1 to 58 wherein the antibody comprises a VL domain comprising a VL CDR2 with the amino acid sequence of SEQ ID NO.9, and/or a VL CDR1 with the amino acid sequence of SEQ ID NO.8.

60. The conjugate according to any one of statements 1 to 59 wherein the antibody comprises a VL domain comprising a VL CDR3 with the amino acid sequence of SEQ ID NO.10, a VL CDR2 with the amino acid sequence of SEQ ID NO.9, and a VL CDR1 with the amino acid sequence of SEQ ID NO.8.

61. The conjugate according to any one of statements 1 to 60 wherein the antibody comprises a VL domain having the sequence of SEQ ID NO. 2.

62. The conjugate according to any one of statements 1 to 61 wherein the antibody in an intact antibody.

63. The conjugate according to any one of statements 1 to 62, wherein the antibody comprises a heavy chain having the sequence of SEQ ID NO. 3, or a heavy chain having the sequence of SEQ ID NO. 11.

64. The conjugate according to any one of statements 1 to 63, wherein the antibody comprises a light chain having the sequence of SEQ ID NO. 4.

65. The conjugate according to any one of statements 1 to 64 wherein the antibody is humanised, deimmunised or resurfaced.

66. The conjugate according to any one of statements 1 to 65, wherein there are no unconujated azide groups on the antibody.

67. The conjugate according to any one of statements 1 to 66, wherein p is 1, 2, 3, or 4.

68. A composition comprising a mixture of the antibody-drug conjugate compounds as defined in any one of statements 1 to 67, wherein the average drug loading per antibody in the mixture of antibody-drug conjugate compounds is about 1 to about 4.

69. The conjugate according to any one of statements 1 to 67, for use in therapy.

70. The conjugate according to any one of statements 1 to 67, for use in the treatment of a proliferative disease in a subject.

71. The conjugate according to statement 70, wherein the disease is cancer.

72. The conjugate according to statement 71, wherein the cancer is a cancer selected from the group consisting of: Hepatocellular carcinoma, hepatoblastoma, non small cell lung cancer, small cell lung cancer, colon cancer, breast cancer, gastric cancer, pancreatic cancer, neuroblastoma, adrenal gland cancer, pheochromocytoma, paraganglioma, thyroid medullary carcinoma, skeletal muscle cancer, liposarcoma, glioma, Wilms tumor, neuroendocrine tumors, Acute Myeloid Leukemia, and Myelodysplastic syndrome.

73. A pharmaceutical composition comprising the conjugate of any one of statements 1 to 67 and a pharmaceutically acceptable diluent, carrier or excipient.

74. The pharmaceutical composition of statement 73 further comprising a therapeutically effective amount of a chemotherapeutic agent.

75. Use of a conjugate according to any one of statements 1 to 67 in the preparation of a medicament for use in the treatment of a proliferative disease in a subject.

76. A method of treating cancer comprising administering to a patient the pharmaceutical composition of statements 74.

77. The method of statement 76 wherein the patient is administered a chemotherapeutic agent, in combination with the conjugate.

Anti-KAAG1 conjugates
1. A conjugate of formula (I):

Ab-(DL)$_p$  (I)

wherein:
Ab is an antibody that binds to KAAG1;
DL is

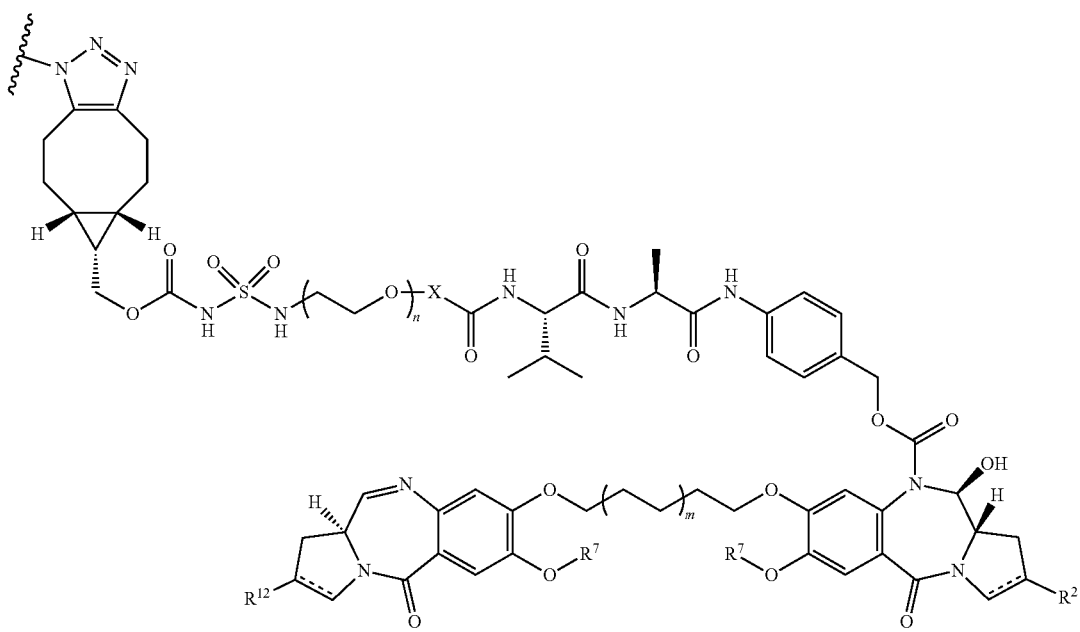

wherein:
X is selected from the group comprising: a single bond, —CH$_2$— and —C$_2$H$_4$—;
n is from 1 to 8;
m is 0 or 1;
R$^7$ is either methyl or phenyl;
when there is a double bond between C2 and C3, R$^2$ is selected the group consisting of:

(ia) C$_{5-10}$ aryl group, optionally substituted by one or more substituents selected from the group comprising: halo, nitro, cyano, ether, carboxy, ester, C$_{1-7}$ alkyl, C$_{3-7}$ heterocyclyl and bis-oxy-C$_{1-3}$ alkylene;

(ib) C$_{1-5}$ saturated aliphatic alkyl;

(ic) C$_{3-6}$ saturated cycloalkyl;

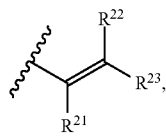 (id)

wherein each of R$^{21}$, R$^{22}$ and R$^{23}$ are independently selected from H, C$_{1-3}$ saturated alkyl, C$_{2-3}$ alkenyl, C$_{2-3}$ alkynyl and cyclopropyl, where the total number of carbon atoms in the R$^2$ group is no more than 5;

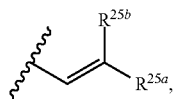 (ie)

wherein one of R$^{25a}$ and R$^{25b}$ is H and the other is selected from: phenyl, which phenyl is optionally substituted by a group selected from halo, methyl, methoxy; pyridyl; and thiophenyl; and

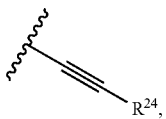

(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2 and C3, $R^2$ is

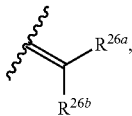

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

when there is a double bond between C2' and C3', $R^{12}$ is selected the group consisting of:

(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(iib) $C_{1-5}$ saturated aliphatic alkyl;

(iic) $C_{3-6}$ saturated cycloalkyl;

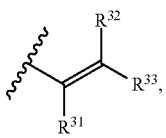

(iid)

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

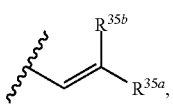

(iie)

wherein one of $R^{35a}$ and $R^{35b}$ is H and the other is selected from: phenyl, which phenyl is optionally substituted by a group selected from halo, methyl, methoxy; pyridyl; and thiophenyl; and

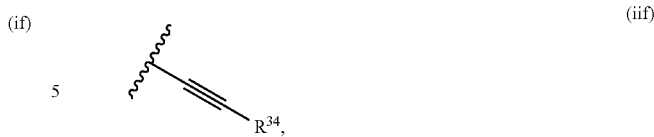

(iif)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2' and C3', $R^{12}$ is

where $R^{36a}$ and $R^{36b}$ are independently selected from H, F, C1-4 saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{36a}$ and $R^{36b}$ is H, the other is selected from nitrile and a C1-4 alkyl ester;

and p is from 1 to 8.

2. The conjugate according to statement 1, wherein X is a single bond.

3. The conjugate according to statement 1, wherein X is —$CH_2$—.

4. The conjugate according to statement 1, wherein X is —$C_2H_4$—.

5. The conjugate according to any one of statements 1 to 4, wherein n is 1 to 4.

6. The conjugate according to statement 5, wherein n is 1.

7. The conjugate according to statement 5, wherein n is 2.

8. The conjugate according to statement 5, wherein n is 4.

9. A compound according to any one of statements 1 to 8, wherein there is a double bond between $C_2$ and C3, and $R^2$ is a $C_{5-7}$ aryl group.

10. A compound according to statement 9, wherein $R^2$ is phenyl.

11. A compound according to any one of statements 1 to 8, wherein there is a double bond between C2 and C3, and $R^2$ is a $C_{5-10}$ aryl group.

12. A compound according to any one of statements 9 to 11, wherein $R^2$ bears one to three substituent groups.

13. A compound according to any one of statements 9 to 12, wherein the substituents are selected from methoxy, ethoxy, fluoro, chloro, cyano, bis-oxy-methylene, methyl-piperazinyl, morpholino and methyl-thiophenyl.

14. A compound according to any one of statements 1 to 8, wherein there is a double bond between C2 and C3, and $R^2$ is a $C_{1-5}$ saturated aliphatic alkyl group.

15. A compound according to statement 14, wherein $R^2$ is methyl, ethyl or propyl.

16. A compound according to any one of statements 1 to 8, wherein there is a double bond between C2 and C3, and $R^2$ is a C3-6 saturated cycloalkyl group.

17. A compound according to statement 16, wherein $R^2$ is cyclopropyl.

18. A compound according to any one of statements 1 to 8, wherein there is a double bond between C2 and C3, and $R^2$ is a group of formula:

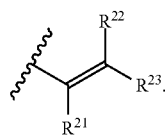

19. A compound according to statement 18, wherein the total number of carbon atoms in the $R^2$ group is no more than 4.

20. A compound according to statement 19, wherein the total number of carbon atoms in the $R^2$ group is no more than 3.

21. A compound according to any one of statements 18 to 20, wherein one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

22. A compound according to any one of statements 18 to 20, wherein two of $R^{21}$, $R^{22}$ and $R^{23}$ are H, with the other group being selected from H, $C_{1-3}$ saturated alkyl, $C_{2-3}$ alkenyl, C2-3 alkynyl and cyclopropyl.

23. A compound according to any one of statements 1 to 8, wherein there is a double bond between C2 and C3, and $R^2$ is a group of formula:

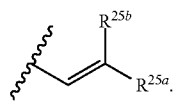

24. A compound according to statement 23, wherein $R^2$ is the group:

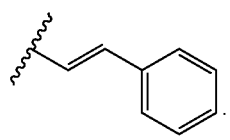

25. A compound according to any one of statements 1 to 8, wherein there is a double bond between C2 and C3, and $R^2$ is a group of formula:

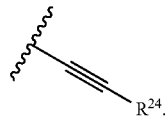

26. A compound according to statement 25, wherein $R^{24}$ is selected from H, methyl, ethyl, ethenyl and ethynyl.

27. A compound according to statement 26, wherein $R^{24}$ is selected from H and methyl.

28. A compound according to any one of statements 1 to 8, wherein there is a single bond between C2 and C3, $R^2$ is

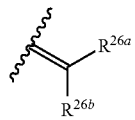

and $R^{26a}$ and $R^{26b}$ are both H.

29. A compound according to any one of statements 1 to 8, wherein there is a single bond between C2 and C3, $R^2$ is

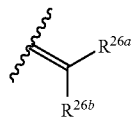

and $R^{26a}$ and $R^{26b}$ are both methyl.

30. A compound according to any one of statements 1 to 8, wherein there is a single bond between C2 and C3, $R^2$ is

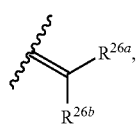

one of $R^{26a}$ and $R^{26b}$ is H, and the other is selected from $C_{1-4}$ saturated alkyl, $C_{2-3}$ alkenyl, which alkyl and alkenyl groups are optionally substituted.

31. A compound according to any one of statements 1 to 30, wherein there is a double bond between C2' and C3', and $R^{12}$ is a $C_{5-7}$ aryl group.

32. A compound according to statement 31, wherein $R^{12}$ is phenyl.

33. A compound according to any one of statements 1 to 30, wherein there is a double bond between C2' and C3', and $R^{12}$ is a $C_{8-10}$ aryl group.

34. A compound according to any one of statements 31 to 33, wherein $R^{12}$ bears one to three substituent groups.

35. A compound according to any one of statements 31 to 34, wherein the substituents are selected from methoxy, ethoxy, fluoro, chloro, cyano, bis-oxy-methylene, methyl-piperazinyl, morpholino and methyl-thiophenyl.

36. A compound according to any one of statements 1 to 30, wherein there is a double bond between C2' and C3', and $R^{12}$ is a $C_{1-5}$ saturated aliphatic alkyl group.

37. A compound according to statement 36, wherein $R^{12}$ is methyl, ethyl or propyl.

38. A compound according to any one of statements 1 to 30, wherein there is a double bond between C2' and C3', and $R^{12}$ is a $C_{3-6}$ saturated cycloalkyl group.

39. A compound according to statement 38, wherein $R^{12}$ is cyclopropyl.

40. A compound according to any one of statements 1 to 30, wherein there is a double bond between C2' and C3', and $R^{12}$ is a group of formula:

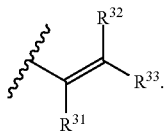

41. A compound according to statement 40, wherein the total number of carbon atoms in the $R^{12}$ group is no more than 4.

42. A compound according to statement 41, wherein the total number of carbon atoms in the $R^{12}$ group is no more than 3.

43. A compound according to any one of statements 40 to 42, wherein one of $R^{31}$, $R^{32}$ and $R^{33}$ is H, with the other two groups being selected from H, $C_{1-3}$ saturated alkyl, $C_{2-3}$ alkenyl, $C_{2-3}$ alkynyl and cyclopropyl.

44. A compound according to any one of statements 40 to 42, wherein two of $R^{31}$, $R^{32}$ and $R^{33}$ are H, with the other group being selected from H, $C_{1-3}$ saturated alkyl, $C_{2-3}$ alkenyl, $C_{2-3}$ alkynyl and cyclopropyl.

45. A compound according to any one of statements 1 to 30, wherein there is a double bond between C2' and C3', and $R^{12}$ is a group of formula:

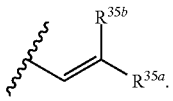

46. A compound according to statement 45, wherein $R^{12}$ is the group:

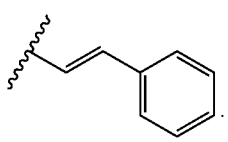

47. A compound according to any one of statements 1 to 30, wherein there is a double bond between C2' and C3', and $R^{12}$ is a group of formula:

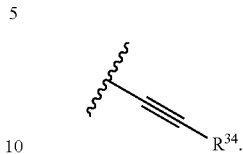

48. A compound according to statement 47, wherein $R^{34}$ is selected from H, methyl, ethyl, ethenyl and ethynyl.

49. A compound according to statement 48, wherein $R^{34}$ is selected from H and methyl.

50. A compound according to any one of statements 1 to 30, wherein there is a single bond between C2' and C3', $R^{12}$ is

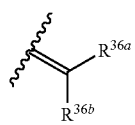

and $R^{36a}$ and $R^{36b}$ are both H.

51. A compound according to any one of statements 1 to 30, wherein there is a single bond between C2' and C3', $R^{12}$ is

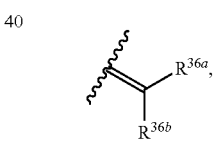

and $R^{36a}$ and $R^{36b}$ are both methyl.

52. A compound according to any one of statements 1 to 30, wherein there is a single bond between C2' and C3', $R^{12}$ is

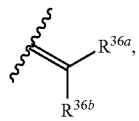

one of $R^{36a}$ and $R^{36b}$ is H, and the other is selected from $C_{1-4}$ saturated alkyl, $C_{2-3}$ alkenyl, which alkyl and alkenyl groups are optionally substituted.

53. A conjugate according to statement 1, wherein DL is:

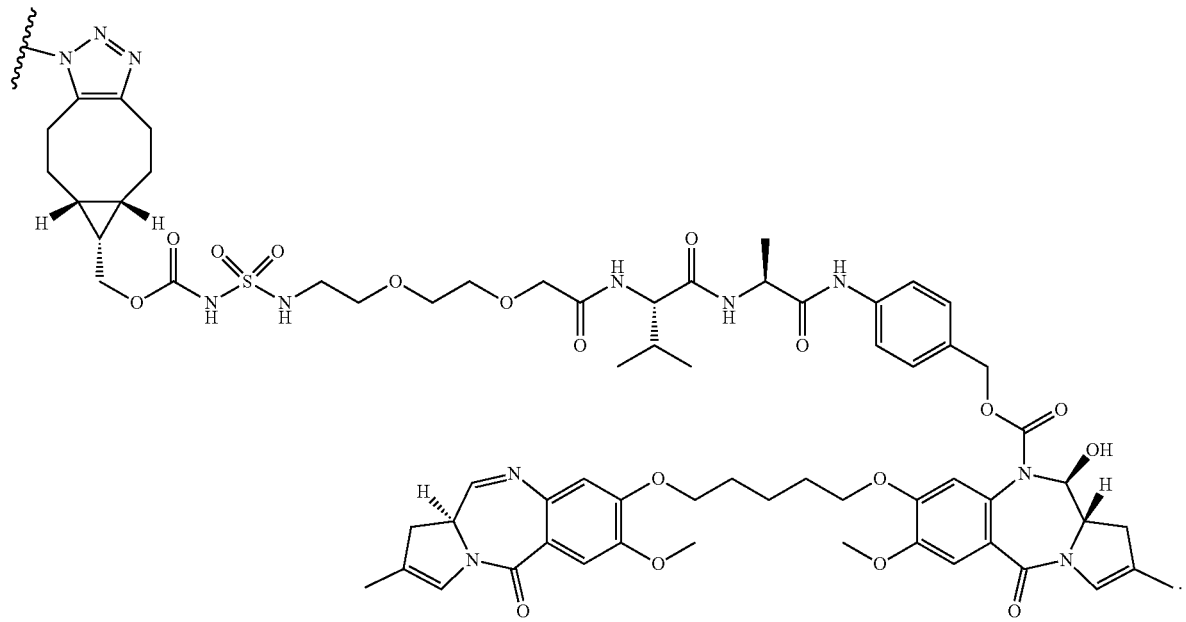 [SMILES: *n1nnc2c1CC[C@@H]1[C@H](CC2)[C@@H]1COC(=O)NS(=O)(=O)NCCOCCOCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4C=N5)c(OC)cc3C(=O)N3C=C(C)C[C@H]3[C@@H]2O)cc1)C(C)C]

54. The conjugate according to any one of statements 1 to 53 wherein the antibody comprises a VH domain having a VH CDR3 with the amino acid sequence of SEQ ID NO.107.

55. The conjugate according to any one of statements 1 to 54 wherein the antibody comprises a VH domain comprising a VH CDR2 with the amino acid sequence of SEQ ID NO.106, and/or a VH CDR1 with the amino acid sequence of SEQ ID NO.105.

56. The conjugate according to any one of statements 1 to 55 wherein the antibody comprises a VH domain comprising a VH CDR3 with the amino acid sequence of SEQ ID NO.107, a VH CDR2 with the amino acid sequence of SEQ ID NO.106, and a VH CDR1 with the amino acid sequence of SEQ ID NO.105.

57. The conjugate according to any one of statements 1 to 56 wherein the antibody comprises a VH domain having the sequence of SEQ ID NO.101.

58. The conjugate according to any one of statements 1 to 57 wherein the antibody comprises a VL domain having a VL CDR3 with the amino acid sequence of SEQ ID NO.110.

59. The conjugate according to any one of statements 1 to 58 wherein the antibody comprises a VL domain comprising a VL CDR2 with the amino acid sequence of SEQ ID NO.109, and/or a VL CDR1 with the amino acid sequence of SEQ ID NO.108.

60. The conjugate according to any one of statements 1 to 59 wherein the antibody comprises a VL domain comprising a VL CDR3 with the amino acid sequence of SEQ ID NO.110, a VL CDR2 with the amino acid sequence of SEQ ID NO.109, and a VL CDR1 with the amino acid sequence of SEQ ID NO.108.

61. The conjugate according to any one of statements 1 to 60 wherein the antibody comprises a VL domain having the sequence of SEQ ID NO.102.

62. The conjugate according to any one of statements 1 to 60 wherein the antibody comprises a VL domain having the sequence of SEQ ID NO.113. 63. The conjugate according to any one of statements 1 to 60 wherein the antibody comprises a VL domain having the sequence of SEQ ID NO. 115.

64. The conjugate according to any one of statements 1 to 63 wherein the antibody in an intact antibody.

65. The conjugate according to any one of statements 1 to 64, wherein the antibody comprises a heavy chain having the sequence of SEQ ID NO.103, or a heavy chain having the sequence of SEQ ID NO.111.

66. The conjugate according to any one of statements 1 to 65, wherein the antibody comprises a light chain having the sequence of SEQ ID NO.104.

67. The conjugate according to any one of statements 1 to 65, wherein the antibody comprises a light chain having the sequence of SEQ ID NO.114.

68. The conjugate according to any one of statements 1 to 65, wherein the antibody comprises a light chain having the sequence of SEQ ID NO.116.

69. The conjugate according to any one of statements 1 to 68 wherein the antibody is humanised, deimmunised or resurfaced.

70. The conjugate according to any one of statements 1 to 69, wherein there are no unconujated azide groups on the antibody.

71. The conjugate according to any one of statements 1 to 70, wherein p is 1, 2, 3, or 4.

72. A composition comprising a mixture of the antibody-drug conjugate compounds as defined in any one of statements 1 to 71, wherein the average drug loading per antibody in the mixture of antibody-drug conjugate compounds is about 1 to about 4.

73. The conjugate according to any one of statements 1 to 71, for use in therapy.

74. The conjugate according to any one of statements 1 to 71, for use in the treatment of a proliferative disease in a subject.

75. The conjugate according to statement 74, wherein the disease is cancer.

76. The conjugate according to statement 75, wherein the cancer is a cancer selected from the group consisting of: ovarian, breast, prostate and renal cancer.

77. A pharmaceutical composition comprising the conjugate of any one of statements 1 to 71 and a pharmaceutically acceptable diluent, carrier or excipient.

78. The pharmaceutical composition of statement 77 further comprising a therapeutically effective amount of a chemotherapeutic agent.

79. Use of a conjugate according to any one of statements 1 to 71 in the preparation of a medicament for use in the treatment of a proliferative disease in a subject.

80. A method of treating cancer comprising administering to a patient the pharmaceutical composition of statements 78.

81. The method of statement 80 wherein the patient is administered a chemotherapeutic agent, in combination with the conjugate.

Anti-Mesothelin conjugates

1. A conjugate of formula (I):

Ab-(DL)$_p$   (I)

wherein:
Ab is an antibody that binds to Mesothelin;
DL is

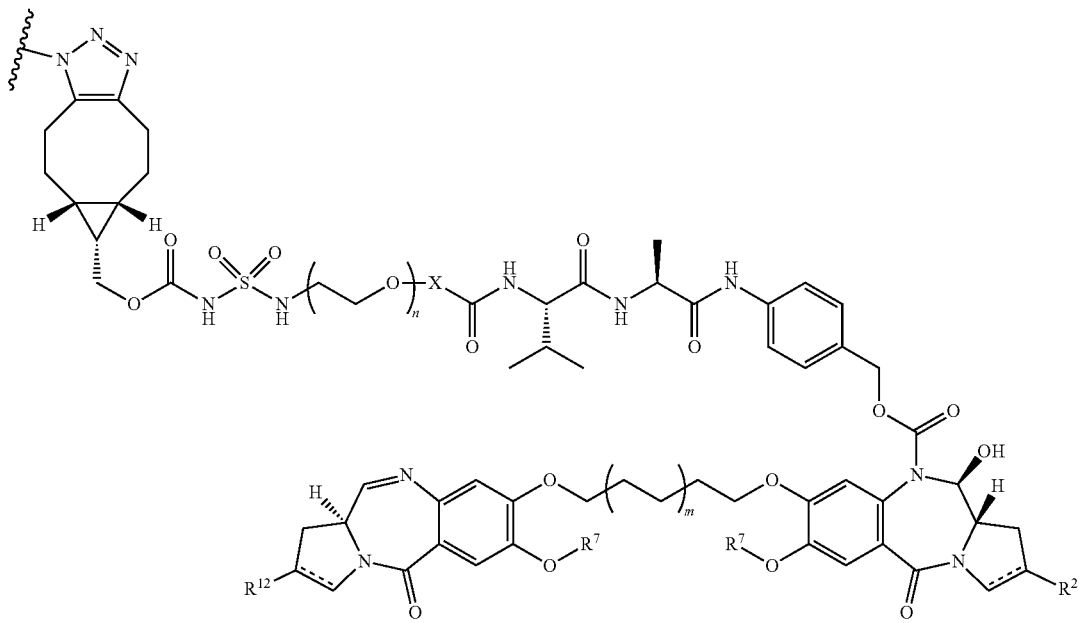

wherein:
X is selected from the group comprising: a single bond, —CH$_2$— and —C$_2$H$_4$—;

n is from 1 to 8;

m is 0 or 1;

R$^7$ is either methyl or phenyl;

when there is a double bond between C2 and C3, R$^2$ is selected the group consisting of:

(ia) C5-10 aryl group, optionally substituted by one or more substituents selected from the group comprising: halo, nitro, cyano, ether, carboxy, ester, C$_{1-7}$ alkyl, C$_{3-7}$ heterocyclyl and bis-oxy-C$_{1-3}$ alkylene;

(ib) C$_{1-5}$ saturated aliphatic alkyl;

(ic) C$_{3-6}$ saturated cycloalkyl;

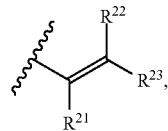   (id)

wherein each of R$^{21}$, R$^{22}$ and R$^{23}$ are independently selected from H, C$_{1-3}$ saturated alkyl, C$_{2-3}$ alkenyl, C$_{2-3}$ alkynyl and cyclopropyl, where the total number of carbon atoms in the R$^2$ group is no more than 5;

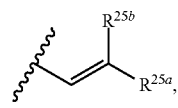   (ie)

wherein one of R$^{25a}$ and R$^{25b}$ is H and the other is selected from: phenyl, which phenyl is optionally substituted by a group selected from halo, methyl, methoxy; pyridyl; and thiophenyl; and

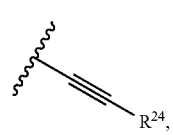   (if)

where R$^{24}$ is selected from: H; C$_{1-3}$ saturated alkyl; C$_{2-3}$ alkenyl; C$_{2-3}$ alkynyl; cyclopropyl; phenyl, which phenyl is optionally substituted by a group selected from halo, methyl, methoxy; pyridyl; and thiophenyl;

when there is a single bond between C2 and C3, $R^2$ is

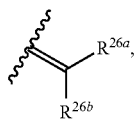

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a C1-4 alkyl ester;

when there is a double bond between C2' and C3', $R^{12}$ is selected the group consisting of:

(iia) $C_{5-10}$ aryl group, optionally substituted by one or more substituents selected from the group comprising: halo, nitro, cyano, ether, carboxy, ester, C1-7 alkyl, $C_{3-7}$ heterocyclyl and bis-oxy-$C_{1-3}$ alkylene;

(iib) $C_{1-5}$ saturated aliphatic alkyl;

(iic) $C_{3-6}$ saturated cycloalkyl;

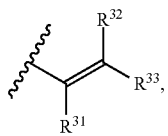
(iid)

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

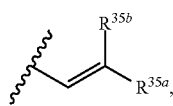
(iie)

wherein one of $R^{35a}$ and $R^{35b}$ is H and the other is selected from: phenyl, which phenyl is optionally substituted by a group selected from halo, methyl, methoxy; pyridyl; and thiophenyl; and

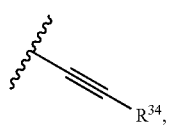
(iif)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2' and C3', $R^{12}$ is

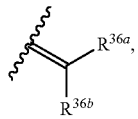

where $R^{36a}$ and $R^{36b}$ are independently selected from H, F, C1-4 saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{36a}$ and $R^{36b}$ is H, the other is selected from nitrile and a C1-4 alkyl ester;

and p is from 1 to 8.

2. The conjugate according to statement 1, wherein X is a single bond.

3. The conjugate according to statement 1, wherein X is —$CH_2$—.

4. The conjugate according to statement 1, wherein X is —$C_2H_4$—.

5. The conjugate according to any one of statements 1 to 4, wherein n is 1 to 4.

6. The conjugate according to statement 5, wherein n is 1.

7. The conjugate according to statement 5, wherein n is 2.

8. The conjugate according to statement 5, wherein n is 4.

9. A compound according to any one of statements 1 to 8, wherein there is a double bond between C2 and C3, and $R^2$ is a $C_{5-7}$ aryl group.

10. A compound according to statement 9, wherein $R^2$ is phenyl.

11. A compound according to any one of statements 1 to 8, wherein there is a double bond between C2 and C3, and $R^2$ is a $C_{8-10}$ aryl group.

12. A compound according to any one of statements 9 to 11, wherein $R^2$ bears one to three substituent groups.

13. A compound according to any one of statements 9 to 12, wherein the substituents are selected from methoxy, ethoxy, fluoro, chloro, cyano, bis-oxy-methylene, methyl-piperazinyl, morpholino and methyl-thiophenyl.

14. A compound according to any one of statements 1 to 8, wherein there is a double bond between C2 and C3, and $R^2$ is a $C_{1-5}$ saturated aliphatic alkyl group.

15. A compound according to statement 14, wherein $R^2$ is methyl, ethyl or propyl.

16. A compound according to any one of statements 1 to 8, wherein there is a double bond between C2 and C3, and $R^2$ is a C3-6 saturated cycloalkyl group.

17. A compound according to statement 16, wherein $R^2$ is cyclopropyl.

18. A compound according to any one of statements 1 to 8, wherein there is a double bond between C2 and C3, and $R^2$ is a group of formula:

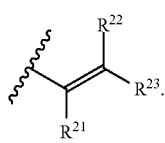

19. A compound according to statement 18, wherein the total number of carbon atoms in the $R^2$ group is no more than 4.

20. A compound according to statement 19, wherein the total number of carbon atoms in the $R^2$ group is no more than 3.

21. A compound according to any one of statements 18 to 20, wherein one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

22. A compound according to any one of statements 18 to 20, wherein two of $R^{21}$, $R^{22}$ and $R^{23}$ are H, with the other group being selected from H, $C_{1-3}$ saturated alkyl, $C_{2-3}$ alkenyl, C2-3 alkynyl and cyclopropyl.

23. A compound according to any one of statements 1 to 8, wherein there is a double bond between C2 and C3, and $R^2$ is a group of formula:

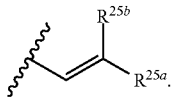

24. A compound according to statement 23, wherein $R^2$ is the group:

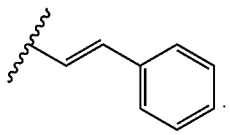 [SMILES: */C=C/c1ccccc1]

25. A compound according to any one of statements 1 to 8, wherein there is a double bond between C2 and C3, and $R^2$ is a group of formula:

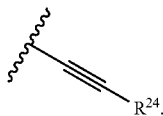

26. A compound according to statement 25, wherein $R^{24}$ is selected from H, methyl, ethyl, ethenyl and ethynyl.

27. A compound according to statement 26, wherein $R^{24}$ is selected from H and methyl.

28. A compound according to any one of statements 1 to 8, wherein there is a single bond between C2 and C3, $R^2$ is

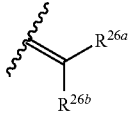

and $R^{26a}$ and $R^{26b}$ are both H.

29. A compound according to any one of statements 1 to 8, wherein there is a single bond between C2 and C3, $R^2$ is

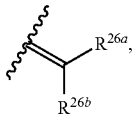

and $R^{26a}$ and $R^{26b}$ are both methyl.

30. A compound according to any one of statements 1 to 8, wherein there is a single bond between C2 and C3, $R^2$ is

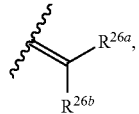

one of $R^{26a}$ and $R^{26b}$ is H, and the other is selected from $C_{1-4}$ saturated alkyl, $C_{2-3}$ alkenyl, which alkyl and alkenyl groups are optionally substituted.

31. A compound according to any one of statements 1 to 30, wherein there is a double bond between C2' and C3', and $R^{12}$ is a $C_{5-7}$ aryl group.

32. A compound according to statement 31, wherein $R^{12}$ is phenyl.

33. A compound according to any one of statements 1 to 30, wherein there is a double bond between C2' and C3', and $R^{12}$ is a $C_{8-10}$ aryl group.

34. A compound according to any one of statements 31 to 33, wherein $R^{12}$ bears one to three substituent groups.

35. A compound according to any one of statements 31 to 34, wherein the substituents are selected from methoxy, ethoxy, fluoro, chloro, cyano, bis-oxy-methylene, methyl-piperazinyl, morpholino and methyl-thiophenyl.

36. A compound according to any one of statements 1 to 30, wherein there is a double bond between C2' and C3', and $R^{12}$ is a $C_{1-5}$ saturated aliphatic alkyl group.

37. A compound according to statement 36, wherein $R^{12}$ is methyl, ethyl or propyl.

38. A compound according to any one of statements 1 to 30, wherein there is a double bond between C2' and C3', and $R^{12}$ is a $C_{3-6}$ saturated cycloalkyl group.

39. A compound according to statement 38, wherein $R^{12}$ is cyclopropyl.

40. A compound according to any one of statements 1 to 30, wherein there is a double bond between C2' and C3', and $R^{12}$ is a group of formula:

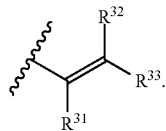

41. A compound according to statement 40, wherein the total number of carbon atoms in the $R^{12}$ group is no more than 4.

42. A compound according to statement 41, wherein the total number of carbon atoms in the $R^{12}$ group is no more than 3.

43. A compound according to any one of statements 40 to 42, wherein one of $R^{31}$, $R^{32}$ and $R^{33}$ is H, with the other two groups being selected from H, $C_{1-3}$ saturated alkyl, $C_{2-3}$ alkenyl, $C_{2-3}$ alkynyl and cyclopropyl.

44. A compound according to any one of statements 40 to 42, wherein two of $R^{31}$, $R^{32}$ and $R^{33}$ are H, with the other group being selected from H, $C_{1-3}$ saturated alkyl, $C_{2-3}$ alkenyl, $C_{2-3}$ alkynyl and cyclopropyl.

45. A compound according to any one of statements 1 to 30, wherein there is a double bond between C2' and C3', and $R^{12}$ is a group of formula:

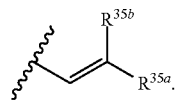

46. A compound according to statement 45, wherein $R^{12}$ is the group:

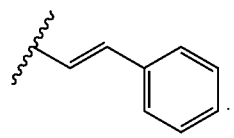 [SMILES: */C=C/c1ccccc1]

47. A compound according to any one of statements 1 to 30, wherein there is a double bond between C2' and C3', and $R^{12}$ is a group of formula:

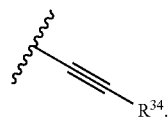

48. A compound according to statement 47, wherein $R^{34}$ is selected from H, methyl, ethyl, ethenyl and ethynyl.

49. A compound according to statement 48, wherein $R^{34}$ is selected from H and methyl.

50. A compound according to any one of statements 1 to 30, wherein there is a single bond between C2' and C3', $R^{12}$ is

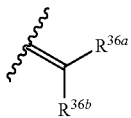

and $R^{36a}$ and $R^{36b}$ are both H.

51. A compound according to any one of statements 1 to 30, wherein there is a single bond between C2' and C3', $R^{12}$ is

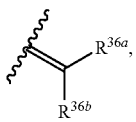

and $R^{36a}$ and $R^{36b}$ are both methyl.

52. A compound according to any one of statements 1 to 30, wherein there is a single bond between C2' and C3', $R^{12}$ is

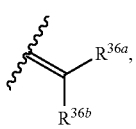

one of $R^{36a}$ and $R^{36b}$ is H, and the other is selected from $C_{1-4}$ saturated alkyl, $C_{2-3}$ alkenyl, which alkyl and alkenyl groups are optionally substituted.

53. A conjugate according to statement 1, wherein DL is:

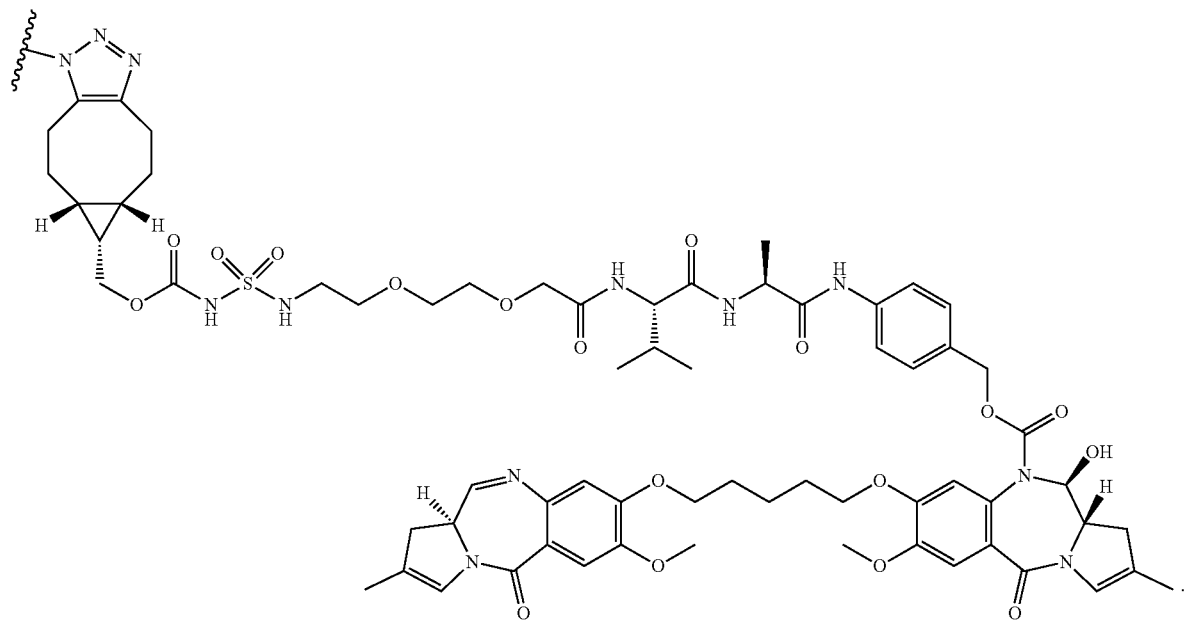 [SMILES: *n1nnc2c1CC[C@@H]1[C@H](CC2)[C@@H]1COC(=O)NS(=O)(=O)NCCOCCOCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4C=N5)c(OC)cc3C(=O)N3C=C(C)C[C@H]3[C@@H]2O)cc1)C(C)C]

54. The conjugate according to any one of statements 1 to 53 wherein the antibody comprises a VH domain having a VH CDR3 with the amino acid sequence of SEQ ID NO.207.

55. The conjugate according to any one of statements 1 to 54 wherein the antibody comprises a VH domain comprising a VH CDR2 with the amino acid sequence of SEQ ID NO.206, and/or a VH CDR1 with the amino acid sequence of SEQ ID NO.205.

56. The conjugate according to any one of statements 1 to 55 wherein the antibody comprises a VH domain comprising a VH CDR3 with the amino acid sequence of SEQ ID NO.207, a VH CDR2 with the amino acid sequence of SEQ ID NO.206, and a VH CDR1 with the amino acid sequence of SEQ ID NO.205.

57. The conjugate according to any one of statements 1 to 56 wherein the antibody comprises a VH domain having the sequence of SEQ ID NO.201.

58. The conjugate according to any one of statements 1 to 57 wherein the antibody comprises a VL domain having a VL CDR3 with the amino acid sequence of SEQ ID NO.210.

59. The conjugate according to any one of statements 1 to 58 wherein the antibody comprises a VL domain comprising a VL CDR2 with the amino acid sequence of SEQ ID NO.209, and/or a VL CDR1 with the amino acid sequence of SEQ ID NO.208.

60. The conjugate according to any one of statements 1 to 59 wherein the antibody comprises a VL domain comprising a VL CDR3 with the amino acid sequence of SEQ ID NO.210, a VL CDR2 with the amino acid sequence of SEQ ID NO.209, and a VL CDR1 with the amino acid sequence of SEQ ID NO.208.

61. The conjugate according to any one of statements 1 to 60 wherein the antibody comprises a VL domain having the sequence of SEQ ID NO. 202.

62. The conjugate according to any one of statements 1 to 61 wherein the antibody in an intact antibody.

63. The conjugate according to any one of statements 1 to 62, wherein the antibody comprises a heavy chain having the sequence of SEQ ID NO.203, or a heavy chain having the sequence of SEQ ID NO. 211.

64. The conjugate according to any one of statements 1 to 63, wherein the antibody comprises a light chain having the sequence of SEQ ID NO.204.

65. The conjugate according to any one of statements 1 to 53 wherein the antibody comprises a VH domain having a VH CDR3 with the amino acid sequence of SEQ ID NO.218.

66. The conjugate according to any one of statements 1 to 53 or 65 wherein the antibody comprises a VH domain comprising a VH CDR2 with the amino acid sequence of SEQ ID NO.217, and/or a VH CDR1 with the amino acid sequence of SEQ ID NO.216.

67. The conjugate according to any one of statements 1 to 53 or 65 to 66 wherein the antibody comprises a VH domain comprising a VH CDR3 with the amino acid sequence of SEQ ID NO.218., a VH CDR2 with the amino acid sequence of SEQ ID NO.217, and a VH CDR1 with the amino acid sequence of SEQ ID NO.216.

68. The conjugate according to any one of statements 1 to 53 or 65 to 67 wherein the antibody comprises a VH domain having the sequence of SEQ ID NO.212.

69. The conjugate according to any one of statements 1 to 53 or 65 to 68 wherein the antibody comprises a VL domain having a VL CDR3 with the amino acid sequence of SEQ ID NO.221.

70. The conjugate according to any one of statements 1 to 53 or 65 to 69 wherein the antibody comprises a VL domain comprising a VL CDR2 with the amino acid sequence of SEQ ID NO.220, and/or a VL CDR1 with the amino acid sequence of SEQ ID NO.219.

71. The conjugate according to any one of statements 1 to 53 or 65 to 70 wherein the antibody comprises a VL domain comprising a VL CDR3 with the amino acid sequence of SEQ ID NO.221., a VL CDR2 with the amino acid sequence of SEQ ID NO.220, and a VL CDR1 with the amino acid sequence of SEQ ID NO.219.

72. The conjugate according to any one of statements 1 to 53 or 65 to 71 wherein the antibody comprises a VL domain having the sequence of SEQ ID NO. 213.

73. The conjugate according to any one of statements 1 to 53 or 65 to 72 wherein the antibody in an intact antibody.

74. The conjugate according to any one of statements 1 to 53 or 65 to 73, wherein the antibody comprises a heavy chain having the sequence of SEQ ID NO. 214, or a heavy chain having the sequence of SEQ ID NO. 222.

75. The conjugate according to any one of statements 1 to 53 or 65 to 74, wherein the antibody comprises a light chain having the sequence of SEQ ID NO. 215.

76. The conjugate according to any one of statements 1 to 53 wherein the antibody comprises a VH domain having a VH CDR3 with the amino acid sequence of SEQ ID NO.229.

77. The conjugate according to any one of statements 1 to 53 or 76 wherein the antibody comprises a VH domain comprising a VH CDR2 with the amino acid sequence of SEQ ID NO.228, and/or a VH CDR1 with the amino acid sequence of SEQ ID NO.227.

78. The conjugate according to any one of statements 1 to 53 or 76 to 77 wherein the antibody comprises a VH domain comprising a VH CDR3 with the amino acid sequence of SEQ ID NO.228., a VH CDR2 with the amino acid sequence of SEQ ID NO.227, and a VH CDR1 with the amino acid sequence of SEQ ID NO.226.

79. The conjugate according to any one of statements 1 to 53 or 76 to 78 wherein the antibody comprises a VH domain having the sequence of SEQ ID NO.223.

80. The conjugate according to any one of statements 1 to 53 or 76 to 79 wherein the antibody comprises a VL domain having a VL CDR3 with the amino acid sequence of SEQ ID NO.232.

81. The conjugate according to any one of statements 1 to 53 or 76 to 80 wherein the antibody comprises a VL domain comprising a VL CDR2 with the amino acid sequence of SEQ ID NO.231, and/or a VL CDR1 with the amino acid sequence of SEQ ID NO.230.

82. The conjugate according to any one of statements 1 to 53 or 76 to 81 wherein the antibody comprises a VL domain comprising a VL CDR3 with the amino acid sequence of SEQ ID NO.232., a VL CDR2 with the amino acid sequence of SEQ ID NO.231, and a VL CDR1 with the amino acid sequence of SEQ ID NO.230.

83. The conjugate according to any one of statements 1 to 53 or 76 to 82 wherein the antibody comprises a VL domain having the sequence of SEQ ID NO. 224.

84. The conjugate according to any one of statements 1 to 53 or 76 to 83 wherein the antibody in an intact antibody.

85. The conjugate according to any one of statements 1 to 53 or 76 to 84, wherein the antibody comprises a heavy chain having the sequence of SEQ ID NO.225, or a heavy chain having the sequence of SEQ ID NO.233.

86. The conjugate according to any one of statements 1 to 53 or 76 to 85, wherein the antibody comprises a light chain having the sequence of SEQ ID NO.226.

87. The conjugate according to any one of statements 1 to 53 wherein the antibody comprises a VH domain having a VH CDR3 with the amino acid sequence of SEQ ID NO.240.

88. The conjugate according to any one of statements 1 to 53 or 87 wherein the antibody comprises a VH domain comprising a VH CDR2 with the amino acid sequence of SEQ ID NO.239, and/or a VH CDR1 with the amino acid sequence of SEQ ID NO.238.

89. The conjugate according to any one of statements 1 to 53 or 87 to 88 wherein the antibody comprises a VH domain comprising a VH CDR3 with the amino acid sequence of SEQ ID NO.240, a VH CDR2 with the amino acid sequence of SEQ ID NO.239, and a VH CDR1 with the amino acid sequence of SEQ ID NO.238.

90. The conjugate according to any one of statements 1 to 53 or 87 to 89 wherein the antibody comprises a VH domain having the sequence of SEQ ID NO.234. 91. The conjugate according to any one of statements 1 to 53 or 87 to 90 wherein the antibody comprises a VL domain having a VL CDR3 with the amino acid sequence of SEQ ID NO.243.

92. The conjugate according to any one of statements 1 to 53 or 87 to 91 wherein the antibody comprises a VL domain comprising a VL CDR2 with the amino acid sequence of SEQ ID NO.242, and/or a VL CDR1 with the amino acid sequence of SEQ ID NO.241.

93. The conjugate according to any one of statements 1 to 53 or 87 to 92 wherein the antibody comprises a VL domain comprising a VL CDR3 with the amino acid sequence of
SEQ ID NO.243., a VL CDR2 with the amino acid sequence of SEQ ID NO.242, and a VL CDR1 with the amino acid sequence of SEQ ID NO.241.

94. The conjugate according to any one of statements 1 to 53 or 87 to 93 wherein the antibody comprises a VL domain having the sequence of SEQ ID NO.235.

95. The conjugate according to any one of statements 1 to 53 or 87 to 94 wherein the antibody in an intact antibody.

96. The conjugate according to any one of statements 1 to 53 or 87 to 95, wherein the antibody comprises a heavy chain having the sequence of SEQ ID NO.236, or a heavy chain having the sequence of SEQ ID NO.244.

97. The conjugate according to any one of statements 1 to 53 or 87 to 96, wherein the antibody comprises a light chain having the sequence of SEQ ID NO.237.

98. The conjugate according to any one of statements 1 to 97 wherein the antibody is humanised, deimmunised or resurfaced.

99. The conjugate according to any one of statements 1 to 98, wherein there are no unconujated azide groups on the antibody.

100. The conjugate according to any one of statements 1 to 99, wherein p is 1, 2, 3, or 4.

101. A composition comprising a mixture of the antibody-drug conjugate compounds as defined in any one of statements 1 to 100, wherein the average drug loading per antibody in the mixture of antibody-drug conjugate compounds is about 1 to about 4.

102. The conjugate according to any one of statements 1 to 100, for use in therapy.

103. The conjugate according to any one of statements 1 to 100, for use in the treatment of a proliferative disease in a subject.

104. The conjugate according to statement 103, wherein the disease is cancer.

105. The conjugate according to statement 104, wherein the cancer is a cancer selected from the group consisting of: mesothelioma, lung cancer, ovarian cancer and pancreatic cancer.

106. A pharmaceutical composition comprising the conjugate of any one of statements 1 to 100 and a pharmaceutically acceptable diluent, carrier or excipient.

107. The pharmaceutical composition of statement 106 further comprising a therapeutically effective amount of a chemotherapeutic agent.

108. Use of a conjugate according to any one of statements 1 to 100 in the preparation of a medicament for use in the treatment of a proliferative disease in a subject.

109. A method of treating cancer comprising administering to a patient the pharmaceutical composition of statement 101.

110. The method of statement 109 wherein the patient is administered a chemotherapeutic agent, in combination with the conjugate.

EXAMPLES

Overview

The ADCs disclosed herein are synthesised in a two-stage process. The first stage—glycan remodelling—trims the native N-linked glycan back to the core GlcNAc and then adds an azido modified GalNAc to form an antibody-GalNAc-N$_3$ intermediate. This is purified by Protein A chromatography and then conjugated to the drug linker in the second stage.

These stages are described below the following description of how the drug-linker is synthesised.

Synthesis of Intermediate 3

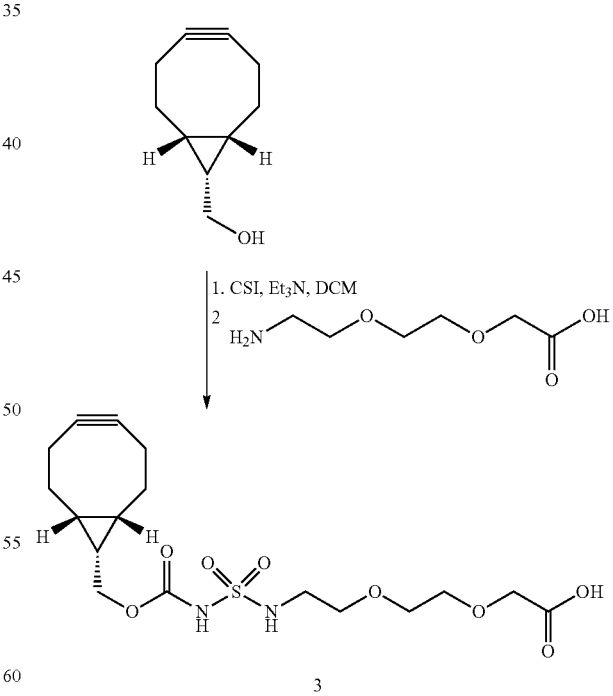

A solution of BCN alcohol (0.384 g, 2.55 mmole) in MeCN (25 mL) under a N$_2$ atmosphere was cooled to 0° C., and chlorosulfonyl isocyanate was added (CSI) was added dropwise (0.255 mL, 415 mg, 2.93 mmole, 1.15 equiv.). After stirring for 15 minutes, Et$_3$N was added dropwise (1.42 mL, 1.03 g, 10.2 mmole, 4 equiv.) and stirring was continued for another 10 minutes. Next, a solution of 2-(2-(2-aminoethoxy)ethoxy)acetic acid (1.0 g, 6.1 mmole, 2.4 equiv.) in H₂O (5 mL) was added and the reaction mixture was stirred to room temperature for 2 h. After this time, CHCl₃ (50 mL) and H₂O (100 mL) were added, and the layers were separated. To the aqueous layer in a separatory funnel was added CH₂Cl₂ (100 mL) and the pH was adjusted to 4 with 1 N HCl, before separation of layers. The water layer was extracted twice with CH₂Cl₂ (2×100 mL), the organic layers were combined and dried (Na₂SO₄), filtered and concentrated. The residue was purified by flask column chromatography on silica, elution with CH₂Cl₂ to 20% MeOH in CH₂Cl₂. Yield 0.42 g (1.0 mmole, 39%) of 3 as a colorless sticky wax.

Synthesis of Drug Linker

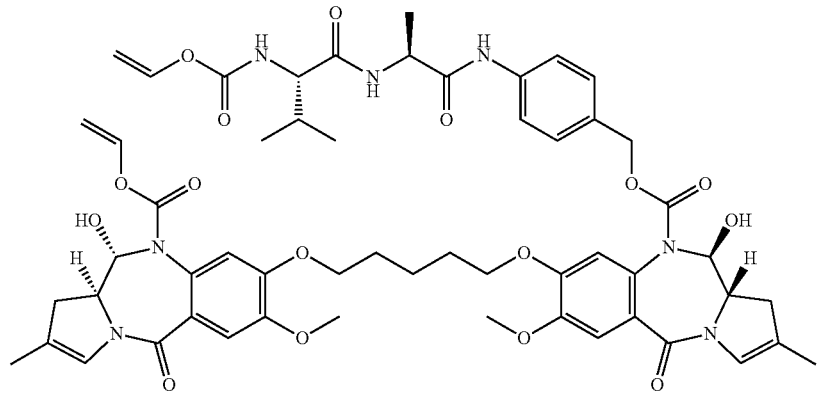

1

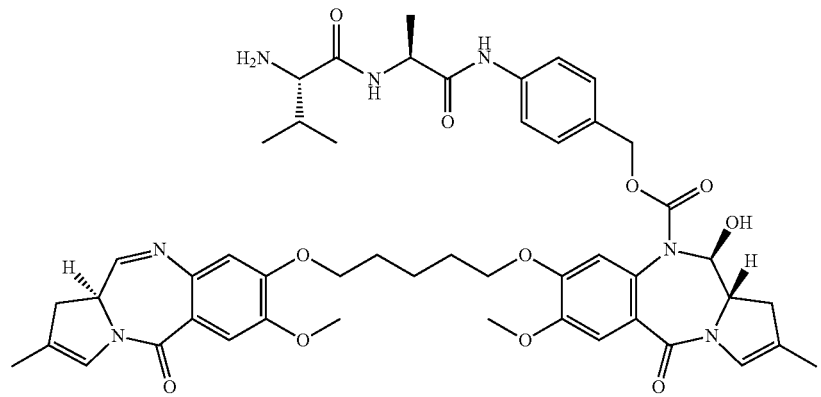

+

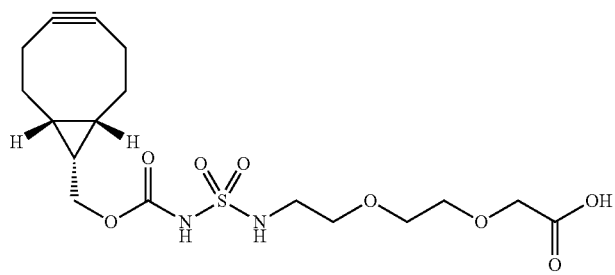

3

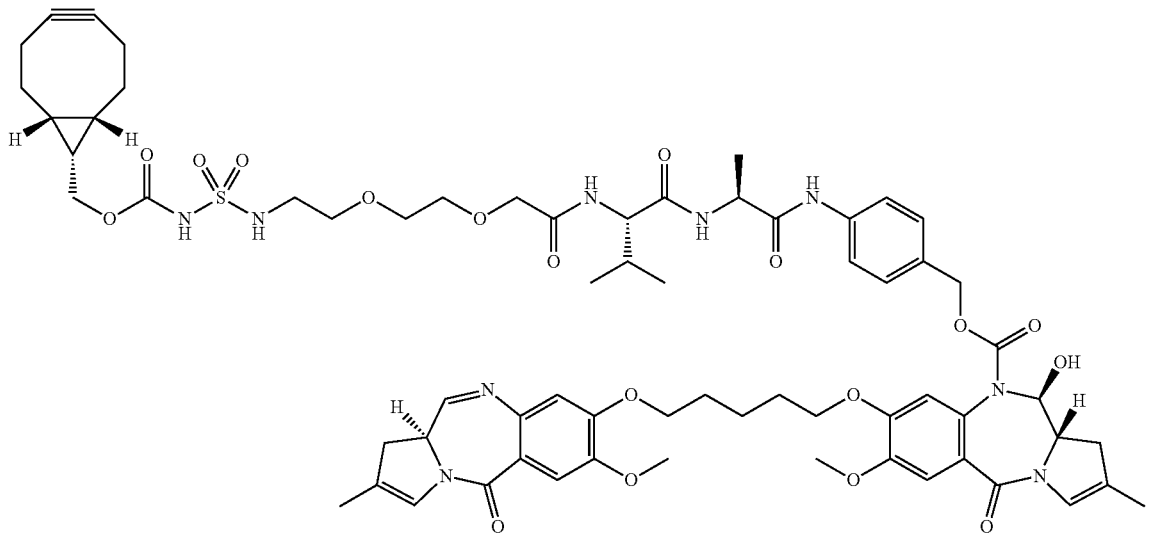

4

Compound 1 can be synthesised as described in WO2014/057074—see compound 22.

(a) Palladium tetrakistriphenylphosphine (Pd(PPh$_3$)$_4$, 4.8 mg, 4.15 µmol) is weighed and put under an inert atmosphere. A solution of pyrrolidine (5.0 µL, 4.3 mg, 60 µmol) in DCM (1 mL) is degassed by bubbling N2 through the solution. A solution of 1 (27 mg, 24 µmol) in DCM (6 mL) is degassed by bubbling N$_2$ through the solution. While N2 is still bubbled through the solution, the degassed solution of pyrrolidine is added. The weighed Pd(PPh$_3$)$_4$ is dissolved in DCM (1 mL) and 0.9 mL of this solution is added. After 50 min of bubbling of N2, DCM (25 mL) is added and the mixture is washed with aqueous saturated NH$_4$Cl (25 mL). After separation, the aqueous layer is extracted with DCM (2×25 mL). The combined organic layers are dried (Na$_2$SO$_4$) and concentrated. The residue is purified by RP-HPLC (30-90% MeCN (0.1% formic acid) in H$_2$O (0.1% formic acid). The combined fractions are passed through SPE (HCO$_3$) columns and concentrated. After addition of MeCN (50 mL) the mixture is again concentrated. The resulting residue 2 is used in the next step.

The conversion of the reaction can be monitored through LCMS analysis. Column: XBridge BEH C18 Intelligent Speed (IS) Column, 130 Å, 3.5 µm (4.6 mm×20 mm). Mobile phase A: Water (0.1% formic acid), Mobile phase B (0.1% formic acid). Detection with PDA and ESI+. Samples can be prepared by diluting the reaction mixture with MeCN.

(b) To a solution of the above residue 2 in CHCl$_3$ (5 mL) is added a solution of 3 (15 mg, 36 µmol, mw 418 g/mole) in CHCl$_3$ (0.8 mL). The resulting mixture is added to solid EDC.HCl (4.7 mg, 25 µmol), CHCl$_3$ (5 mL) was added and the mixture stirred for 30 minutes. DCM (30 mL) is added and the resulting mixture is washed with water (30 mL). After separation, the aqueous phase is extracted with DCM (30 mL). The combined organic layers are dried (Na$_2$SO$_4$) and concentrated. The residue is purified by RP-HPLC (30-90% MeCN (no acid) in H$_2$O (0.01% formic acid). The HPLC collection tubes are filled with 5% aqueous (NH$_4$) HCO$_3$ before collection. The combined HPLC fractions are extracted with DCM (3×20 mL). The combined organic layers are dried (Na$_2$SO$_4$) and concentrated. The product 4 is obtained as slightly yellow/white oil (21 mg, 16 µmol, mw 1323 g/mole, 67% over two steps).

The conversion of the reaction can be monitored through LCMS analysis. Column: XBridge BEH C18 Intelligent Speed (IS) Column, 130 Å, 3.5 µm (4.6 mm×20 mm). Mobile phase A: Water (0.1% formic acid), Mobile phase B (0.1% formic acid). Detection with PDA and ESI+.

Glycan Remodelling (Anti-DLK1 ADC, ConjA1)

Antibody Preparation

Approximately 60 mg of anti-DLK1 antibody was buffer exchanged into 25 mM Tris/Cl, 150 mM NaCl, pH 8.0 via a G25 desalting column; 4×2.5 mL at 6 mg/mL loaded onto 4×PD10 desalting columns (GE 17085101). The buffer exchanged antibody was then concentrated to at least 25 mg/mL using a Vivaspin 20 centrifugal concentrator (Sigma Z614637). The protein concentration was confirmed as 28.4 mg/mL by A280-320 nm UV analysis using an extinction coefficient of 1.5.

Remodelling Reaction

Glycan remodelling was performed in a single pot reaction overnight (16 hours) at room temperature. The following reaction mixture was prepared with the solutions/reagents added in the order detailed below:

| Solution | Volume (uL) | Concentration Final |
|---|---|---|
| 25 mM Tris/Cl, 150 mM NaCl, pH 8.0 | 663.8 | NA |
| anti-DLK1 antibody in 25 mM Tris/Cl, 150 mM NaCl, pH 8.0 | 2000 | 15 mg/mL |
| 3.5 mg/mL EndoSH in 25 mM Tris/Cl, pH 8.0 | 165.7 | 1% w/w relative to mAb |
| 4.82 mg/mL His-TnGalNAcT in 25 mM Tris/Cl, pH 8.0 | 902.5 | 7.5% w/w relative to mAb |

| Solution | Volume (uL) | Concentration Final |
|---|---|---|
| 1M MgCl$_2$ in MQ water | 38.7 | 10 mM |
| 0.1M 6-N$_3$GalNAc-UDP in MQ water | 96 | 25 Eq relative to mAb |

Protein A Purification Procedure

Protein A bind and elute was performed on a 5 mL HiTrap MabSelect Sure column (GE 11-0034-94). All chromatography steps were performed at 240 cm/hr flow rate using an AKTA Prime plus system. The column was prepared and used as follows:

| Solution | CVs | Notes |
|---|---|---|
| 0.1M NaOH | 3 | Sanitization |
| 25 mM Tris/Cl, 25 mM NaCl, pH 8.0 | 10 | Equilibration |
| anti-DLK1 antibody Sample | As required | Load |
| 0.4M Potassium Phosphate, 0.2% Triton 100, pH 7.0 | 20 | Wash/Endotoxin removal step |
| 25 mM Tris/Cl, 25 mM NaCl, pH 8.0 | 20 | Wash/Triton removal step |
| 0.15M Acetic Acid | As required | Collect peak 0.1 to 0.1 AU |

After protein A affinity purification, a small sample of the product may be reduced with DTT and subsequently subjected to MS analysis. A typical mass spectrum of a successful transfer reaction shows the formation of a one major product of (90% of total heavy chain), resulting from modified galactose transfer to core GlcNAc(Fuc) substituted Ab, and a minor product (±10% of total heavy chain), resulting from modified galactose transfer to core GlcNAc (without Fucose) substituted antibody.

Post Protein a Buffer Exchange

The remodeled & purified anti-DLK1-GalNAc-N3 antibody was then buffer exchanged into phosphate buffered saline (PBS) and concentrated to approximately 16.6 mg/mL using a Vivaspin 20 centrifugal concentrator (Sigma Z614637). The protein A eluate was diluted 1:1 with PBS and then concentrated back to the original volume and this repeated 6 times. The volume was finally reduced to target 16-17 mg/mL and the sample recovered from the device. The protein concentration was confirmed as 16.4 mg/mL by A280-320 nm UV analysis using an extinction coefficient of 1.5 and a total of 2.7 mL was recovered.

Conjugation of 4 to Modified Antibody to Produce ConjA1

Reaction Conditions 2.7 mL of 16.4 mg/mL azido-modified DLK1 antibody (in this example, HuBa-1-3d as described herein)

0.3 mL of 10 mM 4 in Dimethylacetamide

The reaction was mixed thoroughly and left to conjugate overnight (16 hours) at room temperature. The conjugation mixture was filtered through a 0.2 µm PVDF filer (Millipore SLGV033RS) prior to final purification and formulation.

Purification of ConjA1

The filtered conjugation mixture was purified using a Vivaspin 20 centrifugal concentrator (Sigma Z614637). The conjugation mixture was diluted 1:1 with 30 mM Histidine HCl, 200 mM Sorbitol, pH 6.0 and the concentrated back to the original volume. This was repeated 12 times before the purified ADC bulk was recovered from the centrifugal device.

The protein concentration was determined by quantitative SEC analysis using a calibration curve of the antibody and the conjugate diluted to approximately 5 mg/mL with additional 30 mM Histidine HCl, 200 mM Sorbitol, pH 6.0. Tween 20 was added to 0.02% w/v from a 1% stock in 30 mM Histidine HCl, 200 mM Sorbitol, pH 6.0 and the concentration retested by quantitative SEC analysis. A sample was taken for testing and the remainder split into 1 mL aliquots and frozen at −80 C.

Analysis of the product showed the following properties:

Clear, colourless, particulate free 5.17 [protein] by SEC

Average DAR of 1.87 (by RP chromatography)

0.09 EU/mg endotoxin

≤4.5% free drug-linker pH 6.06

Glycan Remodelling (Anti-KAAG1 ADC, ConjA2)

Antibody Preparation

Approximately 150 mgs of anti-KAAG1 (approximately 25 mL at 6.13 mg/mL in PBS pH 7.4) was buffer exchanged into 25 mM Tris/Cl, 150 mM NaCl, pH 8.0 and concentrated to >25 mg/mL using Vivaspin 20 centrifugal concentrators (Sigma Z614637). Initially, the antibody was concentrated to 12 mL and then diluted 1:1 with 25 mM Tris/Cl, 150 mM NaCl, pH 8.0 and then concentrated back to 12 mL and this process repeated 6 times. Finally, the buffer exchanged stock was further concentrated to 6 mL. The protein concentration was determined by A280-320 nm UV analysis using an extinction coefficient of 1.5 and then diluted to 25 mg/mL with 25 mM Tris/Cl, 150 mM NaCl, pH 8.0.

Remodelling Reaction

Glycan remodelling was performed in a single pot reaction overnight (16 hours) at room temperature. The following reaction mixture was prepared with the solutions/reagents added in the order detailed below:

| Solution | Volume (uL) | Concentration Final |
|---|---|---|
| 25 mM Tris/Cl, 150 mM NaCl, pH 8.0 | 893 | NA |
| Anti-KAAG1 mAb in 25 mM Tris/Cl, 150 mM NaCl, pH 8.0 | 6000 | 15 mg/mL |
| 3.5 mg/mL EndoSH in 25 mM Tris/Cl, pH 8.0 | 428.4 | 1% w/w relative to mAb |
| 4.82 mg/mL His-TnGalNAcT in 25 mM Tris/Cl, pH 8.0 | 2330 | 7.5% w/w relative to mAb |
| 1M MgCl2 in MQ water | 100.2 | 10 mM |
| 0.1M 6-N3GalNAc-UDP in MQ water | 250 | 25 Eq relative to mAb |

Protein A Purification Procedure

Protein A bind and elute was performed on a 4.7 mL HiScreen MabSelect Sure column (GE 28-9269-77). All chromatography steps were performed at 240 cm/hr flow rate using an AKTA Prime plus system. The column was prepared and used as follows:

| Solution | CVs | Notes |
|---|---|---|
| 0.1M NaOH | 3 | Sanitization |
| 25 mM Tris/Cl, 25 mM NaCl, pH 8.0 | 10 | Equilibration |
| Antibody Sample | As required | Load |
| 0.4M Potassium Phosphate, 0.2% Triton 100, pH 7.0 | 20 | Wash/Endotoxin removal step |

-continued

| Solution | CVs | Notes |
|---|---|---|
| 25 mM Tris/Cl, 25 mM NaCl, pH 8.0 | 20 | Wash/Triton removal step |
| 0.15M Acetic Acid | As required | Collect peak 0.1 to 0.1 AU |

After protein A affinity purification, a small sample of the product may be reduced with DTT and subsequently subjected to MS analysis. A typical mass spectrum of a successful transfer reaction shows the formation of a one major product of (90% of total heavy chain), resulting from modified galactose transfer to core GlcNAc(Fuc) substituted Ab, and a minor product (±10% of total heavy chain), resulting from modified galactose transfer to core GlcNAc (without Fucose) substituted antibody.

Post Protein A Buffer Exchange

The protein A eluate containing the remodeled/purified Ab-GalNAc-N3 was pH adjusted with the addition of 1.5M Tris base at 3.2% v/v and then buffer exchanged into PBS and concentrated to ≈17 mg/mL using Vivaspin 20 centrifugal concentrators (Sigma Z614637). Initially, the pH adjusted pool was diluted 1:1 PBS and then concentrated back to the original volume and this process repeated 6 times. Finally, the buffer exchanged stock was further concentrated to target≈17 mg/mL. The protein concentration was confirmed at 16.5 mg/mL by A280-320 nm UV analysis using an extinction coefficient of 1.5; a total of 7.9 mL was recovered for a yield of 88%.

Conjugation of 4 to Modified Antibody to Produce ConjA2

To 7.9 mL of 16.5 mg/mL Ab-GalNAc-N3 (Ab=3A4, as described herein) was added 0.788 mL of 10 mM PL1601 in DMF (10% final v/v DMF). The reaction was mixed thoroughly and left to conjugate overnight (16 hours) at room temperature. The conjugation mixture was filtered through a 0.22 µm PES filter (Millipore SLGV033RS) prior to final purification and formulation.

Purification of ConjA2

The filtered conjugation mixture was purified by constant-volume diafiltration using a 30 kDa Pellicon 3 membrane at ≈50 g/m² of membrane area, a crossflow of 5.0±0.25 L/min/m2, TMP of 1.0±0.2 bar and a total of 12 diavolumes of buffer exchange into PBS pH7.4. The diafiltered pool was recovered from the UFDF and filtered through a 0.22 µm PES membrane filter (Millipore SLGV033RS) into sterile eppendorfs. The protein concentration was determined by A280-320 nm UV analysis using an extinction coefficient of 1.5 and was determined to be 4.9 mg/mL. A sample was taken for testing and the remainder stored at 4° C.

Analysis of the product showed the following properties:
Clear, colourless, particulate free
4.9 mg/ml [protein] by A280/330 nm spectroscopy
Average DAR of 1.9 (by RP chromatography)
0.07 EU/mg endotoxin
3% free drug-linker
98.3% monomer by sixe exclusion chromatography Glycan Remodelling (Anti-Mesothelin ADC, ConjA3)

Antibody Preparation

Approximately 60 mg of anti-Mesothelin antibody is buffer exchanged into 25 mM Tris/Cl, 150 mM NaCl, pH 8.0 via a G25 desalting column; 4×2.5 mL at 6 mg/mL loaded onto 4×PD10 desalting columns (GE 17085101). The buffer exchanged antibody is then concentrated to at least 25 mg/mL using a Vivaspin 20 centrifugal concentrator (Sigma Z614637). The protein concentration is confirmed by A280-320 nm UV analysis using an extinction coefficient of 1.5.

Remodelling Reaction

Glycan remodelling is performed in a single pot reaction overnight (16 hours) at room temperature. The following reaction mixture is prepared with the solutions/reagents added in the order detailed below:

| Solution | Volume (uL) | Concentration Final |
|---|---|---|
| 25 mM Tris/Cl, 150 mM NaCl, pH 8.0 | 663.8 | NA |
| anti-Mesothelin antibody in 25 mM Tris/Cl, 150 mM NaCl, pH 8.0 | 2000 | 15 mg/mL |
| 3.5 mg/mL EndoSH in 25 mM Tris/Cl, pH 8.0 | 165.7 | 1% w/w relative to mAb |
| 4.82 mg/mL His-TnGalNAcT in 25 mM Tris/Cl, pH 8.0 | 902.5 | 7.5% w/w relative to mAb |
| 1M MgCl$_2$ in MQ water | 38.7 | 10 mM |
| 0.1M 6-N$_3$GalNAc-UDP in MQ water | 96 | 25 Eq relative to mAb |

Protein A Purification Procedure

Protein A bind and elute is performed on a 5 mL HiTrap MabSelect Sure column (GE 11-0034-94). All chromatography steps are performed at 240 cm/hr flow rate using an AKTA Prime plus system. The column is prepared and used as follows:

| Solution | CVs | Notes |
|---|---|---|
| 0.1M NaOH | 3 | Sanitization |
| 25 mM Tris/Cl, 25 mM NaCl, pH 8.0 | 10 | Equilibration |
| anti-Mesothelin antibody Sample | As required | Load |
| 0.4M Potassium Phosphate. 0.2% Triton 100, pH 7.0 | 20 | Wash/Endotoxin removal step |
| 25 mM Tris/Cl, 25 mM NaCl, pH 8.0 | 20 | Wash/Triton removal step |
| 0.15M Acetic Acid | As required | Collect peak 0.1 to 0.1 AU |

After protein A affinity purification, a small sample of the product may be reduced with DTT and subsequently subjected to MS analysis. A typical mass spectrum of a successful transfer reaction shows the formation of a one major product of (90% of total heavy chain), resulting from modified galactose transfer to core GlcNAc(Fuc) substituted Ab, and a minor product (±10% of total heavy chain), resulting from modified galactose transfer to core GlcNAc (without Fucose) substituted antibody.

Post Protein a Buffer Exchange

The remodeled & purified anti-Mesothelin-GalNAc-N3 antibody is then buffer exchanged into phosphate buffered saline (PBS) and concentrated to approximately 16.6 mg/mL using a Vivaspin 20 centrifugal concentrator (Sigma Z614637). The protein A eluate is diluted 1:1 with PBS and then concentrated back to the original volume and this is repeated 6 times. The volume is finally reduced to target 16-17 mg/mL and the sample recovered from the device. The protein concentration is confirmed by A280-320 nm UV analysis using an extinction coefficient of 1.5.

Conjugation of 4 to Modified Antibody to Produce ConjA3

Reaction Conditions 2.7 mL of ~15 mg/mL azido-modified anti-Mesothelin antibody 0.3 mL of 10 mM 4 in Dimethylacetamide The reaction is mixed thoroughly and left to conjugate overnight (16 hours) at room temperature. The conjugation mixture is filtered through a 0.2 μm PVDF filer (Millipore SLGV033RS) prior to final purification and formulation.

Purification of ConjA3

The filtered conjugation mixture is purified using a Vivaspin 20 centrifugal concentrator (Sigma Z614637). The conjugation mixture is diluted 1:1 with 30 mM Histidine HCl, 200 mM Sorbitol, pH 6.0 and then concentrated back to the original volume. This is repeated 12 times before the purified ADC bulk is recovered from the centrifugal device.

The protein concentration is determined by quantitative SEC analysis using a calibration curve of the antibody and the conjugate diluted to approximately 5 mg/mL with additional 30 mM Histidine HCl, 200 mM Sorbitol, pH 6.0. Tween 20 is added to 0.02% w/v from a 1% stock in 30 mM Histidine HCl, 200 mM Sorbitol, pH 6.0 and the concentration retested by quantitative SEC analysis. A sample is taken for testing and the remainder split into 1 mL aliquots and frozen at −80 C.

In Vitro Cytotoxicity of ConjA1

Flasks of either Lu135 cell or SK-N-FI cells were trypsin treated and the liberated cells were washed and re-suspended in fresh medium. The cell density was determined by mixing 1:1 with Trypan blue (0.4% (w/v) Sigma TB154) and counting clear/blue (live/dead) cells with a Luna II automated cell counter (Logos Biosystems). The cell suspension was diluted to the required seeding density (20×104/m1), dispensed into white 96-well flat bottomed microplates (50 μl/well) and incubated overnight.

A stock solution (1 ml) of ConjA1 (20 μg/ml) was made by dilution of filter-sterile ConjA1 into the same cell culture medium. A set of 8× 10-fold dilutions of stock ConjA1 was made in a sterile 24-well plate by serial transfer of 100 μl into 900 μl of cell culture medium. Each ConjA1 dilution was dispensed, 50 μl/well, into 4 replicate wells of the 96-well plate, containing cells suspension. Control wells received the same volume of culture medium only.

After the ConjA1 exposure period, cell viability was measured by Promega CellTiter-Glo by adding 100 μl/well, agitate for 2 mins and read on the Envision using the Luminescence protocol. Data were analysed using Graphpad Prism software.

The $EC_{50}$ of ConjA1 against Lu-135 cells was found to be 0.01765 μg/mL. The $EC_{50}$ of the ADC control was 0.5326 μg/mL (see FIG. 1A*).

The $EC_{50}$ of ConjA1 against SK-N-FI cells was found to be 0.1565 μg/mL. The $EC_{50}$ of the ADC control was $5×10^5$ μg/mL (see FIG. 1B*).

*In both FIGS. 1A*1B, ▼ is ConjA1 and ● is an otherwise identical ADC control comprising the non-DLK1 specific antibody B12).

In Vivo Efficacy Studies with ConjA1

In vivo anti-tumor activity in liver cancer patient-derived xenograft (PDX) LI1097 model LI1097 seed tumours were revived subcutaneously in NOD/SCID mice, and maintained subcutaneously in BALB/c nude mice before implantation. When the tumour volumes reached 700-1500 mm³, tumours were collected and cut into pieces of about 2-3 mm3 in diameter. The tumours or tumour pieces were washed with ice cold RPM11640 media (without serum) and subsequently placed into ice cold media for use.

The skin of five-to-six week old, female BALB/c nude mice was disinfected at the right flank by iodophor before tumour implantation. Each mouse was inoculated without anesthesia, subcutaneously at the right upper flank with one primary human liver cancer LI1097 tumour fragment for tumour development.

After tumour inoculation, the animals were checked daily for morbidity and mortality. Tumour size was measured by caliper twice weekly in two dimensions. The tumour volume was expressed in mm³ using the formula: TV=0.5 a×b2 where a and b are the long and short diameters of the tumour, respectively.

On study day 12, mice were randomised into 5 groups of 8 mice each; the mean tumour volume was ~170 mm³ across the cohort. Mice were dosed with the test agents on study day 13 (day 1, indicated by vertical dotted line in the graph). Test mice in this study received a single dose of their allocated test article and dose level on day 1 and tumour growth was monitored thereafter, up to day 51.

Figure 2:
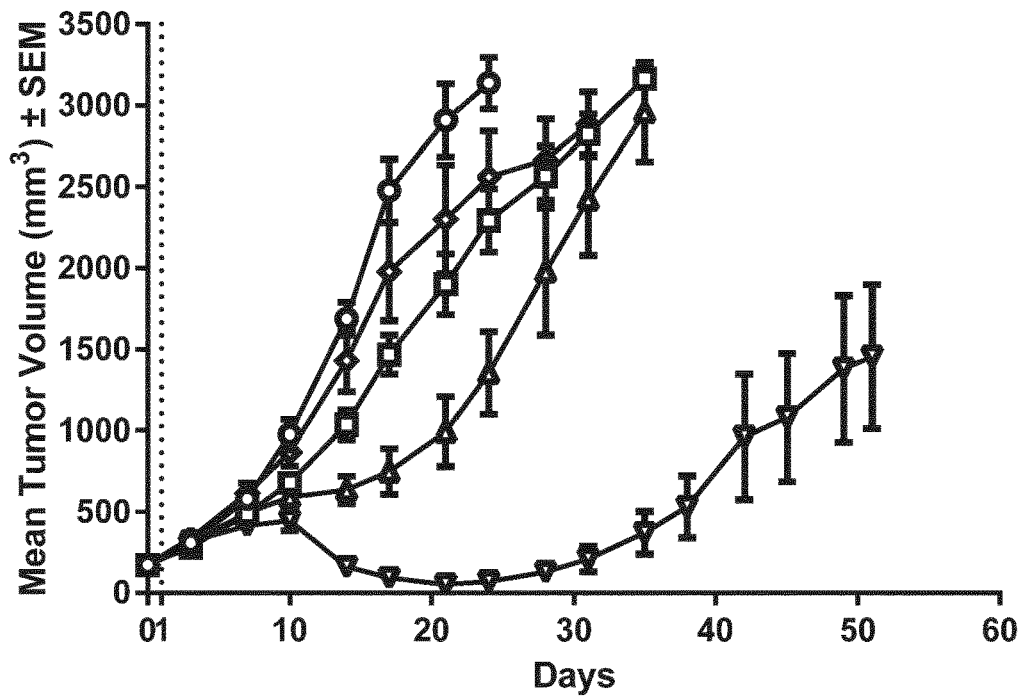
FIG. 2 shows the in vivo efficacy of a conjugate according to the first aspect of the invention.
Figure 2:
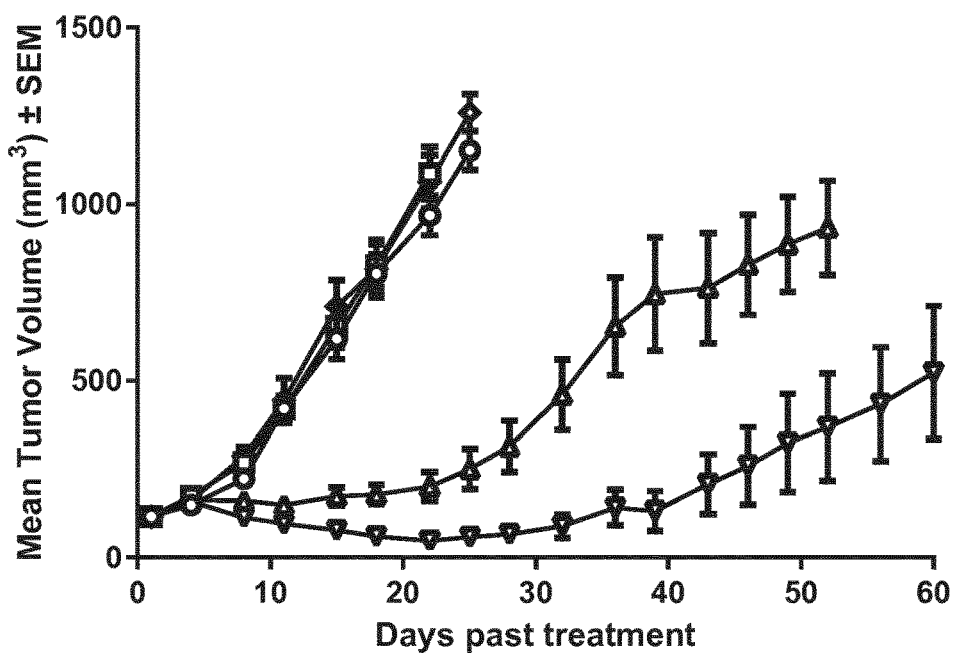

The results are shown in FIG. 2A, where:

○=vehicle, qd×1

◇=ADC control using non-DLK1 specific antibody B12, 1 mg/kg, qd×1

☐=ConjA1, 0.1 mg/kg, qd×1

Δ=ConjA1, 0.3 mg/kg, qd×1

▼=ConjA1, 1.0 mg/kg, qd×1

As is clear from FIG. 2A, ConjA1 at 1.0 mg/kg led to the greatest slowing of tumour growth, followed by the ConjA1 at 0.3 mg/kg. Moreover, at the highest dose tested, ConjA1 resulted in 3/8 PR and 2/8 CR, while none of the mice treated with the vehicle or the isotype-control ADC (1 mg/kg, single dose) had any PR, CR or TFS.

In Vivo Anti-Tumor Activity in the Neuroblastoma SK-N-FI Xenograft Model

Female, NOD-SCID mice were six weeks old on day of implant. SK-N-FI cells were harvested during log phase growth and resuspended in phosphate buffered saline with 50% matrigel. Using a 26 G syringe, 100 μL ($3×10^6$ cells) of the cell suspension mixture was subcutaneously injected into the right flank of each mouse. Animals were examined twice per week with their body weight and tumor size. Tumor size was measured using digital calipers and calculated according to the following expression:

Tumor volume (mm³)=(minor axis) 2×(major axis)× π/6

Eighteen days after transplant of the cancer cells, 50 mice whose tumor volume was between 99.0 mm³ and 155.2 mm³ (average 116.2 mm³) were divided into 5 groups (N=10 in each group). On the dosing day, test subjects were administrated by intravenous injection from tail vein. The end point of the study was set as when each tumor reaches the endpoint volume of 1000 mm³ or at the end of the study (60 days after dosing), whichever came first.

The results are shown in FIG. 2B, where:

◇=vehicle, qd×1

○=ADC control using non-DLK1 specific antibody B12, 0.5 mg/kg, qd×1

☐=ADC control using non-DLK1 specific antibody B12, 1 mg/kg, qd×1

Δ=ConjA1, 0.5 mg/kg, qd×1

▼=ConjA1, 1.0 mg/kg, qd×1

As is clear from FIG. 2B, ConjA1 at 1.0 mg/kg led to the greatest slowing of tumour growth, followed by the ConjA1 at 0.5 mg/kg.

In the human neuroblastoma-derived SK-N-FI xenograft model a single dose of ConjA1 at 0.5 or 1 mg/kg showed dose-dependent anti-tumor activity compared to the vehicle- and isotype control ADC-treated mice.

At the highest dose tested, ConjA1 resulted in 1/9 partial responders (PR) and 4/9 complete responder (CR), one of which was a tumor-frees survivor (TFS) at the end of the study on day 60 (one animal of the initial 10 in this group was excluded fro excluded from the final figures for treatment-unrelated reasons).

Rat Toxicology Study

Rat toxicology study (off-target toxicity assessment, tested ADC does not bind rat Dlk-1)

Method ConjA1 was evaluated in a single intravenous dose rat tolerability study. Male sprague-dawley rats (n=3/group) were dosed at 5 mg/kg on day 1, with necropsy on day 21 following dosing. Bodyweights and food consumption were monitored frequently with in-life sampling for clinical pathology (blood on days 8 and 21) and repeated sampling for pharmacokinetics. At necropsy, macroscopic observations were taken with selected organs weighed and retained for possible histopathology.

Results

ConjA1 was clinically well tolerated at 5 mg/kg with no marked adverse clinical signs. Bodyweight gain was reduced, with the animals being around 15% lighter than the control group at the end of the study. White blood cell count was reduced on day 8 (neutrophils reduced by around 95% compared to concurrent control), with evidence of recovery by day 22.

Overall Conclusion

ConjA1 was well stable, well tolerated and showed a favorable pharmacokinetic profile in the rat with a half-life of 9 days at 5 mg/kg. This suggest that the MTD in rats is at least 5 mg/kg or higher.

In Vitro Cytotoxicity in A204 and Hep3B Cells in 2D and 3D Cell Culture

Materials & Methods

Cells were seeded in onco-media (RPMI, 5% FBS, 2 mM L-alanyl-L-glutamine, 1 mM sodium pyruvate and 1% penicillin/streptomycin) in 384-well Elplasia plates pre-coated with pHEMA.

The ADC, ConjA1, and B12-1601 compounds were added 24 hours post cell seeding, with a starting concentration of 10 mg/mL, a 10-fold serial dilution across 9 concentrations in quadruplicate. The incubation times with the ADC's compounds were 5 days in 2D- and 7 days in 3D-cultures with media exchanges every 3 days, for a total of 14.

At the end of incubation period, cells were lysed and analyzed to determine cell viability. Cell proliferation endpoint was analyzed as Percent of Control (POC) using the following formula:

POC=relative cell count (compound wells)/relative cell count (vehicle control wells)×100%

Data were analysed using Graphpad Prism software.

Results

Figure 3:
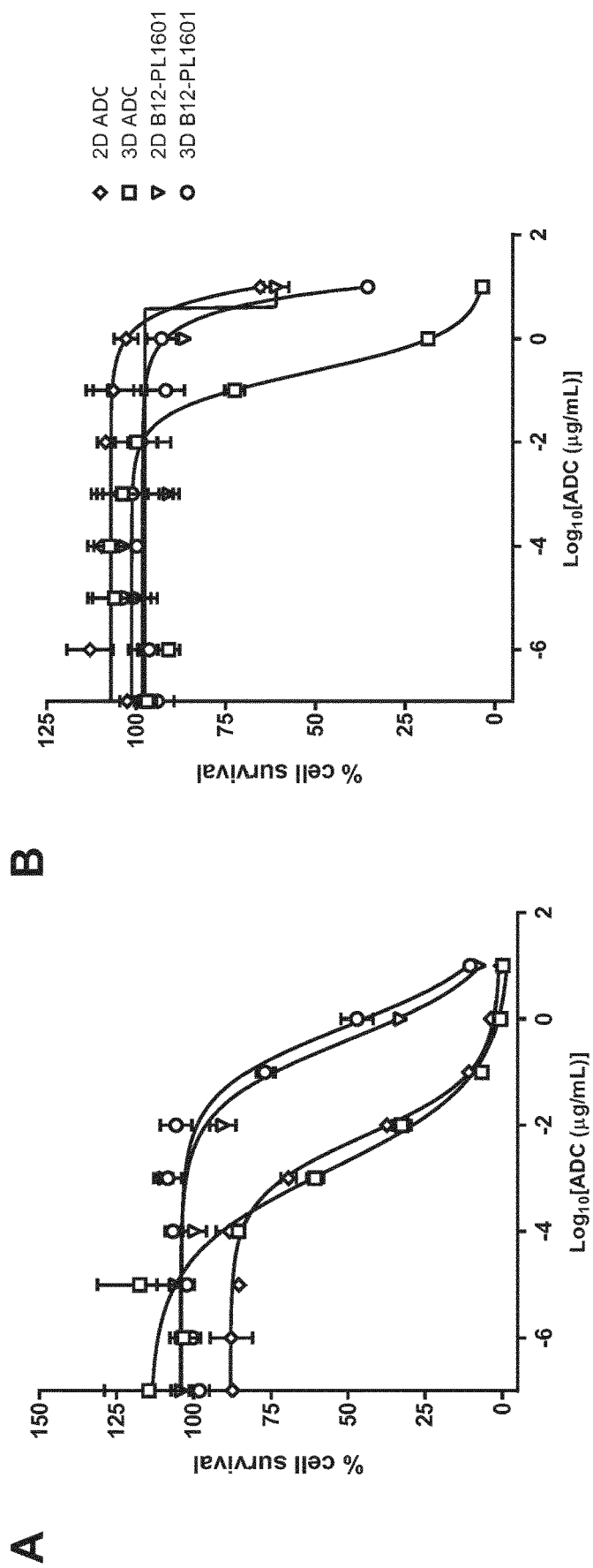
FIG. 3 shows in vitro cytotoxicity in A204 and Hep3B cells in 2D and 3D cell culture of a conjugate according to the first aspect of the invention.

FIG. 3 shows data from in vitro cytotoxicity in A204 and Hep3B cells in 3D cell culture:

FIG. 3A is the A204 cell data [$IC_{50}$ 3 D ADC=0.001460 µg/ml, $IC_{50}$ 3 D B12-PL1601=0.7662 µg/ml, $IC_{50}$ 2D ADC=0.006399 µg/ml, $IC_{50}$ 3D B12-PL1601=0.4059 µg/m];

FIG. 3B is the Hep3B cell data [$IC_{50}$ 3 D ADC=0.2271 µg/ml, $IC_{50}$ 3 D B12-PL1601=~432.6 µg/ml, $IC_{50}$ 2D ADC=~59.29 µg/ml, $IC_{50}$ 2D B12-PL1601=~3.957 µg/ml].

In Vitro Cytotoxicity of ConjA2

Flasks of either SN12C and MDA-MB-231 FI cells were trypsin treated and the liberated cells were washed and re-suspended in fresh medium. The cell density was determined by mixing 1:1 with Trypan blue (0.4% (w/v) Sigma TB154) and counting clear/blue (live/dead) cells with a Luna II automated cell counter (Logos Biosystems). The cell suspension was diluted to the required seeding density ($20 \times 10^4$/ml), dispensed into white 96-well flat-bottomed microplates (50 µl/well), and incubated overnight.

A stock solution (1 ml) of ConjA2 (20 µg/ml) was made by dilution of filter-sterile ConjA2 into the same cell culture medium. A set of 8× 10-fold dilutions of stock ConjA2 was made in a sterile 24-well plate by serial transfer of 100 µl into 900 µl of cell culture medium. Each ConjA2 dilution was dispensed, 50 µl/well, into 4 replicate wells of the 96-well plate, containing cells suspension. Control wells received the same volume of culture medium only.

After the ConjA2 exposure period, cell viability was measured by Promega CellTiter-Glo by adding 100 µl/well, agitate for 2 mins and read on the Envision using the Luminescence protocol. Data were analysed using Graphpad Prism software.

The $EC_{50}$ of ConjA2 against SN12C cells was found to be 0.0663 µg/mL. The $EC_{50}$ of the ADC control was not detectable (see FIG. 4A*).

The $EC_{50}$ of ConjA2 against MDA-MB-231 cells was found to be 0.226 µg/mL. The $EC_{50}$ of the ADC control was again not detectable (see FIG. 4B*).

Figure 4:
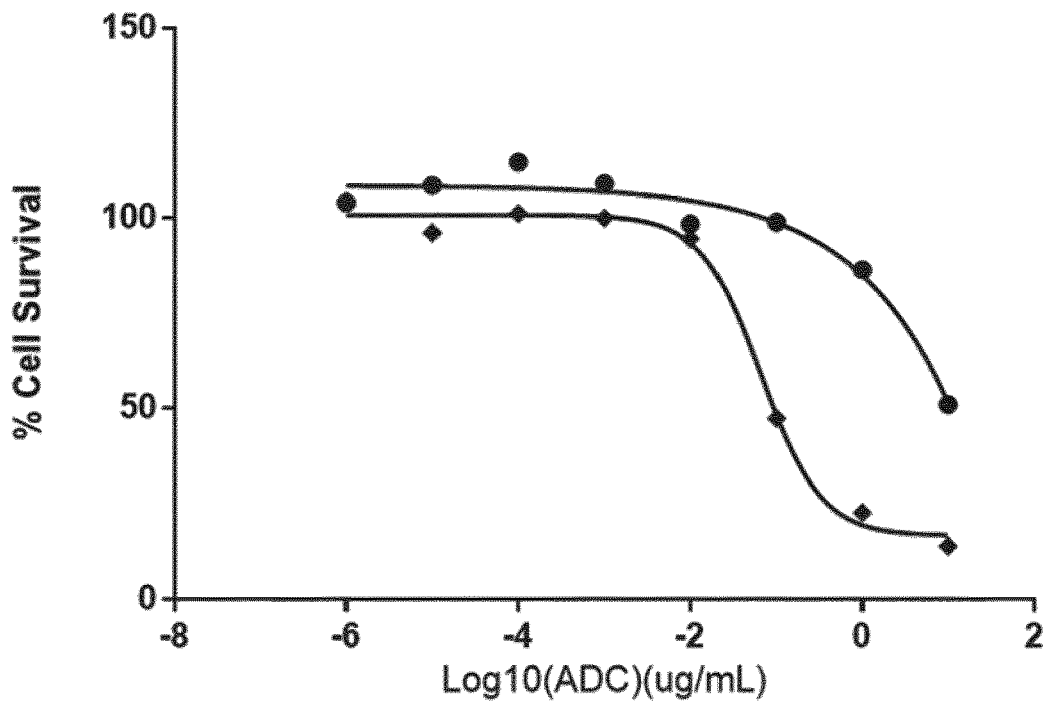
FIG. 4 shows the in vitro cytotoxicity of a conjugate according to the second aspect of the invention.
Figure 4:
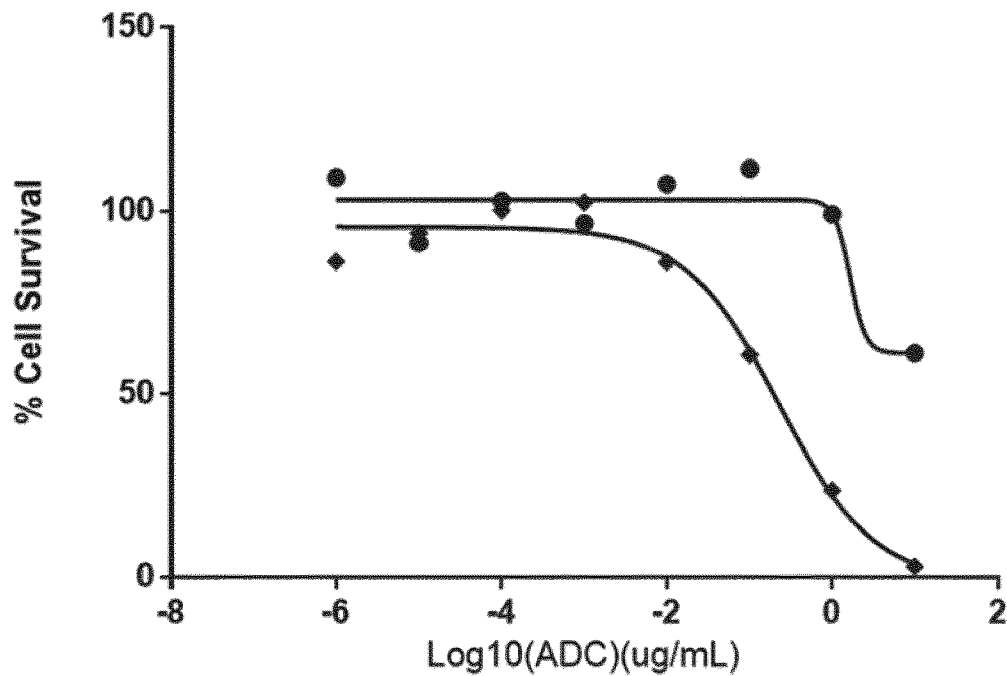

In both FIGS. 4A & 4B, ◆ is ConjA2 and ● is an otherwise identical ADC control comprising the non-KAAG1 specific antibody B12).

In Vivo Efficacy Study of ConjA2

Female athymic nude mice (Crl:NU(Ncr)-Foxn1nu, Charles River) were eight weeks old with a body weight (BW) range of 20.7-31.2 g on Day 1 of the study.

On the day of implant, MDA-MB-231 tumor cells used for implantation were harvested during log phase growth and resuspended in phosphate-buffered saline (PBS) at $5 \times 10^7$ cells/mL. Each mouse was injected subcutaneously (s.c.) in the right flank with $5 \times 10^6$ cells (0.1 mL cell suspension) and tumors were monitored as their volumes approached the target range of 100 to 150 mm³. Tumors were measured in two dimensions using calipers, and volume was calculated using the formula:

Tumor Volume (mm³)=w²×l/2 where w=width and l=length, in mm, of the tumor. Tumor weight may be estimated with the assumption that 1 mg is equivalent to 1 mm³ of tumor volume.

Sixteen days after tumor implantation, designated as Day 1 of the study, the animals were sorted into groups each consisting of 8 mice with individual tumor volumes of 108 to 144 mm³ and group mean tumor volumes of 112.5-123.8 mm³. On Day 1 of the study, all treatments were administered intravenously (i.v.) in a single injection (qd×1) via tail vein injection in a dosing volume of 0.2 mL per 20 grams of body weight (10 mL/kg), scaled to the body weight of each individual animal. Tumors were measured using calipers twice per week, and each animal was euthanized when its tumor reached the endpoint volume of 1500 mm³ or at the end of the study, whichever came first. The study ended on Day 59.

Figure 5:
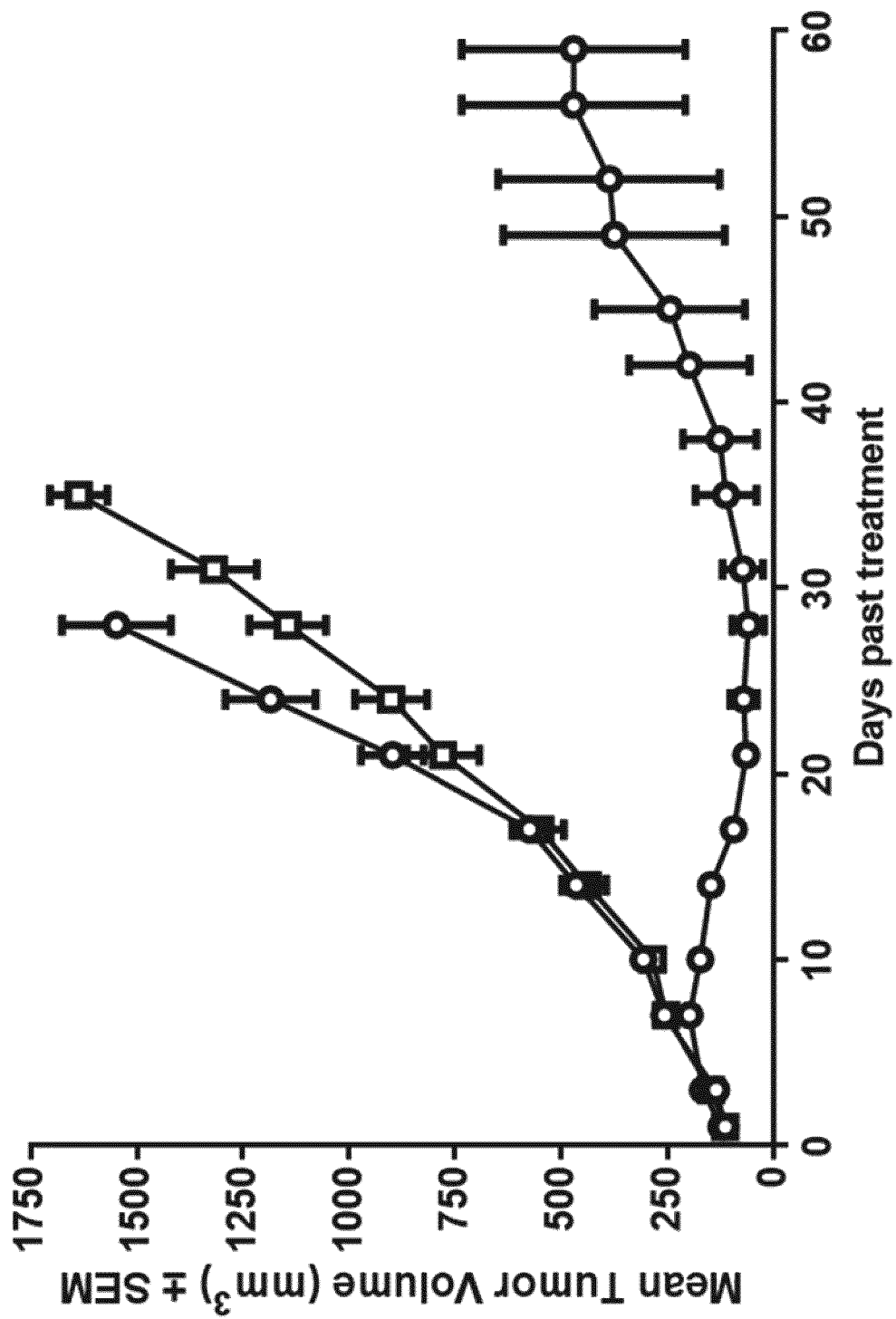
FIG. 5 shows the in vivo efficacy of a conjugate according to the second aspect of the invention.

The results are shown in FIG. 5, where:
○=vehicle, qd×1 (upper line)
□=ADC control using non-KAAG1 specific antibody B12, 0.6 mg/kg, qd×1
◇=ConjA2, 0.6 mg/kg, qd×1 (lower line)

As is clear from FIG. 5, ConjA2 at 0.6 mg/kg led to significant slowing of tumour growth.

In Vivo Anti-Tumor Activity of ConjA2 in SN12C Xenograft Model

Female severe combined immunodeficient mice (Fox Chase SCID®, CB17/lcr-Prkdcscid/IcrlcoCrl, Charles River) were nine weeks old with a body weight (BW) range of 15.4 to 22.2 g on Day 1 of the study.

On the day of tumor implant, each test mouse received 5×106 SN12C cells (0.1 mL cell suspension in 50% Matrigel® Matrix (Corning®) in phosphate buffered saline) implanted subcutaneously in the right flank. Tumor growth was monitored as the average size approached the target range of 100 to 150 mm$^3$. Tumors were measured in two dimensions using calipers, and volume was calculated using the formula:

Tumor Volume (mm$^3$)=w2×l/2 where w=width and l=length, in mm, of the tumor. Tumor weight may be estimated with the assumption that 1 mg is equivalent to 1 mm$^3$ of tumor volume.

Twenty-three days after tumor implantation, designated as Day 1 of the study, the animals were sorted into nine groups (n=8) with individual tumor volumes of 108 to 172 mm$^3$ and group mean tumor volumes of 129 mm$^3$.

On Day 1 of the study, all treatments were administered intravenously (i.v.) in a single injection (qd×1) via tail vein injection in a dosing volume of 0.2 mL per 20 grams of body weight (10 mL/kg), scaled to the body weight of each individual animal. Tumors were measured using calipers twice per week, and each animal was euthanized when its tumor reached the endpoint volume of 1000 mm$^3$ or at the end of the study, whichever came first. The study ended on Day 60.

Figure 6:
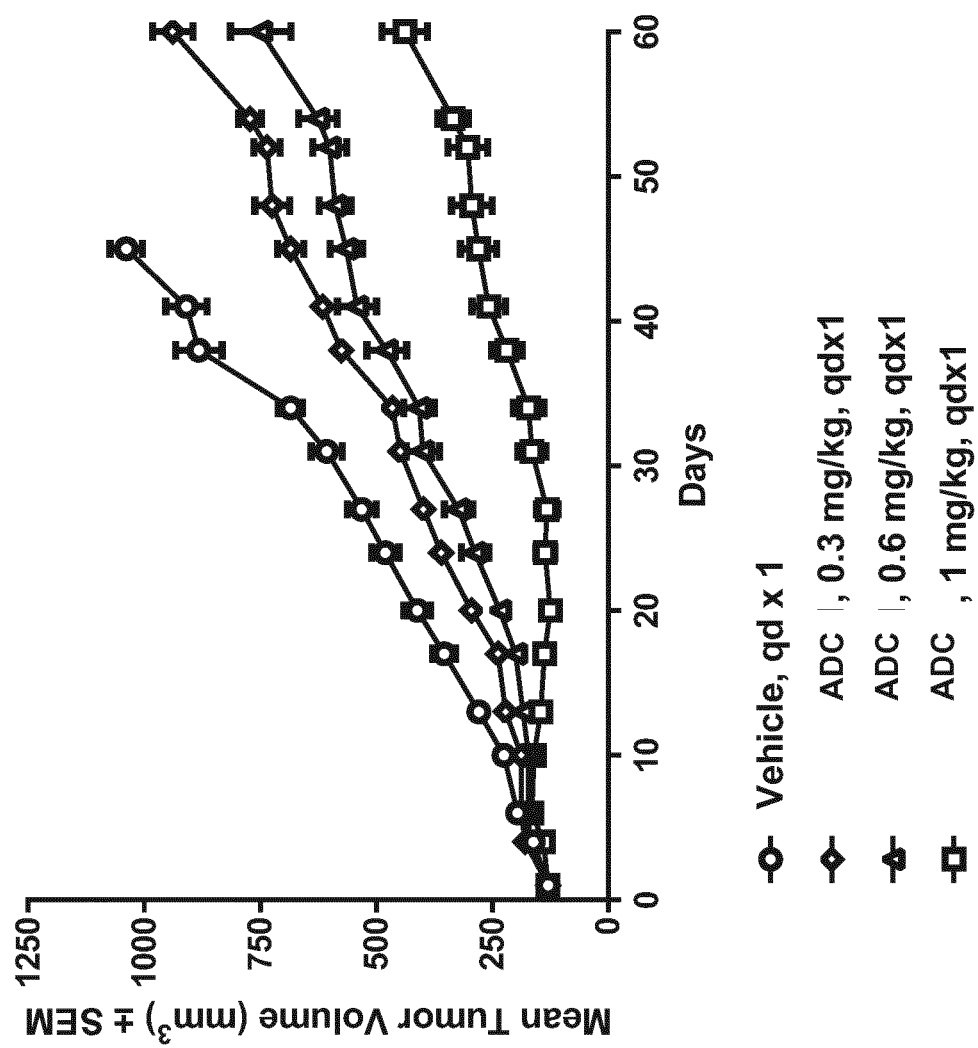
FIG. 6 shows the in vivo anti-tumor activity in SN12C xenograft model of a conjugate according to the second aspect of the invention.

The data is shown in FIG. 6, where it can be seen that administration of the ADC (ConjA2) reduced tumour growth in a dose-dependent manner.

In Vitro Cytotoxicity

Flasks of either OVCAR3, CAPAN-2 or HPAC cells are trypsin treated and the liberated cells are washed and resuspended in fresh medium. The cell density is determined by mixing 1:1 with Trypan blue (0.4% (w/v) Sigma TB154) and counting clear/blue (live/dead) cells with a Luna II automated cell counter (Logos Biosystems). The cell suspension is diluted to the required seeding density (20×104/ml), dispensed into white 96-well flat bottomed microplates (50 μl/well) and incubated overnight.

A stock solution (1 ml) of ConjA3 (20 μg/ml) is made by dilution of filter-sterile ConjA3 into the same cell culture medium. A set of 8× 10-fold dilutions of stock ConjA3 is made in a sterile 24-well plate by serial transfer of 100 μl into 900 μl of cell culture medium. Each ConjA3 dilution is dispensed, 50 μl/well, into 4 replicate wells of the 96-well plate, containing cells suspension. Control wells receive the same volume of culture medium only.

After the ConjA3 exposure period, cell viability is measured by Promega CellTiter-Glo by adding 100 μl/well, agitate for 2 mins and read on the Envision using the Luminescence protocol. Data are analysed using Graphpad Prism software.

In Vivo Efficacy Study of ConjA3

In Vivo Anti-Tumor Activity in a OVCAR3 Model

Seed tumours are revived subcutaneously in NOD/SCID mice, and maintained subcutaneously in BALB/c nude mice before implantation. When the tumour volumes reached 700-1500 mm$^3$, tumours are collected and cut into pieces of about 2-3 mm3 in diameter. The tumours or tumour pieces are washed with ice cold RPM11640 media (without serum) and subsequently placed into ice cold media for use.

The skin of five-to-six week old, female BALB/c nude mice is disinfected at the right flank by iodophor before tumour implantation. Each mouse is inoculated without anesthesia, subcutaneously at the right upper flank with one tumour fragment for tumour development.

After tumour inoculation, the animals are checked daily for morbidity and mortality. Tumour size is measured by caliper twice weekly in two dimensions. The tumour volume is expressed in mm$^3$ using the formula: TV=0.5 a×b2 where a and b are the long and short diameters of the tumour, respectively.

On study day 12, mice are randomised into 5 groups of 8 mice each; the target mean tumour starting volume is ~170 mm$^3$ across the cohort. Mice are dosed with the test agents on study day 13. Test mice in this study receive a single dose of their allocated test article and dose level on day 1 and tumour growth is monitored thereafter, up to day 51.

SEQUENCES

| SEQUENCES |
|---|
| SEQ ID NO. 1 [HuBa-1-3d VH, CDR underline]<br>QVQLVQSGAEVKKPGASVKVSCKGSGYTFT<u>DYAMH</u>WVRQAPGQGLEWIG<u>VISTYYGNTN</u><br><u>YNQKFKG</u>KATMTVDKSTSTAYMELRSLRSDDTAVYYCAR<u>GGLREYYYAMDY</u>WGQGTMVT<br>VSS |
| SEQ ID NO. 2 [HuBa-1-3d VL, CDR underline]<br>DIVMTQSPDSLAVSLGERATINC<u>KSSQSLLNSSNQKNYLA</u>WYQQKPGQPPKLLVY<u>FASTRE</u><br><u>S</u>GVPDRFSGSGSGTDFTLTISSLQAEDVAVYYC<u>QQHYSTPPT</u>FGQGTKLEIK |
| SEQ ID NO. 3 [HuBa-1-3d Heavy Chain]<br>QVQLVQSGAEVKKPGASVKVSCKGSGYTFTDYAMHWVRQAPGQGLEWIGVISTYYGNTN<br>YNQKFKGKATMTVDKSTSTAYMELRSLRSDDTAVYYCARGGLREYYYAMDYWGQGTMVT<br>VSSASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELLG<br>GPSVFLFPPKPKDTLMISRTPEVTCVVVDVSHEDPEVKFNWYVDGVEVHNAKTKPREEQY<br><u>N*</u>STYRVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDKSRW<br>QQGNVFSCSVMHEALHNHYTQKSLSLSPG<br><u>N*</u> indicates Asn297 |

-continued

SEQUENCES

SEQ ID NO. 4 [HuBa-1-3d Light Chain]
DIVMTQSPDSLAVSLGERATINCKSSQSLLNSSNQKNYLAWYQQKPGQPPKLLVYFASTRE
SGVPDRFSGSGSGTDFTLTISSLQAEDVAVYYCQQHYSTPPTFGQGTKLEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC SEQ ID NO. 5 [HuBa-1-3d VH CDR1]
DYAMH SEQ ID NO. 6 [HuBa-1-3d VH CDR2]
VISTYYGNTNYNQKFKG SEQ ID NO. 7 [HuBa-1-3d VH CDR3]
GGLREYYYAMDY SEQ ID NO. 8 [HuBa-1-3d VL CDR1]
KSSQSLLNSSNQKNYLA SEQ ID NO. 9 [HuBa-1-3d VL CDR2]
FASTRES SEQ ID NO. 10 [HuBa-1-3d VL CDR3]
QQHYSTPPT SEQ ID NO. 11 [HuBa-1-3d Heavy Chain, terminal K]
QVQLVQSGAEVKKPGASVKVSCKGSGYTFTDYAMHWVRQAPGQGLEWIGVISTYYGNTN
YNQKFKGKATMTVDKSTSTAYMELRSLRSDDTAVYYCARGGLREYYYAMDYWGQGTMVT
VSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
N*STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK
N* indicates Asn297

SEQ ID NO. 12 [Human DLK1, variant 1]
MTATEALLRVLLLLLAFGHSTYGAECFPACNPQNGFCEDDNVCRCHVGWQGPLCDQCVTS
PGCLHGLCGEPGQCICTDGWDGELCDRDVRACSSAPCANNGTCVSLDGGLYECSCAPGY
SGKDCQKKDGPCVINGSPCQHGGTCVDDEGRASHASCLCPPGFSGNFCEIVANSCTPNP
CENDGVCTDIGGDFRCRCPAGFIDKTCSRPVTNCASSPCQNGGTCLQHTQVSYECLCKPE
FTGLTCVKKRALSPQQVTRLPSGYGLAYRLTPGVHELPVQQPEHRILKVSMKELNKKTPLLT
EGQAICFTILGVLTSLVVLGTVGIVFLNKCETWVSNLRYNHMLRKKKNLLLQYNSGEDLAVNI
IFPEKIDMTTFSKEAGDEEI SEQ ID NO. 13 [Human DLK1, variant 2]
MTATEALLRVLLLLLAFGHSTYGAECFPACNPQNGFCEDDNVCRCQPGWQGPLCDQCVT
SPGCLHGLCGEPGQCICTDGWDGELCDRDVRACSSAPCANNRTCVSLDDGLYECSCAPG
YSGKDCQKKDGPCVINGSPCQHGGTCVDDEGRASHASCLCPPGFSGNFCEIVANSCTPN
PCENDGVCTDIGGDFRCRCPAGFIDKTCSRPVTNCASSPCQNGGTCLQHTQVSYECLCKP
EFTGLTCVKKRALSPQQVTRLPSGYGLAYRLTPGVHELPVQQPEHRILKVSMKELNKKTPLL
TEGQAICFTILGVLTSLVVLGTVGIVFLNKCETWVSNLRYNHMLRKKKNLLLQYNSGEDLAV
NIIFPEKIDMTTFSKEAGDEEI SEQ ID NO. 101 [3A4 VH, CDR underline]
QIQLVQSGAEVKKPGASVKVSCKASGYTFTDDYMSWVKQAPGQGLEWIGDINPYNGDTNY
NQKFKGKATLTVDKSTSTAYMELSSLRSEDTAVYYCARDPGAMDYWGQGTLVTVSS SEQ ID NO. 102 [3A4 VL, CDR underline]
DIVMTQTPLSLPVTPGEPASISCRSSQSLLHSNGNTYLEWYLQKPGQSPQLLIYTVSNRFSG
VPDRFSGSGSGTDFTLKISRVEAEDVGVYYCFQGSHVPLTFGQGTKLEIK SEQ ID NO. 103 [3A4 Heavy Chain]
QIQLVQSGAEVKKPGASVKVSCKASGYTFTDDYMSWVKQAPGQGLEWIGDINPYNGDTNY
NQKFKGKATLTVDKSTSTAYMELSSLRSEDTAVYYCARDPGAMDYWGQGTLVTVSSASTK
GPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYN*STYRVV

| SEQUENCES |
|---|

SVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSC
SVMHEALHNHYTQKSLSLSPG
N* indicates Asn297

SEQ ID NO. 104 [3A4 Light Chain]
DIVMTQTPLSLPVTPGEPASISCRSSQSLLHSNGNTYLEWYLQKPGQSPQLLIYTVSNRFSG
VPDRFSGSGSGTDFTLKISRVEAEDVGVYYCFQGSHVPLTFGQGTKLEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

SEQ ID NO. 105 [3A4 VH CDR1]
GYTFTDDYMS

SEQ ID NO. 106 [3A4 VH CDR2]
DIN PYNGDTN

SEQ ID NO. 107 [3A4 VH CDR3]
DPGAMDY

SEQ ID NO. 108 [3A4 VL CDR1]
RSSQSLLHSNGNTYLE

SEQ ID NO. 109 [3A4 VL CDR2]
TVSNRFS

SEQ ID NO. 110 [3A4 VL CDR3]
FQGSHVPLT

SEQ ID NO. 111 [3A4 Heavy Chain, terminal K]
QIQLVQSGAEVKKPGASVKVSCKASGYTFTDDYMSWVKQAPGQGLEWIGDINPYNGDTNY
NQKFKGKATLTVDKSTSTAYMELSSLRSEDTAVYYCARDPGAMDYWGQGTLVTVSSASTK
GPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYN*STYRVV
SVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSC
SVMHEALHNHYTQKSLSLSPGK
N* indicates Asn297

SEQ ID NO. 112 [Human KAAG1]
MDDDAAPRVEGVPVAVHKHALHDGLRQVAGPGAAAAHLPRWPPPQLAASRREAPPLSQR
PHRTQGAGSPPETNEKLTNPQVKEK SEQ ID NO. 113 [3A4-L2 VL, CDR underline]
DVVMTQTPLSLPVTPGEPASISCRSSQSLLHSNGNTYLEWYLQKPGQSPKWYTVSNRFS
GVPDRFSGSGSGTDFTLKISRVEAEDVGVYYCFQGSHVPLTFGQGTKLEIK SEQ ID NO. 114 [3A4-L2 Light Chain]
DVVMTQTPLSLPVTPGEPASISCRSSQSLLHSNGNTYLEWYLQKPGQSPKLLIYTVSNRFS
GVPDRFSGSGSGTDFTLKISRVEAEDVGVYYCFQGSHVPLTFGQGTKLEIKRTVAAPSVFIF
PPSDEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO. 115 [3A4-K4 VL, CDR underline]
DIVMTQSPDSLAVSLGERATINCRSSQSLLHSNGNTYLEWYQQKPGQPPKWYTVSNRFS
GVPDRFSGSGSGTDFTLTISSLQAEDVAVYYCFQGSHVPLTFGQGTKVEIK SEQ ID NO. 116 [3A4-K4 Light Chain]
DIVMTQSPDSLAVSLGERATINCRSSQSLLHSNGNTYLEWYQQKPGQPPKWYTVSNRFS
GVPDRFSGSGSGTDFTLTISSLQAEDVAVYYCFQGSHVPLTFGQGTKVEIKRTVAAPSVFIF
PPSDEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO. 201 [XA4 VH, CDR underline]
QVHLVESGGGVVQPGRSLRLSCVASGITFRIYGMHWVRQAPGKGLEWVAVLWYDGSHEY
YADSVKGRFTISRDNSKNTLYLQMNSLRAEDTAIYYCARDGDYYDSGSPLDYWGQGTLVT
VSS SEQ ID NO. 202 [XA4 VL, CDR underline]
EIVLTQSPATLSLSPGERATLSCRASQSVSSYLAWYQQKPGQAPRLLIYDASNRATGIPARF
SGSGSGTDFTLTISSLEPEDFAVYYCQQRSNWPLTFGGGTKVEIK SEQ ID NO. 203 [XA4 Heavy Chain]
QVHLVESGGGVVQPGRSLRLSCVASGITFRIYGMHWVRQAPGKGLEWVAVLWYDGSHEY
YADSVKGRFTISRDNSKNTLYLQMNSLRAEDTAIYYCARDGDYYDSGSPLDYWGQGTLVT
VSSASTKGPSVFPLAPSSKSTSGGTAALGCLVKDYFPEPVTVSWNSGALTSGVHTFPAVLQ

| SEQUENCES |
| --- |

SSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
<u>N*</u>STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPG
<u>N*</u> indicates Asn297

SEQ ID NO. 204 [XA4 Light Chain]
EIVLTQSPATLSLSPGERATLSCRASQSVSSYLAWYQQKPGQAPRLLIYDASNRATGIPARF
SGSGSGTDFTLTISSLEPEDFAVYYCQQRSNWPLTFGGGTKVEIKRTVAAPSVFIFPPSDEQ
LKSGTASVVCLLNNFYPREAKVQWKVDNALQSGNSQESVTEQDSKDSTYSLSSTLTLSKA
DYEKHKVYACEVTHQGLSSPVTKSFNRGEC

SEQ ID NO. 205 [XA4 VH CDR1]
IYGMH

SEQ ID NO. 206 [XA4 VH CDR2]
VLWYDGSHEYYADSVKG

SEQ ID NO. 207 [XA4 VH CDR3]
DGDYYDSGSPLDY

SEQ ID NO. 208 [XA4 VL CDR1]
RASQSVSSYLA

SEQ ID NO. 209 [XA4 VL CDR21]
DASNRAT

SEQ ID NO. 210 [XA4 VL CDR31]
QQRSNWPLT

SEQ ID NO. 211 [XA4 Heavy Chain, terminal K]
QVHLVESGGGVVQPGRSLRLSCVASGITFRIYGMHWVRQAPGKGLEWVAVLWYDGSHEY
YADSVKGRFTISRDNSKNTLYLQMNSLRAEDTAIYYCARDGDYYDSGSPLDYWGQGTLVT
VSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
<u>N*</u>STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK
<u>N*</u> indicates Asn297

SEQ ID NO. 212 [XFT VH, CDR underline]
QVELVQSGAVKKPGESLKISCKGS<u>GYSFTSYWIG</u>WVRQAPGKGLE<u>WMGIIDPGDSRTRYS
PSFQG</u>QVTISADKSISTAYLQWSSLKASDTAMYYCAR<u>GQLYGGTYMDG</u>WGQGTLVTVSS SEQ ID NO. 213 [XFT VL, CDR underline]
DIALTQPASVSGSPGQSITISC<u>TGTSSDIGGYNSVS</u>WYQQHPGKAPK<u>LMIYGVNNRPS</u>GVS
NRFSGSKSGNTASLTISGLQAEDEADYYC<u>SSYDIESATP</u>VFGGGTKLEIK SEQ ID NO. 214 [XFT Heavy Chain]
QVELVQSGAVKKPGESLKISCKGSGYSFTSYWIGWVRQAPGKGLEWMGIIDPGDSRTRYS
PSFQGQVTISADKSISTAYLQWSSLKASDTAMYYCARGQLYGGTYMDGWGQGTLVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQY<u>N*</u>STY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPG
<u>N*</u> indicates Asn297

SEQ ID NO. 215 [XFT Light Chain]
DIALTQPASVSGSPGQSITISCTGTSSDIGGYNSVSWYQQHPGKAPKLMIYGVNNRPSGVS
NRFSGSKSGNTASLTISGLQAEDEADYYCSSYDIESATPVFGGGTKLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

SEQ ID NO. 216 [XFT VH CDR1]
GYSFTSYWIG

SEQ ID NO. 217 [KFT VH CDR2]
WMGIIDPGDSRTRYSPSFQG

SEQ ID NO. 218 [XFT VH CDR3]
GQLYGGTYMDG

SEQUENCES

SEQ ID NO. 219 [XFT VL CDR1]
TGTSSDIGGYNSVS

SEQ ID NO. 220 [XFT VL CDR2]
LMIYGVNNRPS

SEQ ID NO. 221 [XFT VL CDR3]
SSYDI ESATP

SEQ ID NO. 222 [XFT Heavy Chain, terminal K]
QVELVQSGAVKKPGESLKISCKGSGYSFTSYWIGWVRQAPGKGLEWMGIIDPGDSRTRYS
PSFQGQVTISADKSISTAYLQWSSLKASDTAMYYCARGQLYGGTYMDGWGQGTLVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYN*STY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK
N* indicates Asn297

SEQ ID NO. 223 [X09 VH, CDR underline]
QVQLQQSGPELEKPGASVKISCKAS<u>GYSFTGYTMNWVKQSHGKSLEWIG<u>LITPYNGASSY
NQKFRG</u>KATLTVDKSSSTAYMDLLSLTSEDSAVYFCAR<u>GGYDGRGFDY</u>WGSGTPVTVSS SEQ ID NO. 224 [X09 VL, CDR underline]
DIELTQSPAIMSASPGEKVTMTC<u>SASSSVSYMH</u>WYQQKSGTSPKRWIY<u>DTSKLAS</u>GVPGR
FSGSGSGNSYSLTISSVEAEDDATYYC<u>QQWSKHPLT</u>FGSGTKVEIK SEQ ID NO. 225 [X09 Heavy Chain]
QVQLQQSGPELEKPGASVKISCKASGYSFTGYTMNWVKQSHGKSLEWIGLITPYNGASSY
NQKFRGKATLTVDKSSSTAYMDLLSLTSEDSAVYFCARGGYDGRGFDYWGSGTPVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQY<u>N*</u>STY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPG
N* indicates Asn297

SEQ ID NO. 226 [X09 Light Chain]
DIELTQSPAIMSASPGEKVTMTCSASSSVSYMHWYQQKSGTSPKRWIYDTSKLASGVPGR
FSGSGSGNSYSLTISSVEAEDDATYYCQQWSKHPLTFGSGTKVEIKRTVAAPSVFIFPPSDE
QLKSGTASVVCLLNNFYPREAKVQWKVDNALQSGNSQESVTEQDSKDSTYSLSSTLTLSK
ADYEKHKVYACEVTHQGLSSPVTKSFNRGEC

SEQ ID NO. 227 [X09 VH CDR1]
GYSFT

SEQ ID NO. 228 [X09 VH CDR2]
LITPYNGASSYNQKFRG

SEQ ID NO. 229 [X09 VH CDR3]
GGYDGRGFDY

SEQ ID NO. 230 [X09 VL CDR1]
SASSSVSYMH

SEQ ID NO. 231 [X09 VL CDR2]
DTSKLAS

SEQ ID NO. 232 [X09 VL CDR3]
QQWSKHPLT

SEQ ID NO. 233 [X09 Heavy Chain, terminal K]
QVQLQQSGPELEKPGASVKISCKASGYSFTGYTMNWVKQSHGKSLEWIGLITPYNGASSY
NQKFRGKATLTVDKSSSTAYMDLLSLTSEDSAVYFCARGGYDGRGFDYWGSGTPVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQY<u>N*</u>STY
RVVSVLTVLHQDWLNGKEYKCKVSNKALPAPIEKTISKAKGQPREPQVYTLPPSRDELTKN

| SEQUENCES |
|---|

QVSLTCLVKGFYPSDIAVEWESNGQPENNYKTTPPVLDSDGSFFLYSKLTVDKSRWQQGN
VFSCSVMHEALHNHYTQKSLSLSPGK
N* indicates Asn297

SEQ ID NO. 234 [X09.2 VH, CDR underline]
QVQLQQSGPELEKPGASVKISCKASGYSFT<u>GYTMN</u>WVKQSHGKSLEWIG<u>LITPYNGASSY
NQKFRG</u>KATLTVDKSSSTAYMDLLSLTSEDSAVYFCAR<u>GGYDGRGFDY</u>WGQGTTVTVSS SEQ ID NO. 235 [X09.2 VL, CDR underline]
DIELTQSPAIMSASPGEKVTMTC<u>SASSSVSYMH</u>WYQQKSGTSPKRWIY<u>DTSKLAS</u>GVPGR
FSGSGSGNSYSLTISSVEAEDDATYYC<u>QQWSGYPLT</u>FGAGTKLEIK SEQ ID NO. 236 [X09.2 Heavy Chain]
QVQLQQSGPELEKPGASVKISCKASGYSFTGYTMNWVKQSHGKSLEWIGLITPYNGASSY
NQKFRGKATLTVDKSSSTAYMDLLSLTSEDSAVYFCARGGYDGRGFDYWGSGTPVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQY<u>N</u>*STY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPG
N* indicates Asn297

SEQ ID NO. 237 [X09.2 Light Chain]
DIELTQSPAIMSASPGEKVTMTCSASSSVSYMHWYQQKSGTSPKRWIYDTSKLASGVPGR
FSGSGSGNSYSLTISSVEAEDDATYYCQQWSKHPLTFGSGTKVEIKRTVAAPSVFIFPPSDE
QLKSGTASVVCLLNNFYPREAKVQWKVDNALQSGNSQESVTEQDSKDSTYSLSSTLTLSK
ADYEKHKVYACEVTHQGLSSPVTKSFNRGEC

SEQ ID NO. 238 [X09.2 VH CDR1]
GYTMN

SEQ ID NO. 239 [X09.2 VH CDR2]
LITPYNGASSYNQKFRG

SEQ ID NO. 240 [X09.2 VH CDR3]
GGYDGRGFDY

SEQ ID NO. 241 [X09.2 VL CDR1]
SASSSVSYMH

SEQ ID NO. 242 [X09.2 VL CDR2]
DTSKLAS

SEQ ID NO. 243 [X09.2 VL CDR3]
QQWSGYPLT

SEQ ID NO. 244 [X09.2 Heavy Chain, terminal K]
QVQLQQSGPELEKPGASVKISCKASGYSFTGYTMNWVKQSHGKSLEWIGLITPYNGASSY
NQKFRGKATLTVDKSSSTAYMDLLSLTSEDSAVYFCARGGYDGRGFDYWGSGTPVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQY<u>N</u>*STY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPGK
N* indicates Asn297

SEQ ID NO. 245 [Human Mesothelin, variant 1]
MALPTARPLLGSCGTPALGSLLFLLFSLGWVQPSRTLAGETGQEAAPLDGVLANPPNISS
LSPRQLLGFPCAEVSGLSTERVRELAVALAQKNVKLSTEQLRCLAHRLSEPPEDLDALPL
DLLLFLNPDAFSGPQACTRFFSRITKANVDLLPRGAPERQRLLPAALACWGVRGSLLSEA
DVRALGGLACDLPGRFVAESAEVLLPRLVSCPGPLDQDQQEAARAALQGGGPPYGPPST
WSVSTMDALRGLLPVLGQPIIRSIPQGIVAAWRQRSSRDPSWRQPERTILRPRFRREVEKT
ACPSGKKAREIDESLIFYKKWELEACVDAALLATQMDRVNAIPFTYEQLDVLKHKLDELY
PQGYPESVIQHLGYLFLKMSPEDIRKWNVTSLETLKALLEVNKGHEMSPQAPRRPLPQVA
TLIDRFVKGRGQLDKDTLDTLTAFYPGYLCSLSPEELSSVPPSSIWAVRPQDLDTCPRQ
LDVLYPKARLAFQNMNGSEYFVKIQSFLGGAPTEDLKALSQQNVSMDLATFMKLRTDAVL
PLTVAEVQKLLGPHVEGLKAEERHRPVRDWILRQRQDDLDTLGLGLQGGIPNGYLVLDLS
MQEALSGTPCLLGPGPVLTVLALLLASTLA SEQ ID NO. 246 [Human Mesothelin, variant 2]
MALPTARPLLGSCGTPALGSLLFLLFSLGWVQPSRTLAGETGQEAAPLDGVLANPPNISS
LSPRQLLGFPCAEVSGLSTERVRELAVALAQKNVKLSTEQLRCLAHRLSEPPEDLDALPL
DLLLFLNPDAFSGPQACTRFFSRITKANVDLLPRGAPERQRLLPAALACWGVRGSLLSEA
DVRALGGLACDLPGRFVAESAEVLLPRLVSCPGPLDQDQQEAARAALQGGGPPYGPPST
WSVSTMDALRGLLPVLGQPIIRSIPQGIVAAWRQRSSRDPSWRQPERTILRPRFRREVEKT

```
ACPSGKKAREIDESLIFYKKWELEACVDAALLATQMDRVNAIPFTYEQLDVLKHKLDELY
PQGYPESVIQHLGYLFLKMSPEDIRKWNVTSLETLKALLEVNKGHEMSPQVATLIDRFVK
GRGQLDKDTLDTLTAFYPGYLCSLSPEELSSVPPSSIWAVRPQDLDTCDPRQLDVLYPKA
RLAFQNMNGSEYFVKIQSFLGGAPTEDLKALSQQNVSMDLATFMKLRTDAVLPLTVAEVQ
KLLGPHVEGLKAEERHRPVRDWILRQRQDDLDTLGLGLQGGIPNGYLVLDLSMQEALSGT
PCLLGPGPVLTVLALLLASTLA
```

The invention claimed is:
1. A conjugate of formula (I):

$$Ab\text{-}(DL)_p \qquad (I)$$

wherein:
Ab is an antibody that binds to DLK1 and comprises a VH domain comprising a VH CDR1 with the amino acid sequence of SEQ ID NO.5, a VH CDR2 with the amino acid sequence of SEQ ID NO.6, and a VH CDR3 with the amino acid sequence of SEQ ID NO.7; and, a VL domain comprising a VL CDR1 with the amino acid sequence of SEQ ID NO.8, a VL CDR2 with the amino acid sequence of SEQ ID NO.9, and a VL CDR3 with the amino acid sequence of SEQ ID NO.10;
wherein DL is

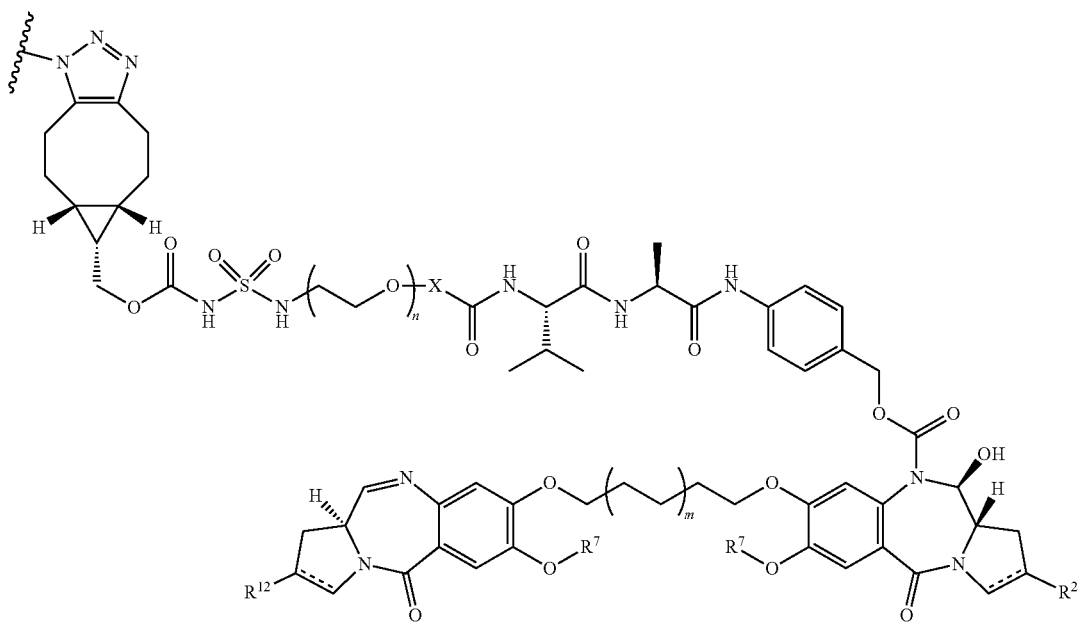

wherein:
X is selected from the group comprising: a single bond, —CH2— and —$C_2H_4$—;
n is from 1 to 8;
m is 0 or 1;
$R^7$ is either methyl or phenyl;
when there is a double bond between C2 and C3, $R^2$ is selected the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

wherein one of $R^{25}a$ and $R^{25b}$ is H and the other is selected from: phenyl, which phenyl is optionally substituted by a group selected from halo, methyl, methoxy pyridyl and thiophenyl; and (if)

where $R^{24}$ is selected from: H, $C_{1-3}$ saturated alkyl $C_{2-3}$ alkenyl, $C_{2-3}$ alkynyl cyclopropyl phenyl, which phenyl is optionally substituted by a group selected from halo, methyl, methoxy pyridyl and thiophenyl;

when there is a single bond between C2 and C3, $R^2$ is

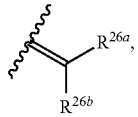

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26}a$ and $R^{26b}$ is H, the other is selected from nitrile and a $C_{1-4}$ alkyl ester;

when there is a double bond between C2' and C3', $R^{12}$ is selected the group consisting of:

(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(iib) $C_{1-5}$ saturated aliphatic alkyl;

(iic) $C_{3-6}$ saturated cycloalkyl;

(iid)

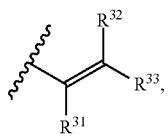

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(iie)

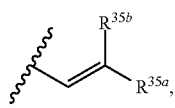

wherein one of $R^{35a}$ and $R^{35b}$ is H and the other is selected from: phenyl, which phenyl is optionally substituted by a group selected from halo, methyl, methoxy pyridyl, and thiophenyl; and (iif)

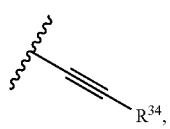

wherein $R^{34}$ is selected from: H, $C_{1-3}$ saturated alkyl, $C_{2-3}$ alkenyl, $C_{2-3}$ alkynyl, cyclopropyl, phenyl, which phenyl is optionally substituted by a group selected from halo, methyl, methoxy, pyridyl, and thiophenyl;

when there is a single bond between C2' and C3', $R^{12}$ is

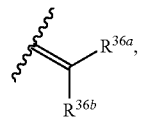

where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{36a}$ and $R^{36b}$ is H, the other is selected from nitrile and a $C_{1-4}$ alkyl ester;

and p is from 1 to 8.

2. The conjugate according to claim 1, wherein X is —$CH_2$—.

3. The conjugate according to claim 1, wherein n is 1 to 4.

4. The conjugate according to claim 3, wherein n is 2.

5. The conjugate according to claim 1, wherein there is a double bond between C2 and C3, and $R^2$ is a $C_{1-5}$ saturated aliphatic alkyl group.

6. The conjugate according to claim 5, wherein $R^2$ is methyl, ethyl or propyl.

7. The conjugate according to claim 1, wherein there is a double bond between C2 and C3, and $R^2$ is:

(a) phenyl, which bears one to three substituent groups, wherein the substituents may be selected from methoxy, ethoxy, fluoro, chloro, cyano, bis-oxy-methylene, methyl-piperazinyl, morpholino and methyl-thiophenyl;

(b) cyclopropyl;

(c) a group of formula:

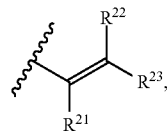

wherein the total number of carbon atoms in the $R^2$ group is no more than 3;

(d) the group:

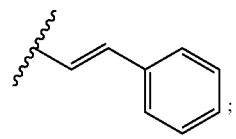 [SMILES: */C=C/c1ccccc1]

or (e) a group of formula:

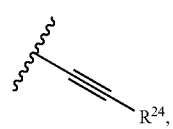

wherein $R^{24}$ is selected from H and methyl.

8. The conjugate according to claim 1, wherein there is a single bond between C2 and C3, $R^2$ is

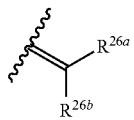

and
  (a) $R^{26a}$ and $R^{26b}$ are both H;
  (b) $R^{26a}$ and $R^{26b}$ are both methyl; or
  (c) one of $R^{26a}$ and $R^{26b}$ is H, and the other is selected from $C_{1-4}$ saturated alkyl, $C_{2-3}$ alkenyl, which alkyl and alkenyl groups are optionally substituted.

9. The conjugate according to claim 1, wherein there is a double bond between C2' and C3', and $R^{12}$ is a $C_{1-5}$ saturated aliphatic alkyl group.

10. The conjugate according to claim 9, wherein $R^{12}$ is methyl, ethyl or propyl.

11. The conjugate according to claim 1, wherein there is a double bond between C2' and C3', and $R^{12}$ is:
  (a) phenyl, which bears one to three substituent groups, wherein the substituents are selected from methoxy, ethoxy, fluoro, chloro, cyano, bis-oxy-methylene, methyl-piperazinyl, morpholino and methyl-thiophenyl;
  (b) cyclopropyl;
  (c) a group of formula:

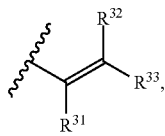

wherein the total number of carbon atoms in the $R^{12}$ group is no more than 3;

(d) the group:

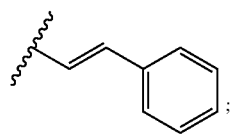 [SMILES: */C=C/c1ccccc1]

or (e) a group of formula:

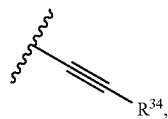

wherein $R^{34}$ is selected from H and methyl.

12. The conjugate according to claim 1, wherein there is a single bond between C2' and C3', $R^{12}$ is

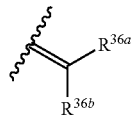

and
  (a) $R^{36a}$ and $R^{36b}$ are both H;
  (b) $R^{36a}$ and $R^{36b}$ are both methyl; or
  (c) one of $R^{36a}$ and $R^{36b}$ is H, and the other is selected from $C_{1-4}$ saturated alkyl, $C_{2-3}$ alkenyl, which alkyl and alkenyl groups are optionally substituted.

13. The conjugate according to claim 1, wherein DL is:

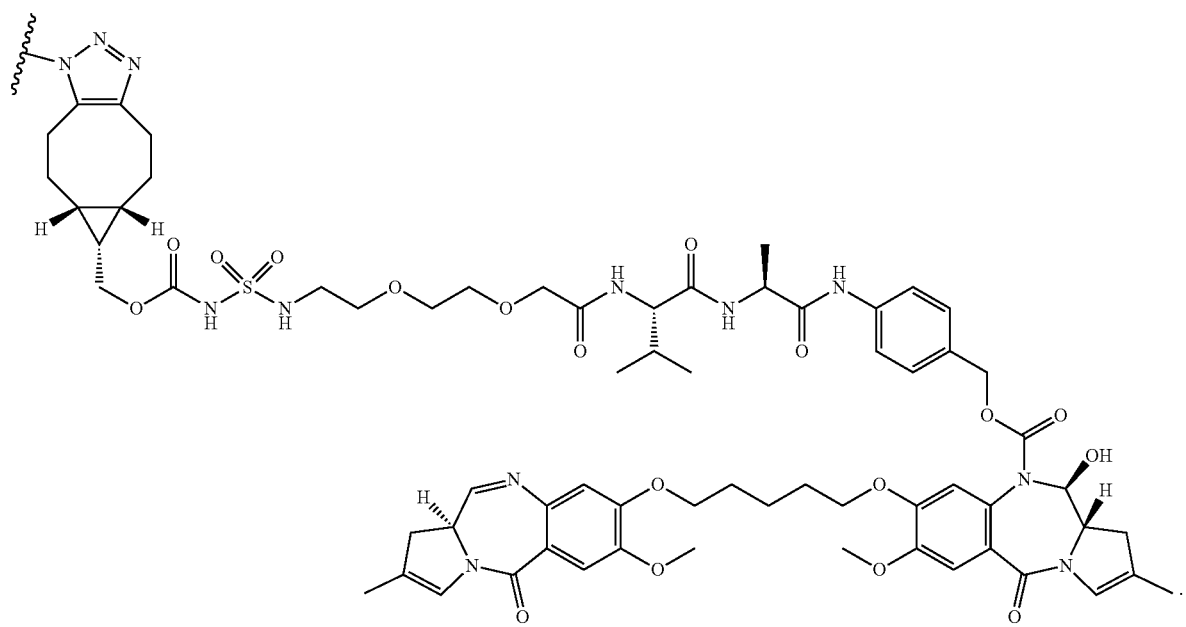 [SMILES: *n1nnc2c1CC[C@@H]1[C@H](CC2)[C@@H]1COC(=O)NS(=O)(=O)NCCOCCOCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4C=N5)c(OC)cc3C(=O)N3C=C(C)C[C@H]3[C@@H]2O)cc1)C(C)C]

14. The conjugate according to claim 1, wherein the antibody comprises a VH domain having the sequence of SEQ ID NO.1.

15. The conjugate according to claim 1, wherein the antibody comprises a VL domain having the sequence of SEQ ID NO. 2.

16. The conjugate according to claim 1, wherein the antibody comprises a heavy chain having the sequence of SEQ ID NO. 3, or a heavy chain having the sequence of SEQ ID NO. 11.

17. The conjugate according to claim 1, wherein the antibody comprises a light chain having the sequence of SEQ ID NO. 4.

18. A composition comprising a mixture of conjugates as defined in claim 1, wherein the average drug loading per antibody in the mixture of conjugates is about 1 to about 4.

19. A pharmaceutical composition comprising the conjugate of claim 1, and a pharmaceutically acceptable diluent, carrier or excipient.

20. The pharmaceutical composition of claim 19, further comprising a therapeutically effective amount of a chemotherapeutic agent.

21. A conjugate of formula (I):

$$Ab\text{-}(DL)_p \qquad (I)$$

wherein:
Ab is an antibody that binds to DLK1 and comprises a VH domain comprising a VH CDR1 with the amino acid sequence of SEQ ID NO.5, a VH CDR2 with the amino acid sequence of SEQ ID NO.6, and a VH CDR3 with the amino acid sequence of SEQ ID NO.7; and, a VL domain comprising a VL CDR1 with the amino acid sequence of SEQ ID NO.8, a VL CDR2 with the amino acid sequence of SEQ ID NO.9, and a VL CDR3 with the amino acid sequence of SEQ ID NO.10;

wherein DL is

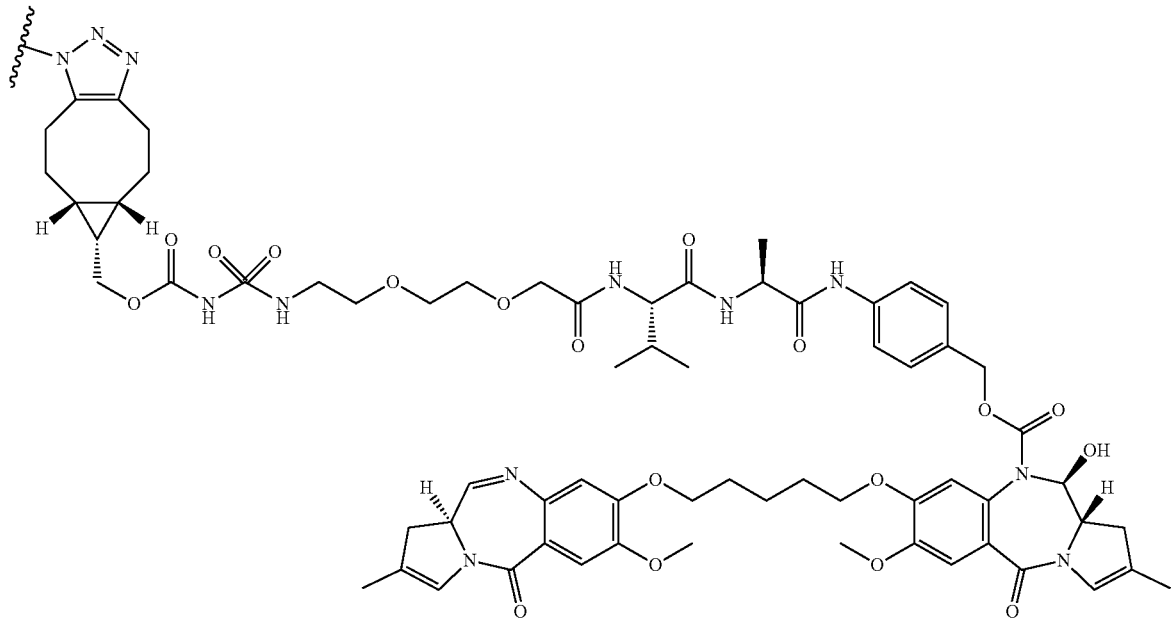

and p is from 1 to 8.

22. The conjugate according to claim 21, wherein the antibody comprises a VH domain having the sequence of SEQ ID NO.1 and a VL domain having the sequence of SEQ ID NO. 2.

23. A composition comprising a mixture of conjugates as defined in claim 21, wherein the average drug loading per antibody in the mixture of conjugates is about 1 to about 4.

24. A pharmaceutical composition comprising the conjugate of claim 21, and a pharmaceutically acceptable diluent, carrier or excipient.

25. The pharmaceutical composition of claim 24, further comprising a therapeutically effective amount of a chemotherapeutic agent.

* * * * *